(12) United States Patent
Armela et al.

(10) Patent No.: US 7,727,440 B2
(45) Date of Patent: Jun. 1, 2010

(54) METHODS OF MAKING FASTENER PRODUCTS

(75) Inventors: Luis Parellada Armela, Palafrugell (ES); Juan Sánchez, Argentona (ES); William Clune, Northwood, NH (US); Jefferson Davis, Antrim, NH (US); Christopher M. Gallant, Nottingham, NH (US); Melissa Spezzafero, Danville, NH (US); Mark A. Clarner, Concord, NH (US); William L. Huber, Epsom, NH (US); David P. Kraus, Jr., Amherst, NH (US); George A. Provost, Litchfield, NH (US); Howard A. Kingsford, Amherst, NH (US); Michel Labrecque, Manchester, NH (US)

(73) Assignee: Velcro Industries B.V., Curacao (AN)

( * ) Notice: Subject to any disclaimer, the term of this patent is extended or adjusted under 35 U.S.C. 154(b) by 763 days.

(21) Appl. No.: 11/005,185

(22) Filed: Dec. 6, 2004

(65) Prior Publication Data
US 2005/0091805 A1 May 5, 2005

Related U.S. Application Data

(60) Division of application No. 10/163,169, filed on Jun. 4, 2002, now Pat. No. 6,991,843, which is a continuation-in-part of application No. 09/870,063, filed on May 30, 2001, now Pat. No. 6,708,378, which is a division of application No. 09/231,134, filed on Jan. 15, 1999, now Pat. No. 6,248,276, and a continuation-in-part of application No. 09/808,395, filed on Mar. 14, 2001, now Pat. No. 7,048,818.

(60) Provisional application No. 60/295,937, filed on Jun. 4, 2001.

(51) Int. Cl.
B29C 47/00 (2006.01)
A44B 18/00 (2006.01)

(52) U.S. Cl. .................... 264/177.17; 264/80; 264/167; 264/210.2; 264/285; 264/295; 264/296; 264/320; 264/444; 428/99; 428/100; 24/443; 24/446; 24/452

(58) Field of Classification Search ....................... None
See application file for complete search history.

(56) References Cited

U.S. PATENT DOCUMENTS 2,820,277 A 1/1958 Förster
2,820,877 A 1/1958 Oates, Jr.

(Continued)

FOREIGN PATENT DOCUMENTS

DE 2 213 686 3/1972

(Continued)

OTHER PUBLICATIONS

Velcro Fastener Application Publications, Velcro International Ltd., 7 pp (published prior to Jan. 15, 1998).
US 6,129,874, 10/2000, Buzzell et al. (withdrawn)

*Primary Examiner*—Jeffrey Wollschlager
(74) *Attorney, Agent, or Firm*—Fish & Richardson P.C.

(57) ABSTRACT

A method of forming a fastener is provided, including (a) forming, from a thermoformable material, a preform product having a sheet-form base and an array of preform stems integrally molded with and extending from the base to corresponding terminal ends; (b) heating the terminal ends of the stems to a predetermined softening temperature, while maintaining the sheet-form base and a lower portion of each stem at a temperature lower than the softening temperature; and (c) contacting the terminal ends with a contact surface that is at a predetermined forming temperature, lower than the softening temperature, to deform the terminal ends to form heads therefrom that overhang the sheet-form base. Fasteners and other methods of forming them are also provided.

23 Claims, 60 Drawing Sheets

U.S. PATENT DOCUMENTS

| | | | |
|---|---|---|---|
| 3,138,841 A | 6/1964 | Naimer | |
| 3,191,255 A | 6/1965 | Nealis | |
| 3,192,589 A | 7/1965 | Pearson | |
| 3,261,069 A | 7/1966 | Mathison | |
| 3,266,113 A | 8/1966 | Flanagan, Jr. | |
| 3,312,583 A | 4/1967 | Rochlis | |
| 3,399,425 A | 9/1968 | Lemelson | |
| 3,408,705 A | 11/1968 | Kayser et al. | |
| 3,527,001 A | 9/1970 | Kleemeier et al. | |
| 3,557,407 A | 1/1971 | Lemelson | |
| 3,590,109 A | 6/1971 | Doleman et al. | |
| 3,718,725 A * | 2/1973 | Hamano | 264/163 |
| 3,808,648 A | 5/1974 | Billarant et al. | |
| 4,001,366 A * | 1/1977 | Brumlik | 264/147 |
| 4,169,303 A | 10/1979 | Lemelson | |
| 4,290,174 A | 9/1981 | Kalleberg | |
| 4,454,183 A | 6/1984 | Wollman | |
| 4,515,651 A * | 5/1985 | MacLaughlin et al. | 156/423 |
| 4,775,310 A | 10/1988 | Fischer | |
| 4,794,028 A | 12/1988 | Fischer | |
| 4,880,589 A | 11/1989 | Shigemoto et al. | |
| 4,894,060 A | 1/1990 | Nestegard | |
| 5,076,793 A | 12/1991 | Aghevli et al. | |
| 5,077,870 A * | 1/1992 | Melbye et al. | 24/452 |
| 5,396,687 A | 3/1995 | Osterman | |
| 5,505,747 A | 4/1996 | Chesley et al. | |
| 5,607,635 A | 3/1997 | Melbye et al. | |
| 5,657,516 A | 8/1997 | Berg et al. | |
| 5,679,302 A | 10/1997 | Miller et al. | |
| 5,685,050 A | 11/1997 | Murasaki | |
| 5,713,111 A | 2/1998 | Hattori et al. | |
| 5,725,015 A | 3/1998 | Theodos et al. | |
| 5,749,129 A | 5/1998 | Murasaki et al. | |
| 5,755,015 A | 5/1998 | Akeno et al. | |
| 5,781,969 A | 7/1998 | Akeno et al. | |
| 5,792,408 A | 8/1998 | Akeno et al. | |
| 5,800,845 A | 9/1998 | Akeno et al. | |
| 5,845,375 A | 12/1998 | Miller et al. | |
| 5,868,987 A | 2/1999 | Kampfer et al. | |
| 5,879,604 A | 3/1999 | Melbye et al. | |
| 5,884,374 A | 3/1999 | Clune | |
| 5,913,482 A | 6/1999 | Akeno | |
| 5,933,927 A | 8/1999 | Miller et al. | |
| 5,951,931 A | 9/1999 | Murasaki et al. | |
| 5,953,797 A | 9/1999 | Provost et al. | |
| 5,981,027 A | 11/1999 | Parellada | |
| 6,000,106 A * | 12/1999 | Kampfer et al. | 24/452 |
| 6,024,824 A * | 2/2000 | Krech | 156/279 |
| 6,039,911 A * | 3/2000 | Miller et al. | 264/280 |
| 6,054,091 A | 4/2000 | Miller et al. | |
| 6,127,018 A | 10/2000 | Akeno et al. | |
| 6,162,040 A * | 12/2000 | Clune | 425/363 |
| 6,248,276 B1 | 6/2001 | Parellada et al. | |
| 6,287,665 B1 | 9/2001 | Hammer | |
| 6,357,088 B2 | 3/2002 | Provost et al. | |
| 6,475,593 B1 | 11/2002 | Hattori et al. | |
| 6,526,633 B2 | 3/2003 | Provost et al. | |
| 6,592,800 B1 * | 7/2003 | Levitt et al. | 264/479 |
| 6,610,231 B2 * | 8/2003 | Takizawa et al. | 264/167 |
| 6,627,133 B1 * | 9/2003 | Tuma | 264/167 |
| 6,678,924 B2 | 1/2004 | Murasaki et al. | |
| 6,708,378 B2 | 3/2004 | Parellada et al. | |
| 7,052,638 B2 | 5/2006 | Clarner et al. | |
| 2001/0018110 A1 | 8/2001 | Tuman et al. | |
| 2002/0022108 A1 | 2/2002 | Krantz et al. | |
| 2002/0069495 A1 | 6/2002 | Murasaki | |
| 2003/0085492 A1 | 5/2003 | Schulte | |
| 2003/0135964 A1 | 7/2003 | Provost et al. | |
| 2004/0033336 A1 | 2/2004 | Schulte | |

FOREIGN PATENT DOCUMENTS

| | | |
|---|---|---|
| DE | 2 213 686 | 10/1972 |
| DE | 296 08 260 | 5/1996 |
| DE | 198 28 856 | 6/1998 |
| DE | 198 28 856 C1 | 6/1998 |
| DE | 100.56.567 | 11/2000 |
| DE | 100 56 567 A1 | 11/2000 |
| EP | 0 806 158 | 3/1997 |
| EP | 0 806 158 A2 | 11/1997 |
| EP | 0 811 331 | 12/1997 |
| EP | 0 811 332 | 12/1997 |
| EP | 0 811 332 A2 | 12/1997 |
| GB | 2 279 106 | 12/1994 |
| GB | 2 349 354 | 11/2000 |
| JP | 4-286029 | 10/1922 |
| WO | WO 82/ 02480 | 8/1982 |
| WO | WO 82/02480 | 8/1982 |
| WO | WO 92/04839 | 4/1992 |
| WO | WO 94/23610 | 10/1994 |
| WO | WO 98/14086 | 4/1998 |
| WO | WO 98/30381 | 7/1998 |
| WO | WO 98/57564 | 12/1998 |
| WO | WO 98/57565 | 12/1998 |
| WO | WO 99/10161 | 3/1999 |
| WO | WO9910161 * | 3/1999 |
| WO | WO 99/26507 | 6/1999 |
| WO | WO 00/00053 | 1/2000 |
| WO | WO0000053 * | 1/2000 |
| WO | WO 00/41479 | 7/2000 |
| WO | WO 01/24654 | 4/2001 |
| WO | WO 02/45536 | 6/2002 |
| WO | WO 02/45536 A2 | 6/2002 |
| WO | WO 03/025499 A1 | 4/2003 |
| WO | WO 03/028499 | 4/2003 |
| WO | WO 03/028499 A | 4/2003 |

* cited by examiner

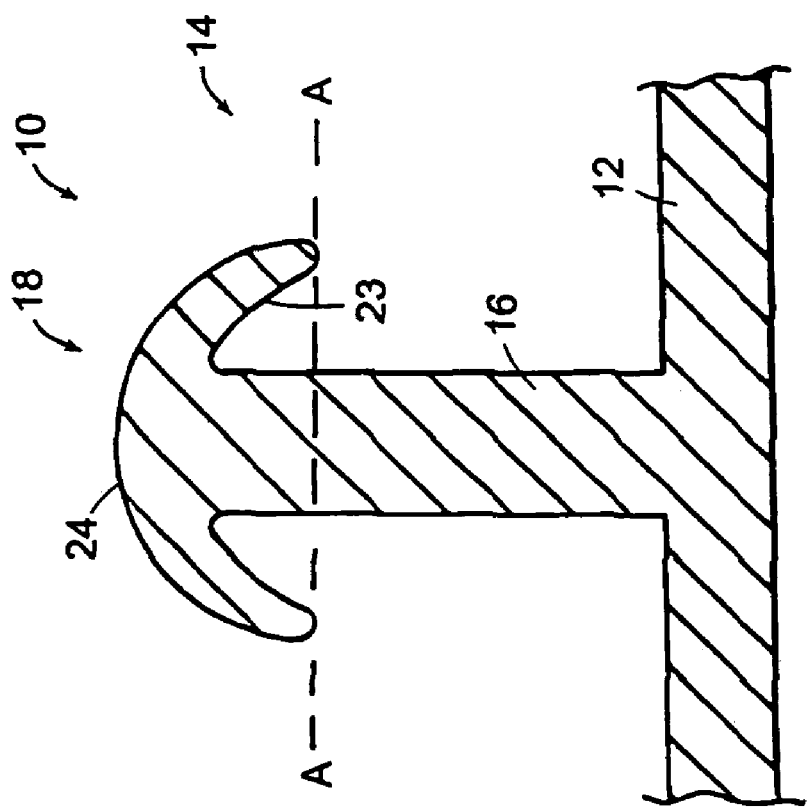
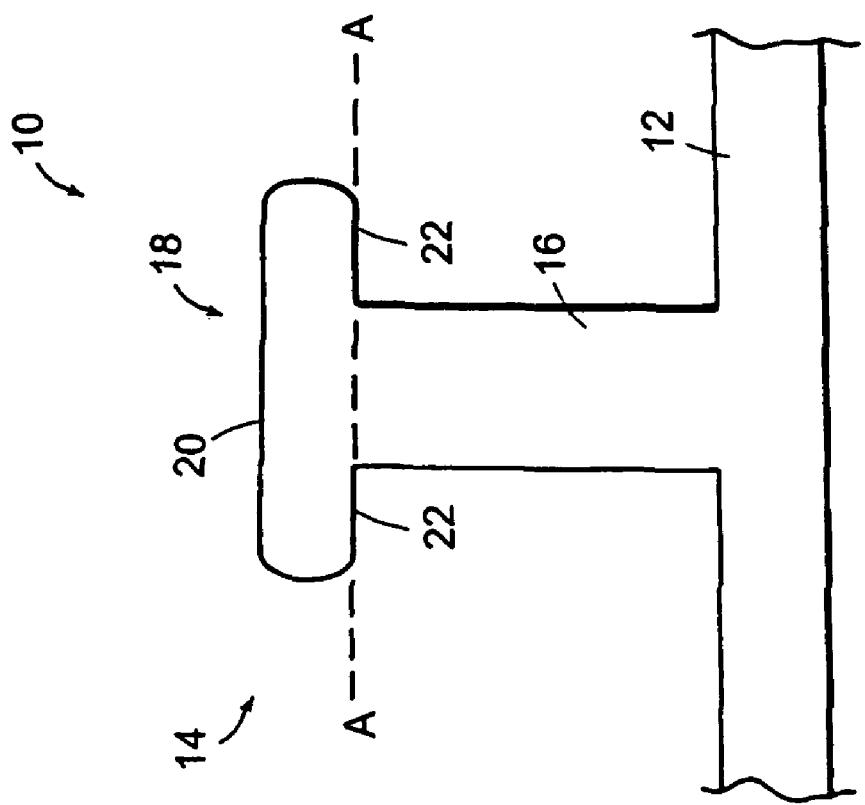

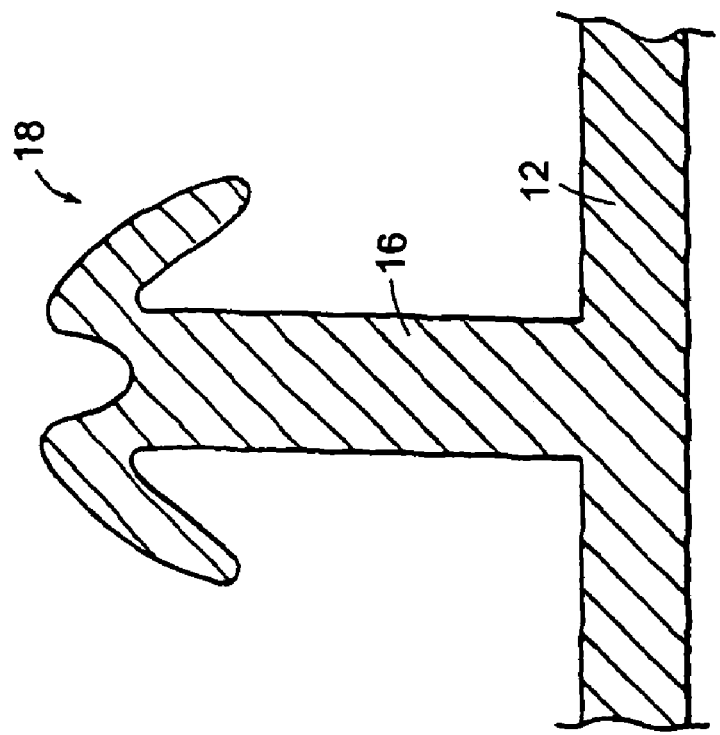
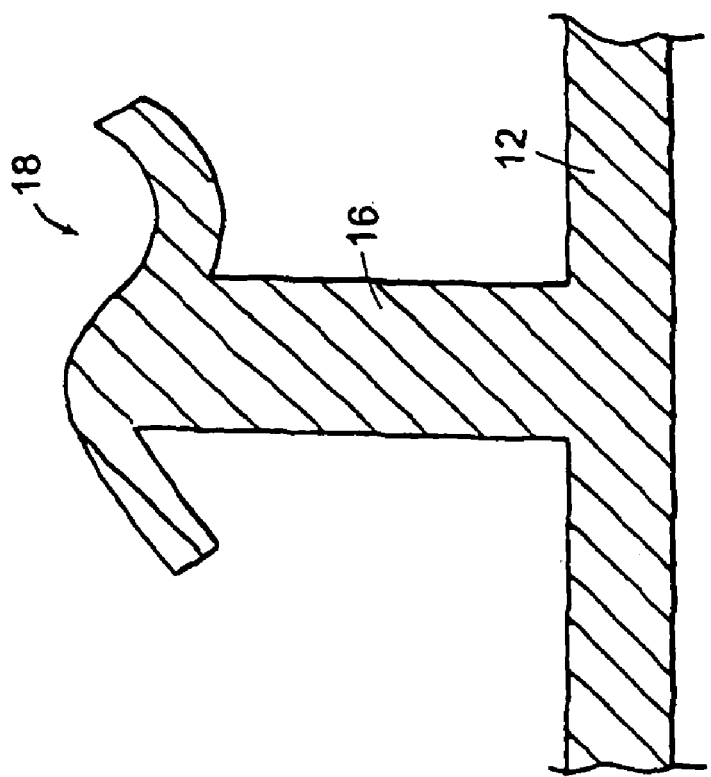

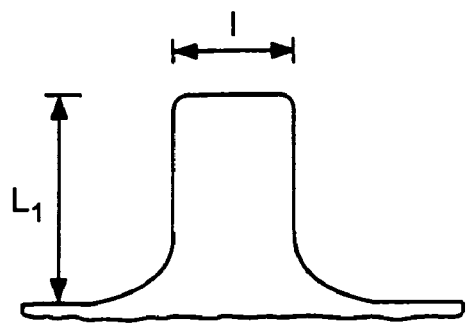
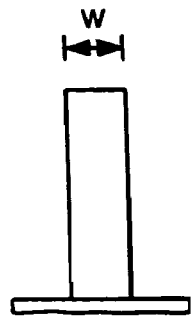
FIG. 15A    FIG. 15B
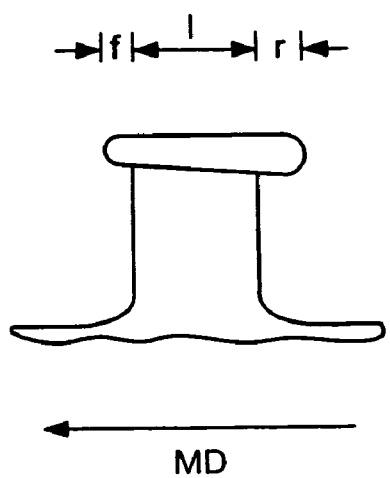
FIG. 16A
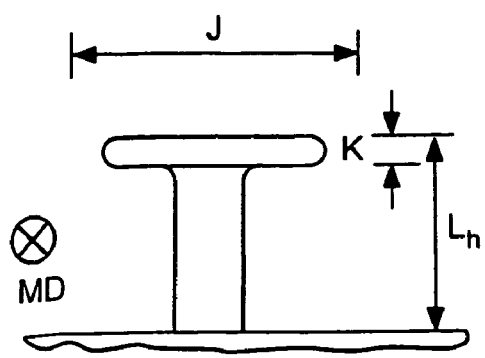
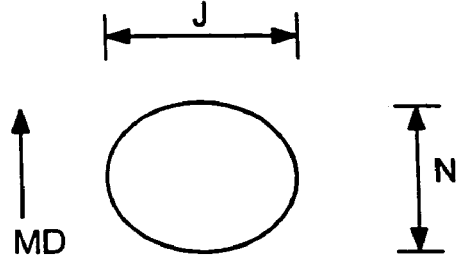
FIG. 16B    FIG. 16C

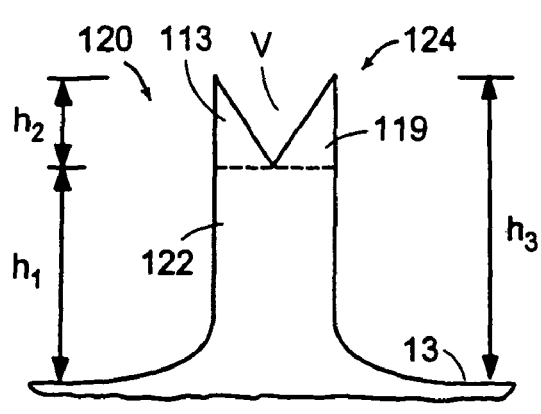
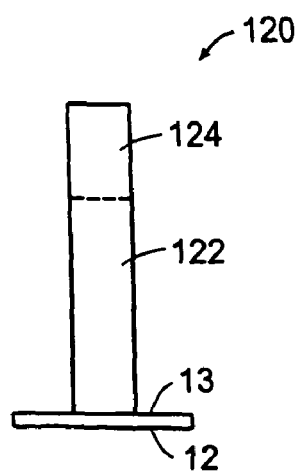
FIG. 17A        FIG. 17B
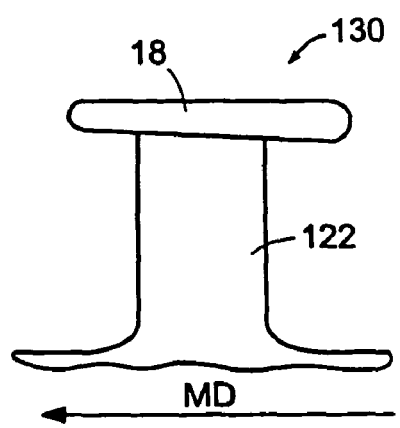
FIG. 18A
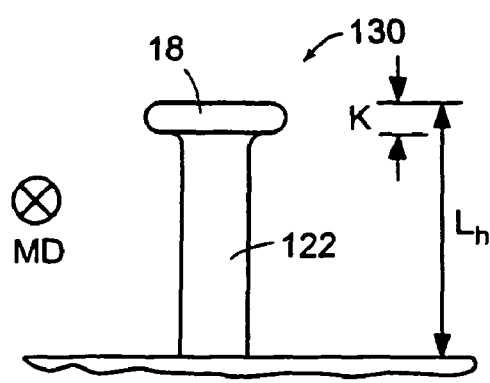
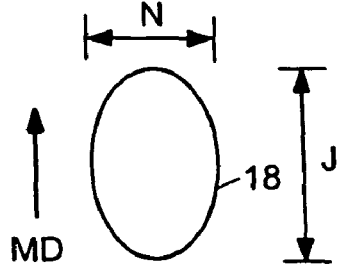
FIG. 18B        FIG. 18C

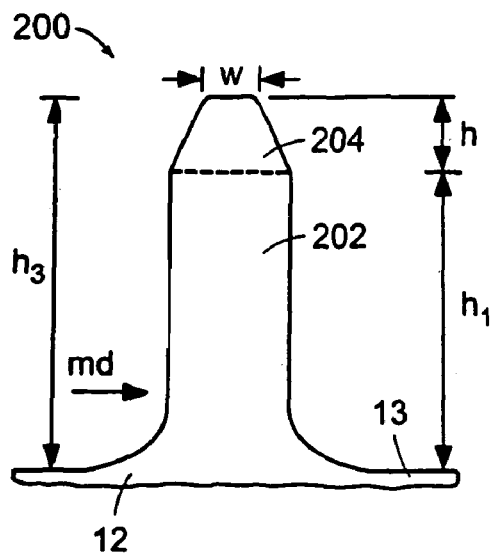
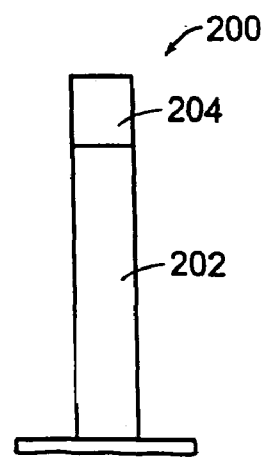
FIG. 19A
FIG. 19B
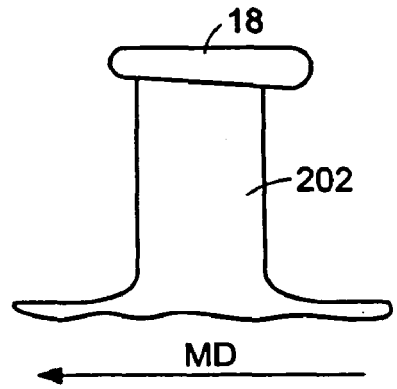
FIG. 20A
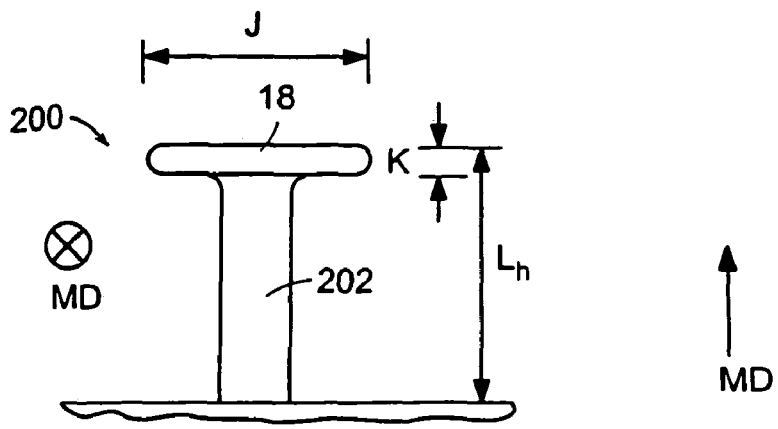
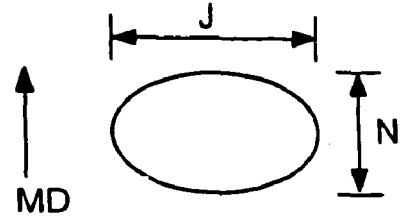
FIG. 20B
FIG. 20C

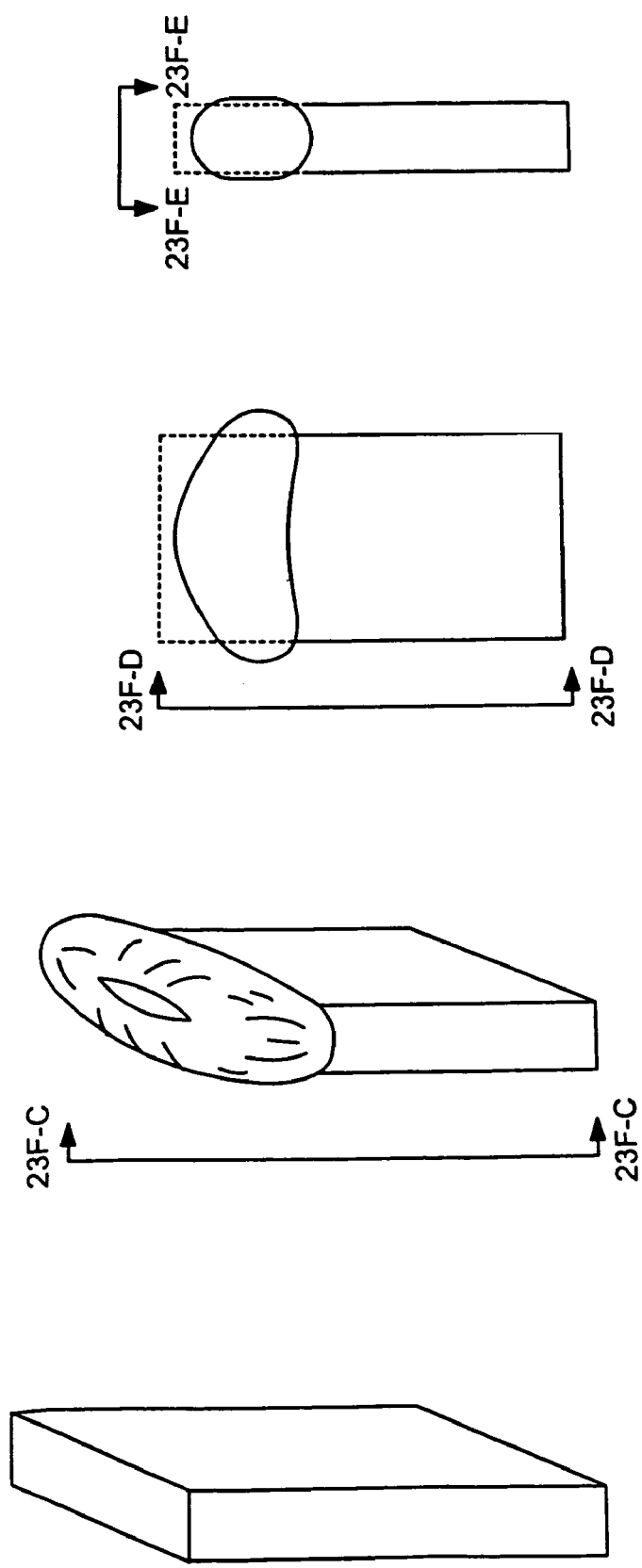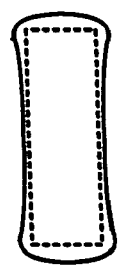
FIG. 23F-D
FIG. 23F-C
FIG. 23F-E
FIG. 23F-B
FIG. 23F-A

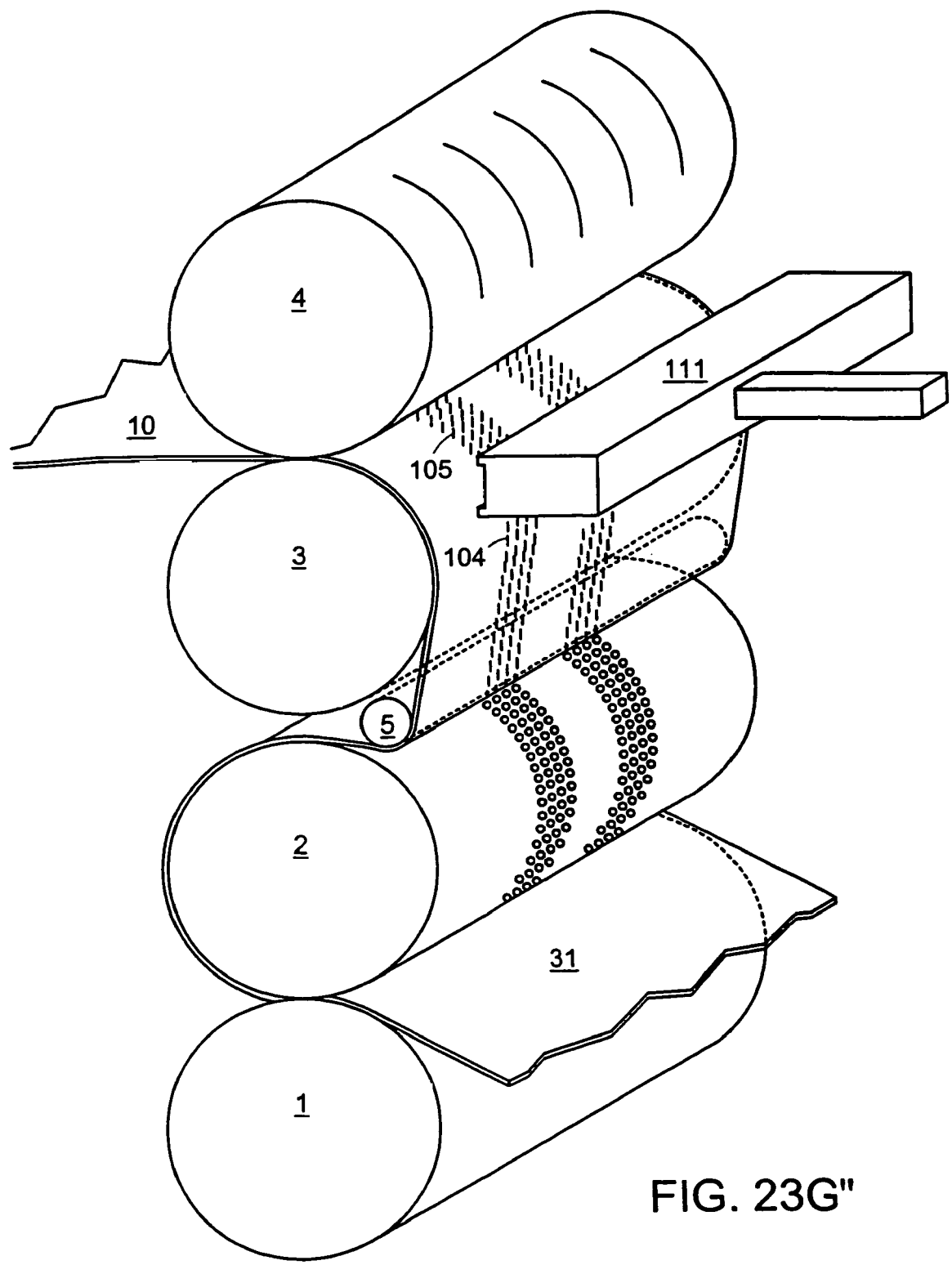
FIG. 23G"

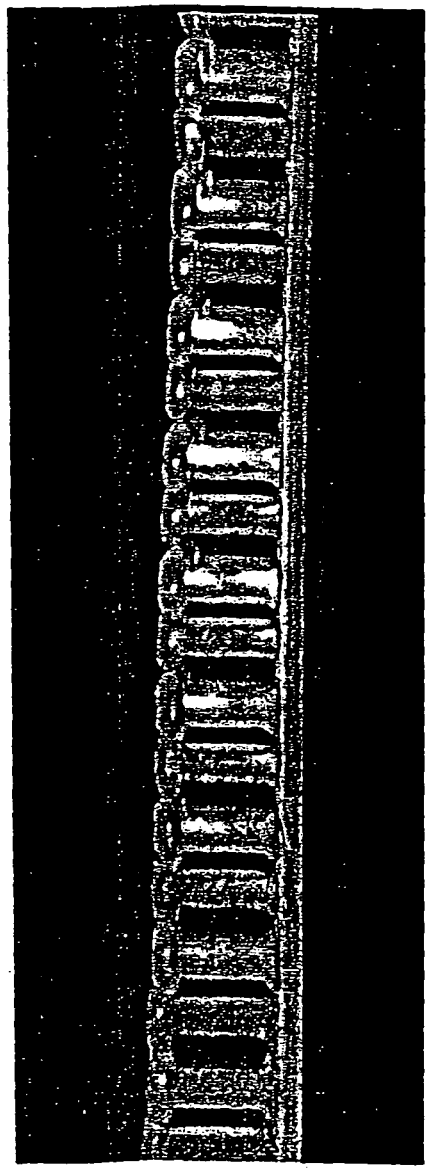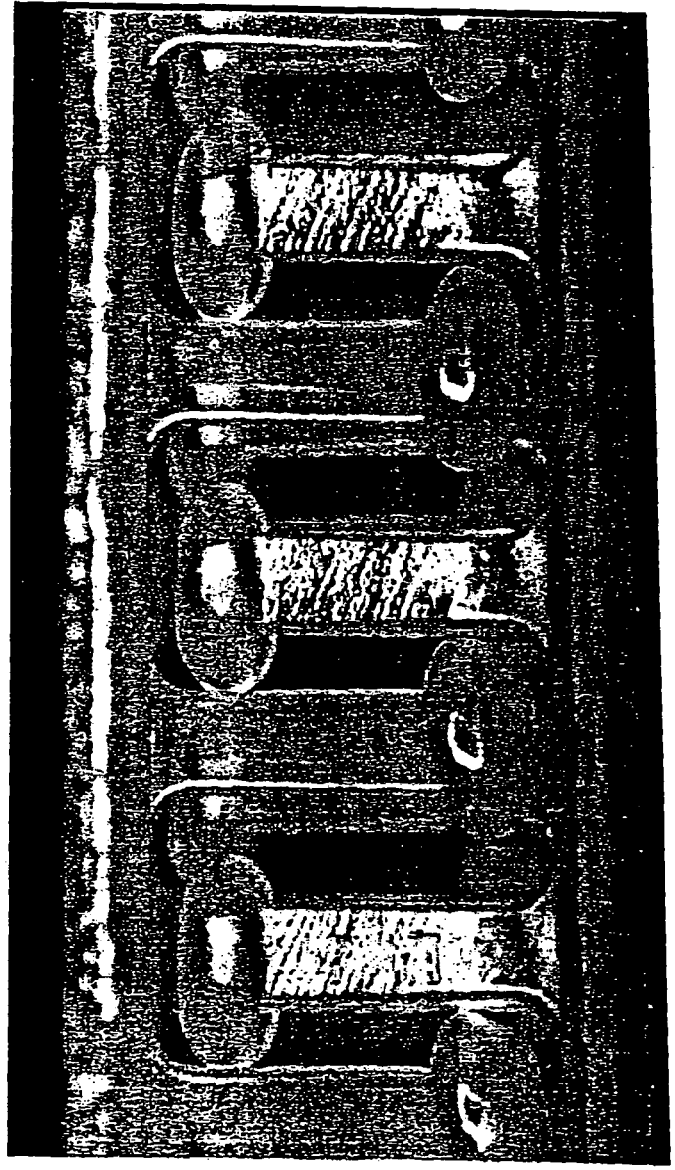
FIG. 29B
FIG. 29D

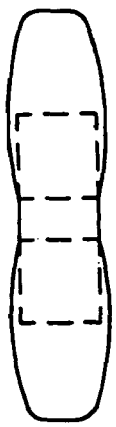
FIG. 35E
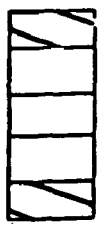
FIG. 35B
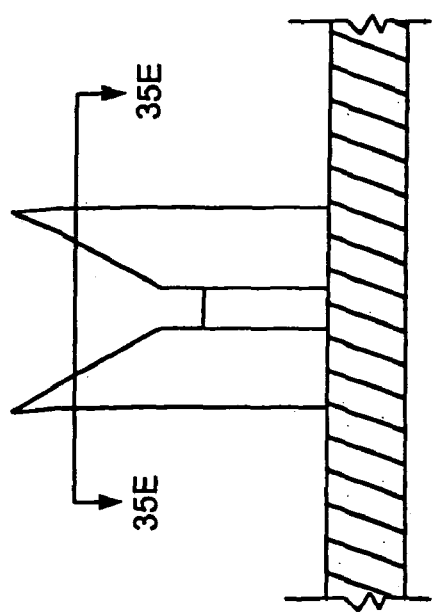
FIG. 35D
FIG. 35A
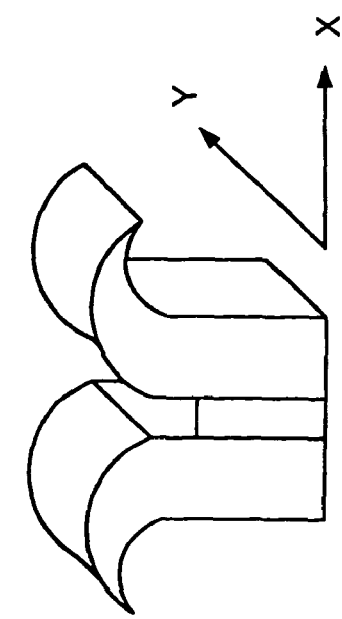
FIG. 35
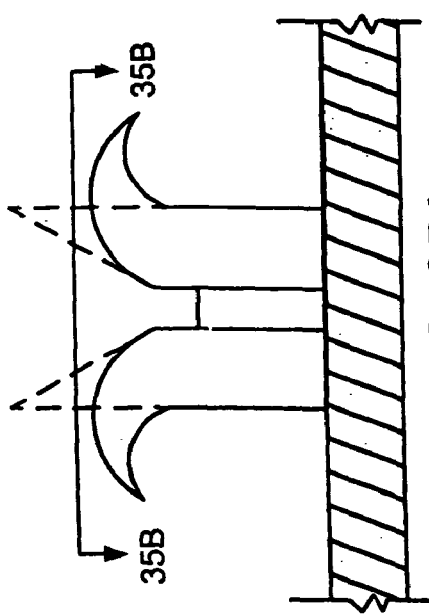
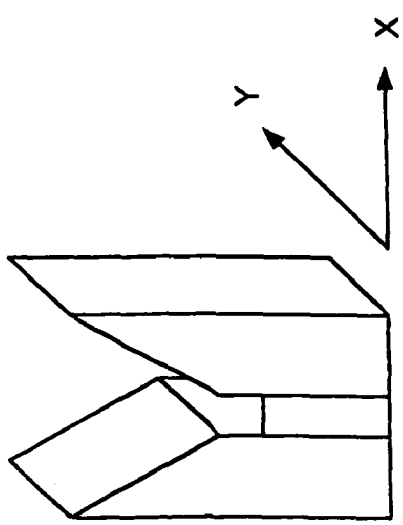
FIG. 35C

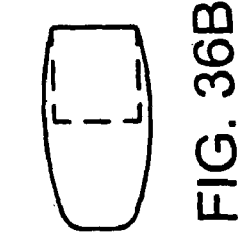
FIG. 36E
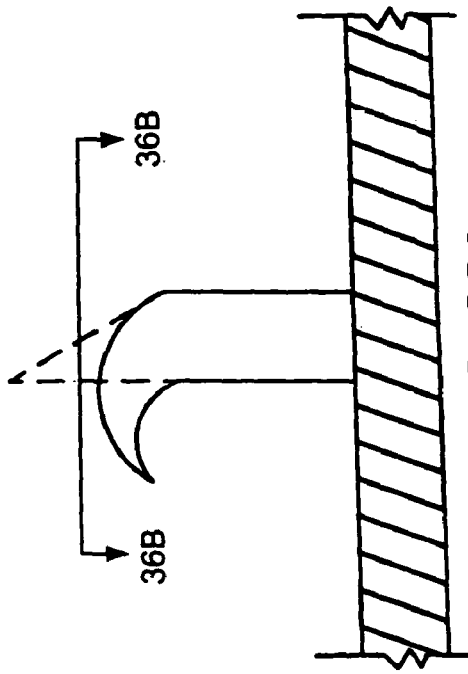
FIG. 36B
FIG. 36D
FIG. 36A
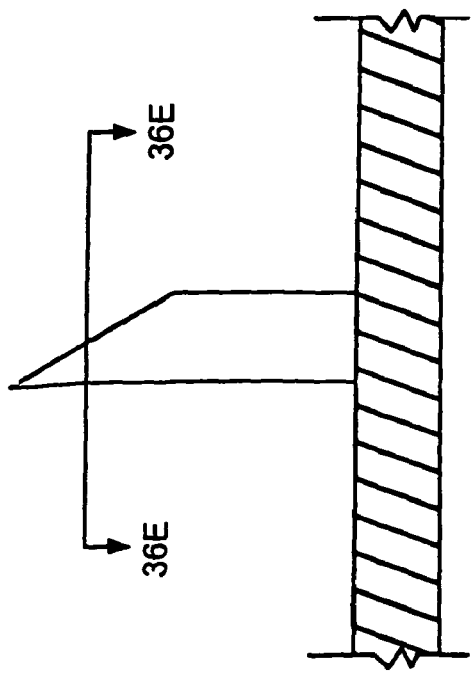
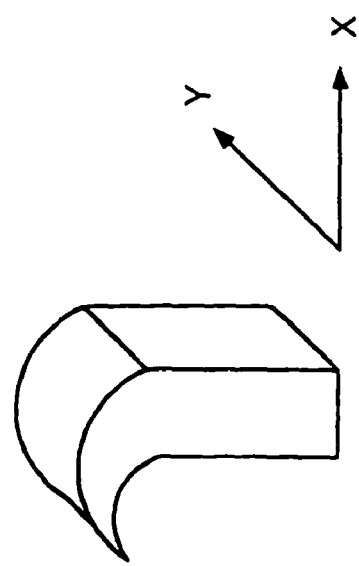
FIG. 36
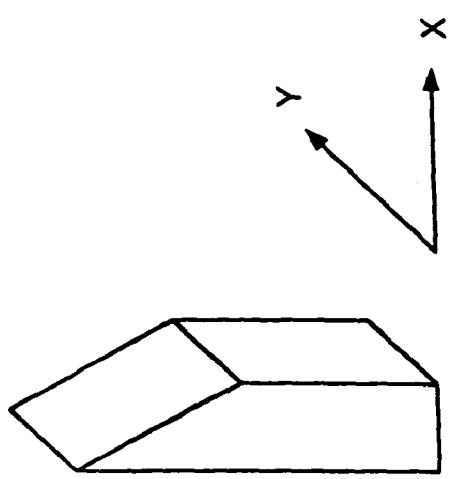
FIG. 36C $\dfrac{\text{chord AB}}{h} \approx 4$ $\dfrac{\text{chord AB}}{h} \cong 4$ $\dfrac{\text{chord AB}}{h} \approx 2$ $\dfrac{\text{chord AB}}{h} \approx 2\tfrac{1}{2}$ $\dfrac{\text{chord AB}}{h} < 2$

METHODS OF MAKING FASTENER PRODUCTS

This application is a divisional of U.S. Ser. No. 10/163,169, filed Jun. 4, 2002 now U.S. Pat. No. 6,991,843, which is a continuation in part of U.S. Ser. No. 09/870,063, filed May 30, 2001 now U.S. Pat. No. 6,708,378, which is a divisional of U.S. Ser. No. 09/231,134, filed Jan. 15, 1999, now U.S. Pat. No. 6,248,276. U.S. Ser. No. 10/163,169 is also a continuation in part of U.S. Ser. No. 09/808,395, filed Mar. 14, 2001 now U.S. Pat. No. 7,048,818, and claims priority from U.S. Provisional Application Ser. No. 60/295,937, filed Jun. 4, 2001. The entire contents of each of the foregoing are hereby incorporated by reference.

TECHNICAL FIELD

This invention relates to touch fasteners commonly known as hook and loop fasteners and to self-engaging fasteners. In many aspects it deals with the particular case in which hooks engage flexible loops such as are formed of fibers of thin nonwoven materials and the like.

BACKGROUND

The present invention relates to male fastener components that engage in openings of a female component, in particular to loops formed by fibers of a nonwoven female component. The invention more particularly relates to stem and head formations of the male elements that promote loop engageability and to methods and machines for their manufacture, and their use. In other aspects the invention relates to manufacture of male fastener members per se, with application for instance to so-called self-engaging fasteners as well as to hook and loop fasteners. The invention in some respects, also relates to specific products of which the following is one example.

Attachment strips for window screens have been formed of, among other things, the male component of a hook and loop type fastener. To secure the screen, the male fastener elements are inserted through the openings of the mesh material and engage the sides of the mesh openings. It is desirable that the engagement between the male fastener elements and the mesh openings provide good peel strength, so that the screen is not detached by wind, and that the attachment strip be inexpensive and relatively attractive.

There is a general need for male fastener components for hook and loop fasteners that provide good peel and shear strength properties in desired single or multiple directions that are relatively inexpensive to manufacture, and a specific need for male fastener components that can function with low cost nonwoven loop materials.

There is also a need to be able to produce male fastener products having differing functional characteristics consistently and efficiently, using techniques that require limited changeover in basic tooling, yet allow for adjustments to produce the desired fastener characteristics.

Furthermore, it is especially desirable to extend the use of hook and loop fastening systems into fields of low cost products and still obtain good fastening performance. Examples include mid- and lowest-cost disposable diapers and sanitary products, disposable packaging for low price products, and disposable lowest cost surgical and industrial clothing and wraps. There are many other recognized low-cost product areas to which such fasteners would be applicable.

In particular it is desirable to obtain good engagement of the male member of the fastening system with low cost nonwoven loop products, which are characterized by their thinness and the low height to which their loop-defining fibers extend.

"Good engagement" in some instances means engaging a large percentage of hooks with low-lying loops.

"Good engagement" in other applications often requires more, as in the case of fasteners for diapers. In such instances the hook component must exhibit strong "peel" resistance when engaged with thin, low cost loop materials. With such materials, effective loop height does not permit transition of loading from the hook head to the hook stem during peeling action, as does occur with expensive loop products that have higher loop height. For this reason there are special problems to be addressed with hooks for thin loop structures in addition to the need to reduce the cost of the hook component.

To explain the peel considerations more fully, in a hook and loop type fastener, "peel strength" is the resistance to stripping of one component from the other when a force normal to their mating surfaces is applied to the extremity of one of the components. Such peeling force on the component causes it to flex and progressively peel from the other. It is desirable to have such peel strength in a hook and loop fastener that ensures that the closure does not release under normal forces of use but still permits the components to be separated when required.

When the loop element is thin, as is usually the case for low-cost female fasteners, the structure of individual loops is very short and low-lying. In this condition, with application of a peel force, the loop exerts a force on the hook, which is essentially perpendicular to the sheet-form base and parallel to the stem of the individual hooks. Consequently the force is applied only to the heads of the hooks.

In contrast, when the loop element has a thick pile structure comprised of long individual loops, a loop must first be pulled out to its full length before it can exert a significant force on a hook. As this occurs, the base webs to which the hooks and loops are attached are enabled to flex away from each other (see FIG. 23Y) so that at the point of separation of hooks from such loops, the mated components are no longer face to face. Therefore the angle at which a loop exerts its force on a hook is less than perpendicular. The longer the loop length, the more that angle diminishes. As a result, with a long loop component, the force not only acts on the head of the hook, but also on its stem. For very long loops, most of the resistance force is on the stem during peeling action.

The consequence is that for short loops, the hook head must be strong and provide much of the resistance to peel separation, while for long loops, a short rigid stem with a slight head overhang is sufficient to give high resistance to peel separation. Therefore, in many instances, in order to expand and improve the use of thin and inexpensive loop components, the hook head geometry must be improved to increase strength of engagement and produce an acceptable closure.

In many cases it is desirable to form the male hook members for use with short loop material by molding an array of stems integrally (i.e. monolithically) with a common base, and subsequently to post-treat the stems by a pressed formation step to form loop-engageable heads. In many instances it is desired to use continuous processes that act in a given machine direction, but to find a way to do this so as to achieve a hook product that has good peel strength characteristics when the user applies peel forces at a substantial angle to the machine direction, and in many cases at right angles, e.g., in the cross-machine direction.

SUMMARY OF THE INVENTION

In many aspects, the present invention employs a method of forming a fastener that includes: (a) forming, from a thermoformable material, a preform product having a sheet-form base and an array of preform stems and upper structures integrally molded with and extending from the base to corresponding terminal ends; (b) heating the terminal ends of the stems or structure provided above the stems to a predetermined softening temperature, while maintaining the sheet-form base and a lower portion of each stem at a temperature lower than the softening temperature; and (c) contacting the terminal ends with a contact surface that is at a predetermined forming temperature, to reform the terminal ends to form heads therefrom that overhang the sheet-form base sufficiently to engage loops, the geometry and material of the preform structure and the condition of reforming the terminal ends of the structure being so related that the formed heads are capable of peel-resistant engagement with loops formed by fibers of thin or ultrathin nonwoven fabrics.

Preferred methods of this aspect of the invention include one or more of the following features. The heating is performed by a non-contact heat source, preferably a convective heat source as by combustion products of a flame. The polymer of the stem or structure is unoriented and is melted into a ball-like configuration. The forming temperature is sufficiently low or other conditions are provided so that the thermoformable material does not adhere to the contact surface. Water of combustion or steam is introduced to the contact surfaces as a non-adhering agent. The forming temperature is lower than the softening temperature. The contact surface comprises the cylindrical surface of a roll. The contact surface is cooled to maintain the forming temperature during step (c). In step (c), the heads that are formed are substantially disc-shaped or mushroom-shaped. The thickness of each disc-shaped head is from about 5 to 15% of the equivalent diameter of the disc, or, in the special case of convective heating of the sides of the terminal structure as well as the ends, as by hot combustion products, up to about 35% of the equivalent diameter of the disc. The head has a substantially dome-shaped surface overhanging the base. Step (a) includes molding the stems in molding cavities in a mold roll. In step (b), the region extends from the terminal end towards the base a distance equal to from about 15 to 25% of the total distance from the terminal end to the base, or, in the special case of the convection heating mentioned, up to about 30% of that distance. The contact surface has a surface finish selected from the group consisting of dimpled, smooth, textured, and combinations thereof. The surface finish comprises dimples or other formations that are small relative to the size of the disc or head, discrete and separated in both the X and Y directions and the contact surface includes a density of dimples or other formations per unit area of the contact surface that is greater than or equal to the density of stems per unit area of the base and especially for the said small discrete formations for modifying the under-structure of the discs through transformation of displacement through the thickness of the disc, the relatively small discrete formations number between about 3 and 15 per disc or head. During step (c), the dimples are in at least partial registration with the stems.

In other aspects, the present invention employs a method of forming a fastener that includes: (a) forming a plurality of stems extending from a common base to a terminal end structure from a thermoformable material; (b) heating a region of the terminal end structure to a predetermined softening temperature, to soften the material in the region, while maintaining the remaining portion of the stems at a temperature lower than the softening temperature; and (c) contacting the terminal ends with a contact surface to form heads at the terminal end of the stems, at least a portion of the contact surface having a sufficiently rough texture to impart a loop-engaging surface roughness to at least a portion of the heads.

Preferred methods include one or more of the following features. The contact surface comprises the cylindrical surface of a roll. The contact surface has a sandpaper-like texture. The contact surface has a surface roughness (rugosity) of about 10 to 200 microns. The contact surface defines a plurality of dimples. The contact surface includes a density of dimples per unit area of the contact surface that is greater than or equal to the density of stems per unit area of the base. The surface roughness imparted to the heads is sufficient to increase the peel strength of the fastener by from about 10 to 100%. The contact surface is so related to the thickness and nature of the heads being formed that contact with the upper surface of the heads is effective to transmit the effect through the resin thickness of the heads sufficiently to impart a degree of texture or surface roughness to the peripheral edge of the head or the undersurface of the head or both, in regions contacted by loops during hook-to-loop engagement. Preferably, the contact of the conforming surface with the head imparts discrete depressions distributed in X or Y or both directions and numbering in the range between about 3 and 15 depressions per head.

According to some aspects of the invention there is a fastener element including an elongated stem extending and molded integrally with a substantially planar base, and a head disposed at a terminal end of the stem, at least a portion of the head having a rough surface having a sandpaper-like surface texture.

Preferred fastener elements include one or more of the following features. The rough surface has a surface roughness (rugosity) of from about 10 to 200 microns. The rough surface has sufficient surface roughness to increase the peel strength of the fastener by from 10 to 100%. The head is substantially disc-shaped or mushroom-shaped.

According to some aspects of the invention there is an attachment strip for attaching a mesh screen to a surface. The attachment strip includes (a) a substantially planar base; (b) a plurality of elongated stems extending from the base; and (c) a plurality of heads, each head being disposed at a terminal end of one of the stems. According to one aspect of the invention, at least a portion of the heads have a rough surface having a sandpaper-like surface texture.

The term "softening temperature," as used herein, refers to a temperature at which the thermoformable material can be formed by a surface pressed against it and includes the melting temperature as well as lower temperatures at which deformation and flow of the material can occur.

The term "disc-shaped", as used herein, refers to a shape having top and bottom surfaces, at least a portion of the top surface being substantially parallel to a corresponding portion of the bottom surface, and having a thickness that is substantially less than its equivalent diameter. "Equivalent diameter" means (a) for a circular disc, the actual diameter, and (b) for a disc having a non-circular shape, the diameter of a circular disc having the same thickness and surface area as the non-circular disc. When viewed from above, the disc-shape may be substantially circular, irregular in shape but approximately circular, or non-circular, e.g., square or cross-shaped. The disc-shape may be flat, or may have other shapes such as domed, wavy, or pyramidal.

The term "mushroom-shaped", as used herein, refers to any shape having a domed portion, with the exception of a complete sphere.

The phrase "loop-engaging surface roughness", as used herein, means a degree of surface roughness that is sufficient to "catch" on a loop fastener element and provide a partial, momentary engagement therewith.

The term "sandpaper-like", as used herein, means a surface roughness akin to the surface texture of sandpaper.

The fastener elements of the invention have a head geometry that advantageously provides a strong attachment to a female fastener component. The fastener elements are particularly well adapted for use in fastener tapes for attaching an insect screen to a window frame, as the head geometry provides a strong engagement with the mesh of the insect screen. Insect screen fastener tapes of the invention exhibit good peel strength and thus good resistance to detachment due to wind. The methods of the invention allow the fastener elements to be manufactured using a relatively simple and economical process.

Other and very important aspects of the present invention go beyond window screening to provide male fastener elements capable of improved engagement with loops formed by fibers of thin nonwoven materials, or with other open structures.

In one aspect of the invention, a method of forming a loop-engaging touch fastener product includes forming, from a thermoformable material, a preform product having a sheet form base and an array of preform stem formations integral with and extending from the base to corresponding terminal ends, each of the stem formations including a first portion joined to the base and a terminal second portion extending from the first portion to a terminal end, there being a discrete transition to a lesser cross-sectional area in the second portion relative to the first portion according to cross-sections taken parallel to the sheet-form base; and deforming substantially all of the second portions of at least some of the stem formations to form, for each portion so deformed, an opening-engaging feature, especially a loop-engageable feature, overhanging the sheet-form base sheet while leaving the first portion substantially as-molded.

Preferred methods include one or more of the following features. The discrete transition begins at a distance from the sheet-form base at least half way to the terminal end of the stem formation. The discrete transition includes a substantial decrease in the cross-sectional area of the second portion relative to the first portion of the stem formation.

In another aspect, the invention provides a hook fastener preform product for subsequent formation of a loop-engaging hook fastener product, the preform product including a base sheet having a surface of thermoplastic resin; and a plurality of stem formations formed integrally (i.e., monolithically) with the surface of the base to protrude therefrom. Each of the protruding formations includes a first, stem portion intersecting the surface and a second portion extending from the first portion to a distal end, to define a height of the formation relative to the surface. An intersection of the first and second portions occurs at a distance from the surface equal to at least half the height of the formation, the intersection defining a discrete transition in structure of the formation, wherein the second portion is selected to improve the formation of the head or disc of the fastener, e.g., to be more susceptible to deformation energy than the stem portion, for instance being reduced in mass to form a disc or head of reduced thickness, or to be more easily pre-conditioned for being formed into a head, or to be formable into a head structure that has improved loop engagement properties, especially resistance to peel when engaged with loops formed by short or low lying fibers of a thin nonwoven loop material. Variations of this aspect of the invention may include an area of any cross-section of the second portion taken parallel to the surface being less than an area of any cross-section of the stem portion taken parallel to the surface, or outermost (i.e., distal) cross-sections having area less than half, or preferably less than one fourth or less of the area of the first, stem portion.

In another aspect, the invention provides a hook fastener preform product for subsequent formation of a loop engaging hook fastener product, the preform product including a base sheet having a continuous length, a width and a surface of thermoplastic resin; and a plurality of stem formations formed integrally with the surface to protrude therefrom, each of the protruding formations including a first, stem portion intersecting the surface and a second portion extending from the first portion to a central peak to define a height of the formation relative to the surface, wherein longitudinal edges of the second portion are tapered relative to longitudinal edges of the first stem portion toward the central peak. Variations of this aspect of the invention may include each stem formation having lateral edges that taper from the first portion continuously to the terminal end of the protruding formation, a stem having an "M" shape or an "A" frame house configuration being examples, only.

In another aspect, the invention provides a hook fastener preform product for subsequent formation of a loop-engaging hook fastener product, the preform product including a base sheet having a continuous length, a width and a surface of thermoplastic resin; and a plurality of stem formations formed integrally with the surface to protrude therefrom, each of the protruding formations including a first stem portion intersecting the surface and a second portion extending from the first portion to define a height of the protruding formation relative to the surface, wherein the second portion comprises a first peak along a first longitudinal edge, a second peak along a second longitudinal edge and a central valley devoid of resin therebetween.

Variations of this aspect of the invention may include each protruding formation, e.g. in the form of a thin fin, having opposite lateral edges that taper continuously from the first portion to the terminal end of the formation, for instance, to describe the configuration of the letter "M." In another case the preform product comprises effectively, one half of the foregoing geometry, i.e., a peak is located at a first longitudinal edge of this fin and a relatively low region is at the opposite longitudinal edge. In preferred embodiments of this aspect, the protruding formation has an "M" or an half "M" shape in which the height of the formation decreases linearly from the one or both peaks to the lowest part of the top of the structure.

In another aspect, the invention provides a hook fastener preform product for subsequent formation of a loop engaging hook fastener product, the preform product including a base sheet having a continuous length, a width and a surface of thermoplastic resin; and a plurality of stem formations formed integrally with the surface to protrude therefrom, each of the stem formations including a first stem portion intersecting the surface and a second portion extending from the first portion to define a height of the protruding formation relative to the surface, wherein the first portion comprises a first cylindrical shape of a first diameter, and the second portion comprises a second cylindrical shape of a second diameter, the second diameter being smaller than the first diameter. Variations of this aspect of the invention may include the second portion being concentric with the first portion.

In the foregoing references to "second portion," it will be understood that the second portion may itself be formed of multiple portions.

According to another aspect of the invention, a new way to manufacture hook products for these and other purposes is achieved by selection of forming conditions to form heads on pre-molded stems or protruding structures, that provide a localized molten mass of the hook resin such that the action of surface tension on the molten mass causes the mass to so overhang a cross-machine extremity of the distal end of the stem, that, when deformed by a conforming surface, such as that of a forming roll, the molten resin is formed into a generally flattened, thin head at a cross-machine extremity of the stem. In preferred embodiments, non-contact heating action melts the distal ends of the preformed structures, and the forming surface is maintained at a lower temperature than that of the molten resin. Also in preferred embodiments, the surface of the forming roll carries molding formations that produce irregular edges or contours to the heads being formed that promote engagement and holding of fiber loops after engagement.

According to another aspect of the invention, a method of manufacturing a hook component for a hook and loop fastener is provided comprising (a) providing a continuous length of a preform stem component of thermoformable resin, the component having a base layer from which extend a plurality of preformed stems with thermoformable extremities of predetermined geometry, the stem component having a machine direction, (b) heating said deformable extremities of said stems to provide on each a localized molten mass of resin which, under action of surface tension, so resides on the respective stem as to overhang a cross-machine extremity of the stem, and (c) deforming the molten mass with a forming surface in manner to produce a generally flattened, thin head at the cross-machine extremity of the stem, (d) steps (a), (b) and (c) being so conducted as to produce a loop engageable head defining, in a plan view, a general contour having a peripheral arc AB parallel to the base of the preform component, the head having an overhang aspect ratio OAR, defined as the ratio of the chord of the arc AB and the height "h" of the line perpendicular to said chord lying at the furthest point of the arc from the chord, OAR=AB/h, where the chord of the arc lies in the plane which defines the cross-machine extremity of the stem and is parallel to said machine direction, the chord lying in or being tangent to the surface of said stem that defines the cross-machine extremity of the stem, said aspect ratio OAR being less than 3.5, preferably about 2.

According to another aspect of the invention, a hook component for a hook and loop fastener is provided comprising a base layer from which extend a plurality of stems having respective loop-engageable heads, at least some of the heads each having a general contour, in plan view, that has a peripheral arc AB parallel to the base, the head having an overhang aspect ratio OAR, defined as the ratio of the chord of the arc AB and the height "h" of the line perpendicular to said chord lying at the furthest point of the arc from the chord, OAR=AB/h, where the chord of the arc lies in the plane which defines the cross-machine extremity of the stem and is parallel to said machine direction, the chord lying in or being tangent to the surface of said stem that defines the cross-machine extremity of the stem, said aspect ratio OAR being less than 3.5, preferably about 2.

The foregoing method or the hook component may have one or more of the following features.

The head has a vertical head thickness, down to its loop engaging region, of no more than about 0.015 inch.

The combined height of each stem and its respective head, measured from the base layer, is no more than about 0.055 inch.

The footprint area of each head is no more than about $4.30 \times 10^{-4}$ square inch.

The stem preform comprises a thin fin projecting from said base, said thin fin having a cross-machine component of orientation of at least about 45 degrees, the fin characterized by a length from the cross-machine extremity of the projection, along the length of the projection, that is greater than about twice the thickness of the fin, the length and thickness being measured at right angles in a plane parallel to the plane of the base of the hook component.

Another aspect of the invention is a hook component for a hook and loop fastener comprising a base layer from which extend a plurality of stems having respective loop-engageable heads, the heads overhanging a cross-machine extremity of the respective stems, the component having a machine direction, the stem comprising a thin fin projecting from said base, said thin fin having a cross-machine component of orientation of at least about 45 degrees, the fin characterized by a length from the cross-machine extremity of the projection, along the length of the projection, that is greater than about twice the thickness of the fin, the length and thickness being measured at right angles in a plane parallel to the plane of the base of the hook component.

Methods or products featuring the thin fin may have one or more of the following features.

The length of the fin is at least 2½ times its thickness.

The length of the thin fin extends in the cross-machine direction.

The stem preform, or the stem, as the case may be, is double-ended, there being a said length of thin fin extending inwardly in opposite directions from cross-machine extremities on opposite ends of the stem preform or stem.

According to other aspects of the invention, it is further found that important special geometries of molded preform elements, and selected techniques of head forming, are effective in achieving important advantages in this context, and more generally.

According to one particularly important aspect of the invention, the molded stem preform comprises a thin fin projection having a significant cross-machine component of orientation, the thin fin characterized by a length from the cross-machine extremity of the projection, along the length of the projection, that is greater than about twice the length and thickness being measured at right angles in a plane parallel to the plane of the base of the hook component, preferably, such length being in the range of about 2½ times such thickness, to less than 3 times such thickness.

Maximum length of the fins is not dictated by melted configuration considerations.

Preferred aspects of this aspect have one or more of the following features.

A stem preform is double-ended, in that there is such a length of thin fin extending inwardly in opposite directions from cross-machine extremities on opposite ends of the preform member. The stem preform has a stiffening feature that serves to stiffen the preform from columnar collapse during application of postforming force. In certain preferred embodiments the stiffening feature has a height that is less than that of the thin fin, such that, in some embodiments, it is not reformed during the post-forming action, or, in other embodiments, is not reformed to the degree to which the cross-machine extremity of the thin fin is reformed. In other embodiments, the strengthening projection itself comprises a thin fin having a length greater than about twice its thickness, or more, measured in the same manner as above, and preferably has the other preferred attributes of thin fins mentioned above. In certain preferred embodiments, the stem has multiple thin fins, for instance it is of cross or plus sign form, having four projections from a central region, or it can have, e.g., three or five projections, each having the described thin fin form. In some cases the pairs of oppositely extending fins are aligned with the cross-machine and machine directions, while in other embodiments all projections form acute angles with those directions.

Another important feature of the invention is a thin fin stem preform as described which has its direction of elongation set at an acute angle to the machine direction, for instance 30 or 45 degrees, but has an end surface at its cross-machine extremity that is generally aligned with the machine direction. In certain preferred embodiments this cross-machine extremity is defined by a planar end face that is perpendicular to the base of the hook component and aligned with the machine direction, preferably this fin-shaped preform element having long sides that are generally of planar, parallel form, the preform terminating at one corner at the cross-machine extremity with a horizontal profile included angle of substantially less than 90 degrees, for instance 45 degrees. In certain preferred embodiments, the horizontal cross-section of the entire stem is of parallelogram form, in which each cross-machine extremity of the profile ends in a stem portion defining an included angle of substantially less than 90 degrees, e.g. as little as 45 degrees. In another embodiment, the profile of the stem is defined as two thin fins of such profile, set at substantial angles to each other, e.g. at 90 degrees, to form a cross of the two parallelograms. In other cases an X, Y array of such preform elements includes bands in which the parallelogram profiles have a first orientation and bands, preferably bands alternating with the first-mentioned bands, having the opposite or mirror image orientation.

Another aspect of the invention employs a thin fin preform element, which, at least in the cross machine direction, has the profile of an "M" with vertically straight sides at the cross-machine extremities, and, effectively a "V"-shaped cut out in its central region that is devoid of resin, so that the outermost portions of the preform element are tapered from an outward point to horizontal cross sections of increasing area moving toward the base. With this form, as melting progresses, as when heated by a non-contact heat source, the molten resin preferentially flows over the edge of the straight side to form a molten mass overhang at the cross-machine extremity. This mass later is formed to provide the desired loop-engaging shape.

In preferred embodiments of these aspects: non-contact heating is accomplished principally by convection heating, preferably by the hot gaseous combustion products of a close-approaching gas flame; the forming surface that engages the molten surface has a molding surface that imparts a degree of roughness or shaped profile to the outer surface at the peripheral edges of the head that is formed, of size and shape enabling telegraph of the disturbance through the mass of the overhanging portion to provide a degree of irregularity, texture or roughness on loop-engaging surfaces of the overhanging head, for instance the peripheral edges of the head's under-surfaces, that promote retention of the loop on the hook under peel conditions.

Other aspects of the invention comprise hook manufacture employing stem preform products of the geometries described, employing non-contact heating, enabling formation of advantageously sized and/or located rounded masses of molten resin, followed by engagement of the masses with a forming surface.

In preferred embodiments a step is employed to prevent sticking or adherence of the formed head to the forming surface during disengagement. Embodiments of the invention include maintaining the forming surface cooler than the ambient boiling or condensation temperature of water and introducing water or steam to that surface. In one important embodiment, the mode of non-contact heating is by immersing the terminal end portions of the formations in the flow of hot combustion products of a close-approaching gas flame in such manner that water of combustion condenses on the cooled forming roll and performs an anti-adhesion function.

Another aspect of the invention involves "superheating" a preform element by a non-contact heat source in advance of press-forming the heated resin mass with a relatively cool forming surface, such that, following such press forming, under the influence of gravity and/or surface tension, further forming movement of the resin occurs before stabilizing, e.g. to form a self-engaging male fastener formation, as in the case of mushroom formations, or a loop engaging structure, as in the case of heads with a "J" profile.

In preferred embodiments the amount of such "superheating" in relation to heat loss at the forming surface, which is preferably a cooled roll, ensures that the retained heat maintains the resin sufficiently heated to enable the mass to flow into the form of a mushroom, or in other embodiments, is sufficient to enable peripheral portions of the formed mass to droop or self-deform to form a "J" like profile, before solidifying.

In preferred embodiments of this feature the resin for thus forming a mushroom structure following press-formation is low density polyethylene or other resin having a low heat-deflection temperature, and for so forming a "J" like profile, the resin is high density polyethylene or nylon or resins of similar higher heat deflection temperatures.

Another important aspect of the invention is the realization that the property of molecular orientation of the resin of preformed stems intended for subsequent heat forming, contrary to thought of others is not a necessity and indeed can advantageously be avoided with desirable effects. It is realized that pre-heating a non-oriented resin projection enables a mass of molten resin to form as a ball, dependent on the size and shape of the resin formation melted, and that the physical location of this ball can be advantageously selected and controlled by pre-design of the protruding structure, so that a subsequent press forming (i.e. flat-topping) of the molten resin can distribute the resin to a desired final shape; or a desired distribution geometry, in the case of super-heated resin, such that gravity and/or residual surface tension effects accomplish a further desired deformation. In certain situations, further cooling, or even further surface pressing can be employed for determining the final shape.

In preferred embodiments, the sequence is preheating to super-heat condition by convection, preferably by immersion in combustion products of a gas flame, flat-topping with a cooled roll to produce a desired areal distribution of the resin, and allowing the elements to further form from the distributed shape by action of gravity and surface tension. This is followed by air cooling or engagement with a further cooled roll. In some cases, at this point, the product may be engaged by a heated roll to finalize the conformation or surface texture of the product.

Another aspect of the invention concerns convection heating of preform elements, employing a distributed gas flame. The luminescent flame is positioned to immerse side surface of terminal portions of the preform elements as well as the end surfaces, in hot combustion products of the gas flame, at temperature of the order of 1000° C., to achieve rapid heating of the elements and enable the elements to proceed at high production rate through the subsequent press forming (or "flat-topping") stage.

In preferred embodiments the press forming surface is maintained at a temperature below condensation temperature of water, in preferred cases in the range of between about 5° and 60° C., preferably 10° and 45° C. and most preferably of about 25° and 30° C., and the surface is exposed to the combustion products of the flame to cause condensation of water over the forming surface in quantity to enhance release of the resin from the forming surface after the forming action. Preferably the forming surface is a chilled conforming or pressing roll.

In the case of using a heated pressing roll following preheating with convection heating as described, anti-adhering material is provided at the interface between the forming surface and the resin. In preferred embodiments the material comprises a Teflon or other anti-stick coating of the forming surface, injection of water or steam to the interface, or both. In this manner, the speed of operation of the process may be increased while still using developed tooling that employ hot rolls or other heated forming surfaces.

In yet another aspect of the invention, a method of forming a loop engaging fastener product includes providing a preform stem product having a plurality of stems, each of which rises from a base to a distal end and contacting the distal end of at least some of the stems with an ultrasonic horn to form loop engaging heads.

Variations of this aspect of the invention may include one or more of the following features. The ultrasonic horn is rotating while contacting the distal end of at least some of the stems. The preform stem product is introduced between a gap formed by the ultrasonic horn and an anvil and the gap is sized to cause the distal ends of at least some of the stems to contact the rotary horn. The anvil is rotating.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a side view of a fastener including a fastener element according to one embodiment of the invention.

FIG. 2 is a side cross-sectional view of a fastener element according to an alternate embodiment of the invention.

FIGS. 3 and 3A are side cross-sectional views of fastener elements according to other alternate embodiments of the invention.

FIGS. 15A and 15B are side and front views, respectively, of another preform stem formation.

FIGS. 16A, 16B and 16C are side, front and top views, respectively, of a loop engaging fastener element formed from the preform stem formation of FIGS. 15A and 15B.

FIGS. 17A and 17B are side and front views, respectively, of another preform stem formation.

FIGS. 18A, 18B and 18C are side, front and top views, respectively, of a loop engaging fastener element formed from the preform stem formation of FIGS. 17A and 17B.

FIGS. 19A and 19B are side and front views, respectively, of another preform stem formation.

FIGS. 20A, 20B and 20C are side, front and top views, respectively, of a loop engaging fastener element formed from the preform stem formation of FIGS. 19A and 19B.

FIG. 23 is a diagrammatic perspective view of an embodiment of a multi-lobed hook element made according to the invention, while

FIG. 23G' is a side view and FIG. 23G" is a perspective view of a preferred configuration of the machine.

FIGS. 23I and 23J are highly magnified partial cross-sectional views taken parallel to the periphery of respective mold rings for forming the preform element of FIG. 23 while

FIGS. 23S and 23T are views similar to FIGS. 23P and 23Q of a hook formed by a thin fin preform stem while

FIG. 24 is a diagrammatic perspective view of a second embodiment of a single hook element made according to the invention, while

FIG. 24E is a horizontal section view of the preform element taken on line 24E-24E of FIG. 24D.

FIG. 25 is a top view of another embodiment of a single hook made according to the invention, while

FIGS. 26 and 26A are side and top views of another embodiment while

FIGS. 27 and 27A are, respectively, plan and side views of another embodiment, while

In the same respect as embodiments above.

FIGS. 29, 29A, 29B and 29C depict dome shaped mushrooms formed following flat-topping by flow of previously "super heated" polyethylene (FIGS. 29 and 29A referring to use of low density polyethylene) while FIG. 29D illustrates use of two such components as a self-engaging fastener.

FIG. 37 is a diagrammatic perspective view of a further embodiment of a single hook element made according to the invention, while FIG. 37A is a side view of the element and FIG. 37B is a top view taken on lines 37B-37B of FIG. 37A.

FIGS. 37C through 37E are views of a preform element employed in forming the hook element of FIG. 37, FIG. 37C being a diagrammatic perspective view of the molded preform element, FIG. 37D a vertical side view of it and FIG. 37E a horizontal cross-section view of the preform element taken on line 37E-37E of FIG. 37D.

FIGS. 38 and 38A are diagrams showing the relationship of the chord AB at the stem face relative to the disk overhang in the case of square and cylindrical stems, represented by an overhang aspect ratio, while

DESCRIPTION OF THE PREFERRED EMBODIMENTS

Figure 2A:
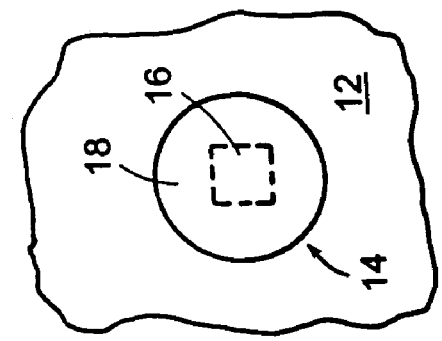
FIGS. 2A and 2B are top views of fastener elements according to alternate embodiments of the invention; these fastener elements have the same cross-sectional shape as that shown in FIG. 2.

Referring to FIG. 1, fastener 10 includes a base 12 and a fastener element 14 extending from the base. (Fastener 10 generally includes an array of fastener elements; a single fastener element is shown for clarity.) Fastener element 14 includes a stem 16 and, at the terminal end of stem 16, a head 18. Head 18 is shaped for engagement with another fastener component, for example a female fastener component having a plurality of loops, a mesh such as an insect screen, or another fastener component similar to fastener 10.

Figure 4:
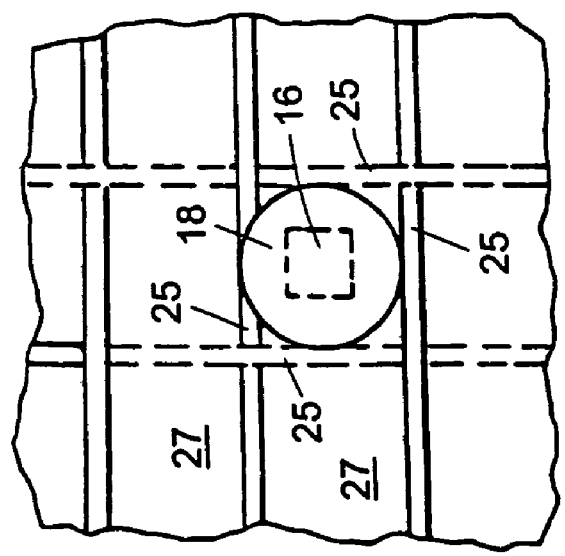
FIG. 4 is a front view showing a fastener element of FIG. 1 or FIG. 2 engaged with the mesh opening of an insect screen.

As shown in FIG. 1, head 18 is substantially disc shaped, including a substantially planar top surface 20, and a substantially planar bottom surface 22 that faces and overhangs base 12. It is desirable that the disc be relatively thin, allowing a cooperating fastener element, e.g., a loop or the wire mesh of a window screen, to penetrate into the disc by flexing the disc material. Preferably, the thickness of the disc is from about 5 to 15% of the equivalent diameter of the disc. If the disc is thinner, it will tend to have reduced cycle life (i.e., durability during repeated engagement and disengagement of the fastener), whereas if the disc is thicker the fastener may exhibit reduced peel strength. As shown in FIG. 1A, head 18 is substantially circular when viewed from above, and stem 16 is substantially circular in radial cross-section, as shown, or square in radial cross-section. (In other embodiments, head 18 can be irregular in shape (FIG. 1B), square (FIG. 1C) or cross-shaped (FIG. 1D) when viewed from above.) The disc shape is particularly advantageous for engagement with a mesh screen (FIG. 4) because the sides 25 of the mesh opening can penetrate into the thin disc. As a result, as shown in FIG. 4, secure engagement can be provided even though the disc is smaller than the mesh opening and only engages one or two sides 25 of the mesh opening. The head 18 is also suitable for engagement with loops or with other similarly shaped heads.

Figure 2B:
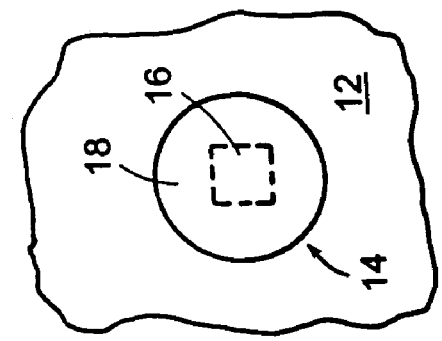
Figure 1C:
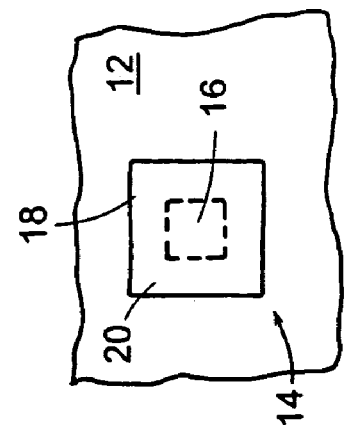
FIGS. 1B, 1C and 1D are top views of fastener elements according to alternate embodiments of the invention; these fastener elements have the same profile, when seen from the side, as that shown in FIG. 1.
Figure 1D:
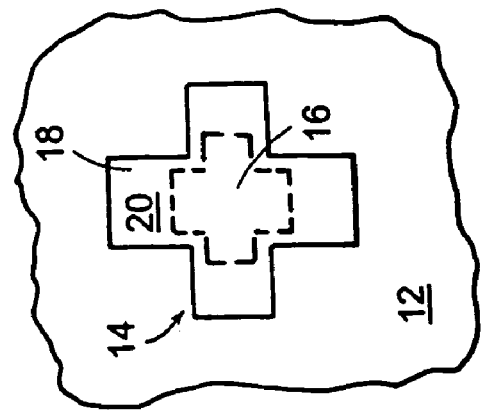
Figure 1A:
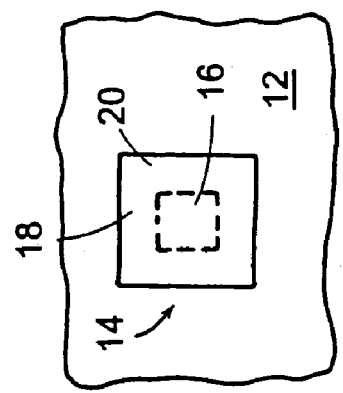
FIG. 1A is a top view of the fastener element, with the stem portion shown in phantom lines.
Figure 1B:
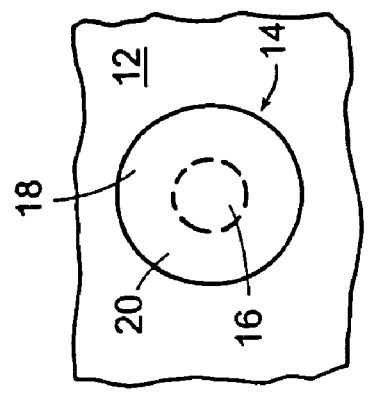

In an alternate embodiment, shown in FIG. 2, head 18 includes a domed portion 24, and a correspondingly dome-shaped lower surface 23, a major portion of which is substantially parallel to domed portion 24. Surface 23 faces and overhangs base 12, providing a surface for engagement with a female fastener element or mesh. Head 18 can have various shapes. For example, head 18 can be a disc that is square or rectangular when viewed from the top (FIG. 2A), with two opposed edges of the disc being bent down to form a U-shaped domed portion. Alternatively, head 18 can be a circular disc that is bent down around its periphery to form a mushroom-like domed portion. These head shapes are particularly advantageous for engagement with a mesh screen (FIG. 4) because the domed portion allows smooth penetration into the mesh openings 27 and the thin disc shape allows sides 25 of the mesh opening to be embedded into surface 23. Head 18 can also be used to engage the loops of a female fastener component, or to self-engage with another fastener having similarly shaped heads.

Figure 3C:
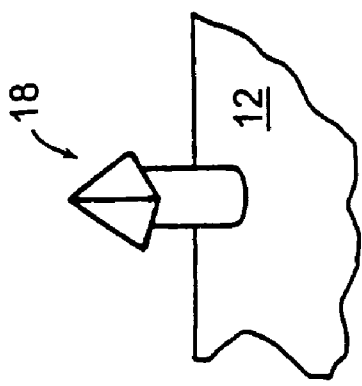
FIGS. 3B and 3C are perspective views of fastener elements according to other alternate embodiments of the invention.
Figure 3B:
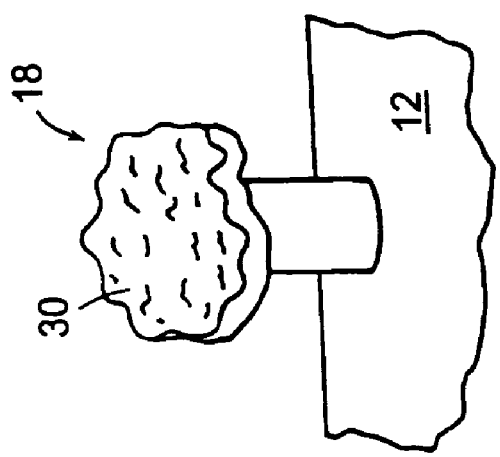

In alternate embodiments, shown in FIGS. 3 and 3A, the disc-shaped heads are "wavy". The head 18 may be S-shaped in cross-section, as shown in FIG. 3, or may be W-shaped, as shown in FIG. 3A. The head shapes shown in these figures may be provided with a rough surface, as described below with reference to FIG. 3B.

In another alternate embodiment, shown in FIG. 3B, head 18 includes a rough, sandpaper-like surface 30. Preferably, the texture of surface 30 resembles that of 320 grain sandpaper (used for sanding metals). The sandpaper-like surface includes protrusions that tend to catch on the fastener component with which the head 18 is engaged (not shown), making it more difficult to inadvertently disengage the mated fastener components. As a result, the strength of engagement is generally increased, relative to the strength obtained from a similar fastener element having a smooth surface. In particular, in preferred embodiments the peel strength, as measured by ASTM D 5170-91 ("T" method), is increased by about 10 to 100%. It is preferred that the surface 30 have a surface roughness (rugosity) of at least 10 microns, more preferably from about 10 to 200 microns.

In another embodiment, shown in FIG. 3C, the head 18 is pyramidal in shape. Preferably, the surface of the head that overhangs the base has the same contour as the upper surface of the head, so that a major portion of the surfaces is substantially parallel.

In all of the embodiments shown in FIGS. 1-3C, the head overhangs the base to a significant extent. Preferably, the surface area A1 of the surface overhanging the base is equal to at least 20% greater than the surface area A2 of the radial cross-section of the stem 16 taken along line A-A, i.e., where the stem intersects the head. The surface area A1 may be up to 600% greater than the surface area A2. For example, for a fastener element in which surface area A2 is 0.03 $mm^2$, surface area A1 is preferably about 0.05 $mm^2$. It is also generally preferred that the amount of overhang be substantially uniform around the perimeter of the stem, to provide a multi-directional engagement. However, for ease of manufacture it will in some cases be preferred that the amount of overhang be non-uniform, as will be discussed below with reference to FIG. 5.

Figure 7A:
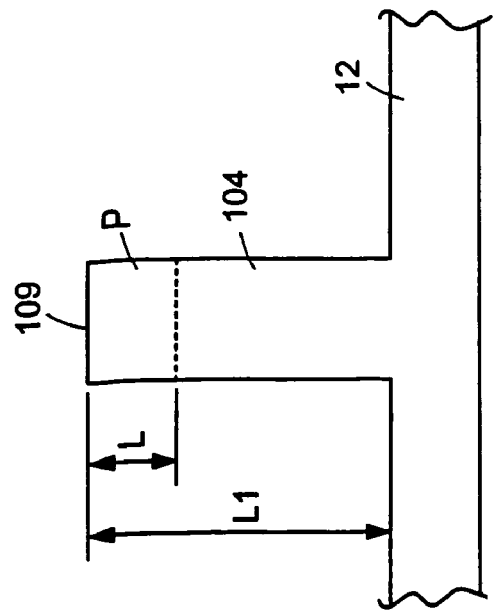
FIG. 7A is a highly enlarged view of one of the stems shown in FIG. 7.
Figure 7C:
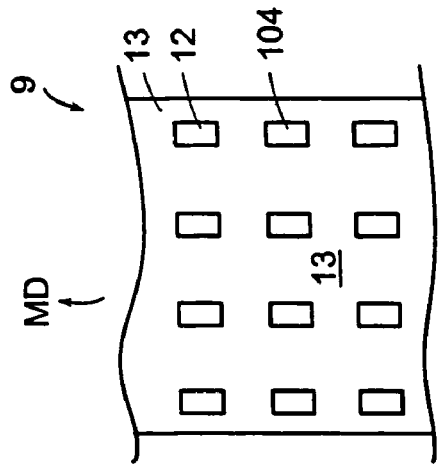
FIG. 7C is a plan view of the preform product comprising an array of the stems proceeding in the machine direction.
Figure 7:
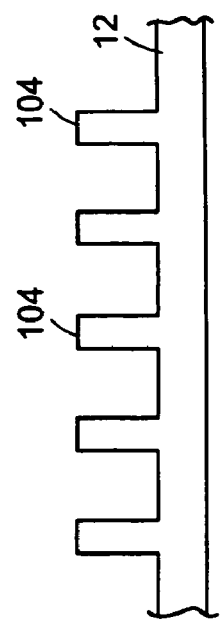
FIG. 7 is an enlarged side detail view of area A in FIG. 6, showing a portion of the stem-carrying base prior to conformation.
Figure 7B:
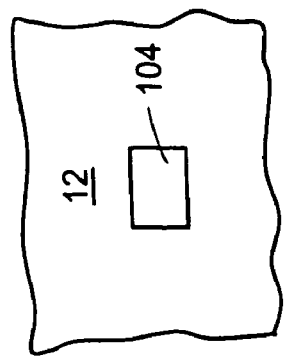
FIG. 7B is a top view of the portion of the base shown in FIG. 7A.

A machine 100 for forming the fastener elements described above is shown in FIG. 5. A supply roll 102, 126 introduces a continuous supply of a stem-carrying base 12 (shown in FIGS. 7-7B) into the machine 100. Stem-carrying base 12 is formed of a thermoformable polymer. In a previous manufacturing step, roll 102 was wound up as the take-up roll at a molding station (not shown) at which stems 104 (FIGS. 7-7B) were integrally molded onto base 12. The molding station may include a mold roll having a plurality of mold cavities provided by aligned plates, e.g., as described, for example, by U.S. Pat. No. 4,794,028, the disclosure of which is incorporated herein by reference, or may utilize any desired stem-molding technique. As shown in FIG. 7B, the stems may be rectangular or square in radial cross-section, if a rectangular or square head is desired, or may be oval, round, cross-shaped, or any other desired shape, for forming similarly shaped heads (see FIGS. 1A-1D).

The supply roll 102 is unwound by drive mechanism 106, which conveys stem-carrying base 12 into optional pre-heating area 108 which raises the temperature of the stem-carrying base 12 to a pre-heat temperature that is above room temperature but much lower than the Vicat temperature of the polymer. This pre-heating allows the tips of the stems to be heated to a predetermined softening temperature more quickly during the next step of the process.

Next, the base 12 moves to heating device 110, which heats a portion of the stems. As indicated in FIG. 7A, only a portion P of the stems 104, adjacent their tips 109, is heated by heating device 110, leaving the remainder of the stem relatively cool and thus relatively rigid. Preferably, the length L of portion P is less than 30% of the total length L1 of the stem, more preferably from about 15% to 25% of L1. Portion P is heated to a softening temperature at which portion P can be formed into a desired head shape, typically a temperature that is greater than or equal to the Vicat temperature of the thermoformable polymer. The remainder of the stem is not heated, and remains at a temperature that is less than the softening temperature S, preferably at least 10% less.

To ensure that only portion P is heated to the softening temperature, it is preferred that heating device 110 include a non-contact heat source 111 (FIG. 6) that is capable of quickly elevating the temperature of material that is very close to the heat source, without raising the temperature of material that is relatively further away from the heat source. Suitable non-contact heat sources include flame heaters, electrically heated nichrome wire, and radiant heater blocks. To heat portion P to the softening temperature without contact, the heat source typically must be at a relatively high temperature. For example, if the softening temperature is from about 100 to 140 C, the temperature of the heat source will generally be from about 300 to 1000 C and the heat source will be positioned from about 0.1 to 30 mm from the tips of the stems.

After portion P of the stems has been heated, the base 12 moves to conformation head 112, at which base 12 passes between conformation roll 114 and drive roll 116. Conformation roll 114 forms the portion P of the stems into a desired head shape, as will be described in further detail below, while drive roll 116 advances base 12 and flattens it against roll 114 to enhance head uniformity. It is preferred that the temperature of conformation roll 114 (the forming temperature) be lower than the softening temperature. Maintaining the conformation roll 114 at this relatively low temperature has been found to allow the conformation roll to flatten the spherical ("ball-shaped") heads that are generally formed during the previous heating step into a desired head shape. Spherical heads are generally undesirable, as such heads tend not to provide secure engagement with a mating fastener. A low forming temperature also prevents adhesion of the thermoformable polymer to the conformation roll. Generally, to obtain the desired forming temperature it is necessary to chill the conformation roll, e.g., by running cold water through a channel 115 in the center of the roll, to counteract heating of the conformation roll by the heat from portion P of the stems. If further cooling is needed to obtain the desired forming temperature, the drive roll may be chilled in a similar manner.

Figure 8:
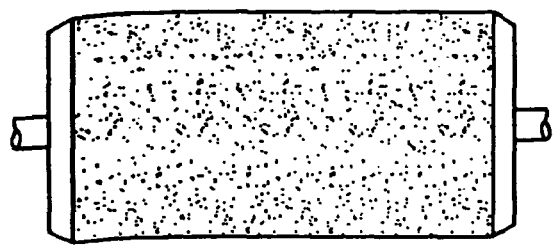
FIGS. 8-8D are side views showing various suitable conformation roll surfaces for forming fastener elements of the invention.
Figure 8A:
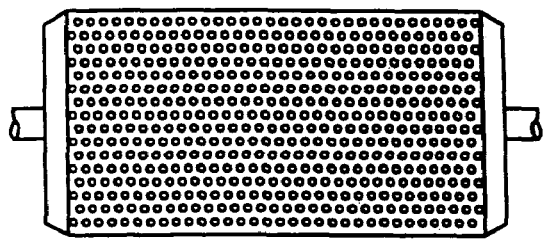
Figure 8B:
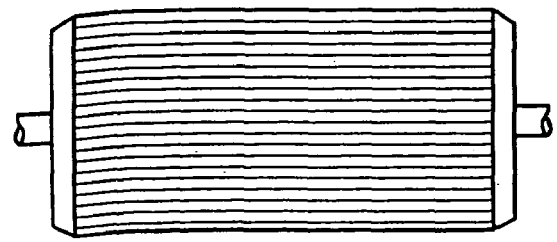
Figure 8C:
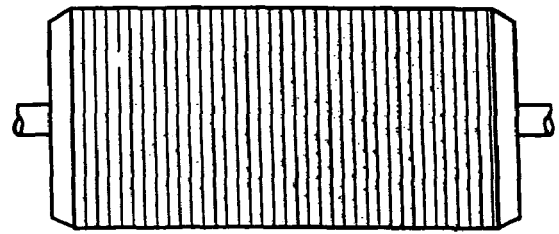
Figure 8D:
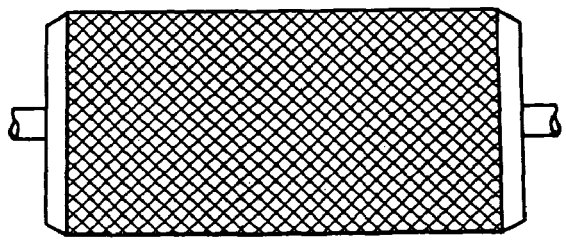

The surface texture of conformation roll 114 will determine the shape of the heads that are formed. If disc-shaped heads having a smooth surface are desired, the surface texture will be smooth and flat. If a sandpaper-like surface is desired, the surface texture of the conformation roll will be sandpaper-like (FIG. 8). If mushroom-shaped (domed) heads are desired, the conformation roll will include a plurality of substantially hemispherical indentations ("dimples") to form the dome portion of the heads (FIG. 8A). Disc-shaped heads having a "wavy" shape, e.g., as shown in FIGS. 3 and 3A, can be formed using the conformation roll surfaces shown in FIGS. 8B and 8C. The diamond-lattice conformation roll surface shown in FIG. 8D will give the head a pyramidal shape, e.g., as shown in FIG. 3C. The conformation roll may also have a soft surface (not shown), e.g., rubber, to provide a mushroom-shaped head.

Preferably, when the surface texture includes dimples, the density of the dimples is substantially uniform over the roll surface, and is greater than or equal to the density of stems on the base 12. To allow for improper registration between the stems and the dimples, it is preferred that the density of the dimples be substantially greater than the density of the stems (if the density is equal, improper registration may result in none of the stems being contacted by dimples).

As discussed above, while the uniformly overhanging, domed head shape shown in FIG. 2 is generally preferred, obtaining this shape may unduly complicate manufacturing, due to the need to maintain substantially complete registration between the dimples and stems. As a result, for ease of manufacturing it may in some cases be desirable to form less uniform head shapes by allowing the dimples and stems to be in partial registration, rather than full registration. In these cases, the conformation roll should have a density of dimples that is significantly higher than the density of stems, to increase the probability of contact between the dimples and stems. In this manner, some of the heads are likely to have the shape shown in FIG. 2, while other heads will have different head shapes resulting from contact of a stem with a portion of a dimple.

The spacing of the conformation roll 114 from the drive roll 116 is selected to deform portion P of the stems to form the desired head shape, without excessive damage to the unheated portion of the stems. It is also preferred that the spacing be sufficiently small so that the drive roll flattens base 12 and provides substantially uniform contact pressure of stem tips 109 against the conformation roll. Preferably, the spacing is approximately equal to the total height of the stem (L1, FIG. 7A) less the length of the heated portion P (L, FIG. 7A).

Next, the base 12 moves to a cooling station 118. Cooling station 118 cools the formed heads, e.g., by cool air, preventing further deformation of the heads. Preferably, the heads are cooled to approximately room temperature. The cooled base is then moved through driving station 520 and wound onto take-up roll 522 by winding element 524.

Alternate supply and take-up rolls 126, 128 are provided so that when supply roll 102 is depleted and/or when take-up roll 524 is filled, the appropriate roll can be easily replaced without disrupting the process.

Suitable materials for use in forming the fastener are thermoplastic polymers that provide the mechanical properties that are desired for a particular application. Preferred polymers include polypropylenes, such as those available from Montell under the tradename MOPLEN, polyethylenes, ABS, polyamides, and polyesters (e.g., PET).

Other embodiments are of course possible.

For example, while disc-shaped heads have been shown and discussed above, the head may have any desired shape that provides a surface overhanging the base to an extent sufficient to provide a multi-directional engagement having desired strength characteristics.

Moreover, while the process described includes only a single heating of the stem tips and a single pass through a conformation head, these steps may be repeated one or more times to provide other head shapes. Subsequent conformation heads may have the same surface as the first conformation head, or may have different surfaces.

In addition, if desired, the stem tips may be cooled after the heating step and immediately before the conformation head, to form a spherical head that is then forced down against the stem, embedding the upper portion of the stem in the head to form a mushroom-shaped head.

Further, in some cases it is not necessary to cool the conformation roll. If the desired head shape can be obtained and resin sticking can be avoided, the conformation roll may be used without either heating or cooling, or may be heated.

As illustrated in FIGS. 7, 7A, 7B and 7C, one example of a preform product 9 for producing a fastener product, has a flexible, yet relatively planar base sheet 12 from which stem formations 104 project. Stem formations 104 are formed integrally, i.e. monolithically from the same thermoplastic resin, e.g., polypropylene, as the surface 13 of base sheet 12 from which they project. As shown in the more detailed views of FIGS. 9A and 9B, each stem formation 104 has front and back edge surfaces 101, 103 that typically taper very slightly (e.g. 1°, not shown), and fairly continuously from broadly radiused intersection surfaces 15 with base surface 13 to a distal end 109 of the stem formation. Side edge surfaces 107 are relatively perpendicular to the base and extend to distal end 109, which is relatively parallel to the base. The slight taper or draft angle of front and back edge surfaces 101, 103 aids in the removal of the stem formations from the mold cavities in which they are formed.

Figure 9A:
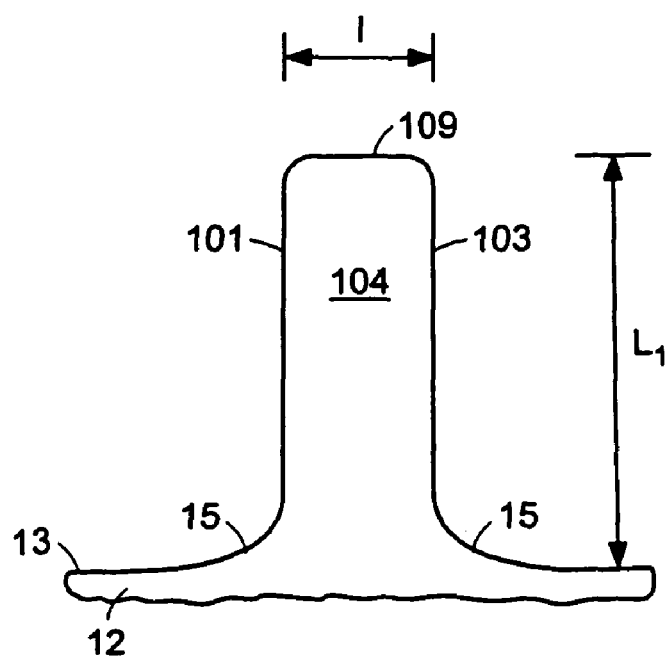
FIGS. 9A and 9B are further magnified side and front views, respectively, of an individual stem formation of the preform stem product of FIGS. 7-7C.
Figure 9B:
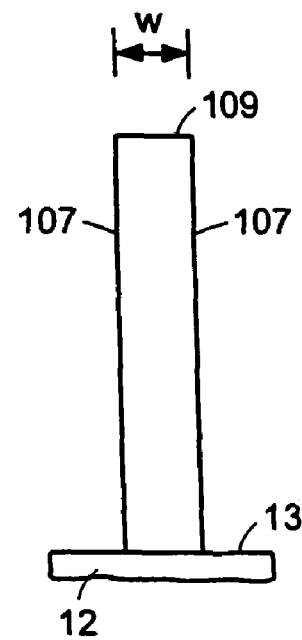

In the example of FIGS. 9A, 9B, the stem formations have an overall height, $L_1$, from base surface 13 to distal end 109, a constant width, w, between the side surfaces 107 and a length, 1, as measured between the top of the tapered front and back surfaces.

In one example, dimensions w and 1 are equal, e.g. 0.008 inch, to provide a stem of square cross-sectional profile, in which case the height $L_1$ may be e.g. 0.027 in.

Figure 10A:
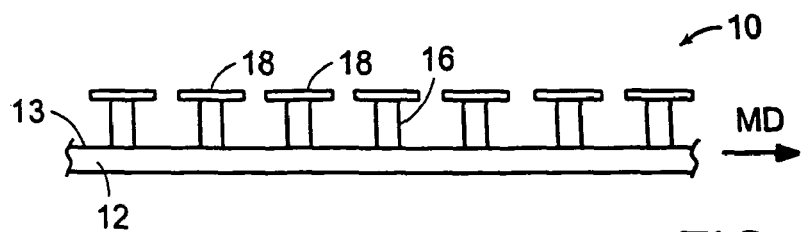
FIGS. 10A, 10B and 10C are unscaled, magnified side, front and top views of a loop engaging fastener product formed from the preform stem product of FIGS. 7-7C.
Figure 10B:
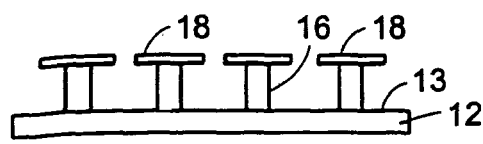
Figure 10C:
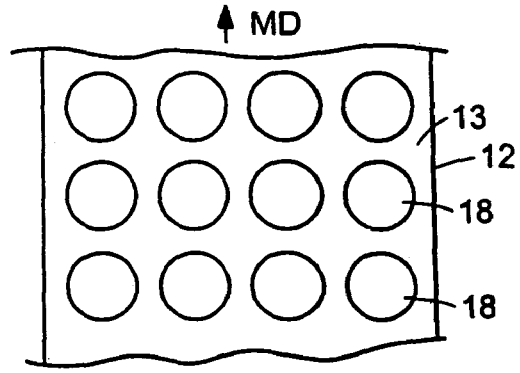

Referring now to FIGS. 10A-10C, the preform product can be formed, as further described below, into a fastener product 10 having the same base sheet 12 and surface 13, but with the tips of the stem formations flattened relative to the base to form loop engageable heads 18. Each engageable head 18 is generally disc-shaped and extends outward from its respective stem portion 16 to overhang and oppose base surface 13. As illustrated more clearly in FIGS. 11A-11L, discs 18 are slightly oval-shaped, having a major diameter J, in the example, of the order of 0.017 inches, extending in the direction corresponding to the side surfaces 107 of stem portion 16 and a minor diameter N, of the order of 0.015 inches, extending in the direction of the front and back surfaces of the stem. Discs 18 of this example are also slightly wedge-shaped in vertical cross-section, having a greater thickness near a trailing edge of the machine direction in which they are manufactured (FIG. 4A), as further discussed below.

Figure 12:
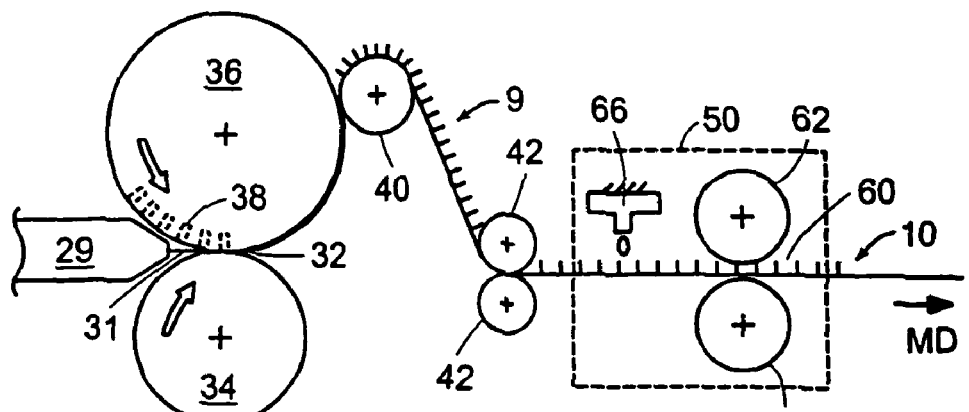
FIG. 12 is a schematic illustration of a method and apparatus for forming the preform stem product of the FIGS. 7-7C and for subsequently forming the loop engaging fastener product of FIGS. 3A-3C from the preform stem product in an in-line process.

Fastener product 10 can be formed by the method and apparatus illustrated in FIG. 12. Thermoplastic resin 31 from extruder 29 is introduced into nip 32 formed between a supporting pressure roll 34 and a mold roll 36. Pressure in the nip causes thermoplastic resin 31 to enter blind-ended stem formation forming cavities 38 of mold roll 36 while excess resin remains about the periphery of the mold roll and is effectively calendared to form base sheet 12. As the rolls 34, 36 rotate in opposite directions (shown by arrows), the thermoplastic resin proceeds along the periphery of the mold roll until it is stripped from both the mold cavities and the roll periphery by stripper roll 40. The resulting product has base 12 with integrally formed stem formations 104 protruding therefrom as described above. The direction of travel of the material illustrated in FIG. 12 is referred to as the "machine direction" (MD) of the material and defines the longitudinal direction of the resulting preform product 9 and fastener product 10 (indicated by arrows MD in the figures).

A more detailed description of the process for forming such structures protruding integrally from a base is described for instance in U.S. Pat. No. 4,775,310, issued Oct. 4, 1988, to Fischer, the entire contents of which are hereby incorporated by reference. In preferred cases the mold roll comprises a face-to-face assemblage of circular plates or rings, some having cutouts in their periphery defining mold cavities and others being circular, serving to close the open sides of the mold cavities and serve as spacers.

Once preform product 9 has been stripped from mold roll 36, it proceeds through guide rolls 42 to a head shaping station 50 where the loop engageable heads 18 are formed. Various techniques and apparatus for performing the head shaping function of station 50 are now to be described.

Preferably, as previously described, preform product 9 initially passes adjacent a non-contact heat source, e.g., the combustion products from a gas flame 66 (indicated by dashed lines in FIG. 12), arranged to heat the tips of stem formations 104. Subsequently, preform product 9 passes through predetermined gap 60 formed between rolls 62 and 64 and the tips of stem formations 104 are contacted by a conformation roll 62, as described above.

Gap 60 is less, by a controlled amount, than the overall thickness of the preform product 9 from the surface of the base opposite the stem formations to the tip of the protruding formations. Thus, the tip portions of the formations contact the roll and are compressed to cause the material to be flattened or formed in the area of 60, in a press-forming action which is sometimes referred to as "flat topping," though final product may in fact not be flat due to desired conformations applied to the head surface, as with conformation rolls 8-8D, or as a result of further forming influences that follow the press-forming action.

In the presently preferred form, roll 62 is cooled to temperatures significantly below melt or softening temperature of the resin, preferably to a temperature less than the ambient condensation temperature of water for reasons mentioned. A surface temperature of 5° to 60° C. is operable over a wide range of products; for these specifically described here, it is preferable that the surface temperature range be between 10° and 45° C., surface temperature between 25° to 30° produce excellent results in cases where the temperature of the combustion gas in which the formation extremities are immersed is in the vicinity of 1000° C. or slightly higher.

In an alternative construction the head 18 is shaped by passing the preform product 9 through a gap 60 formed between a heated roll 62 and an unheated or cooled support roll 64. A more detailed description of this type of "heated surface" head forming process is provided in U.S. Pat. No. 5,679,302 issued Oct. 21, 1997, to Miller et al., the entire contents of which are hereby incorporated by reference. Even in the case of using such hot roll forming as taught by Miller, it is recognized, according to the present invention, to be advantageous to employ non-contact preheating to forming temperature with especial advantage being obtained using the combustion gas convection heating as described in which the side surfaces of distal portions of the formations are immersed in the hot combustion gases to achieve rapid heat transfer by convection and hence faster line speed and more economical operation.

Figure 5:
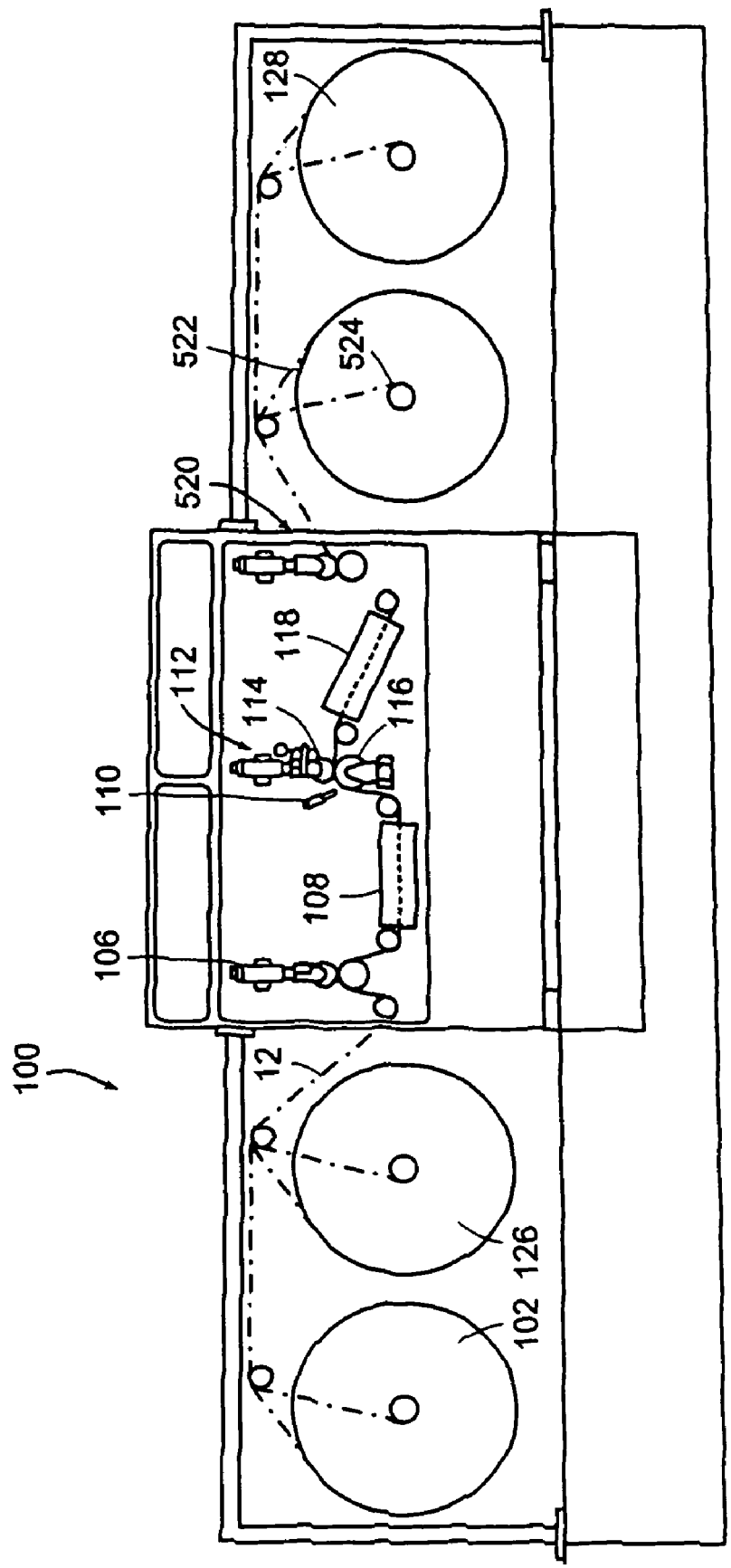
FIG. 5 is a schematic side view of a machine for manufacturing a fastener element.
Figure 6:
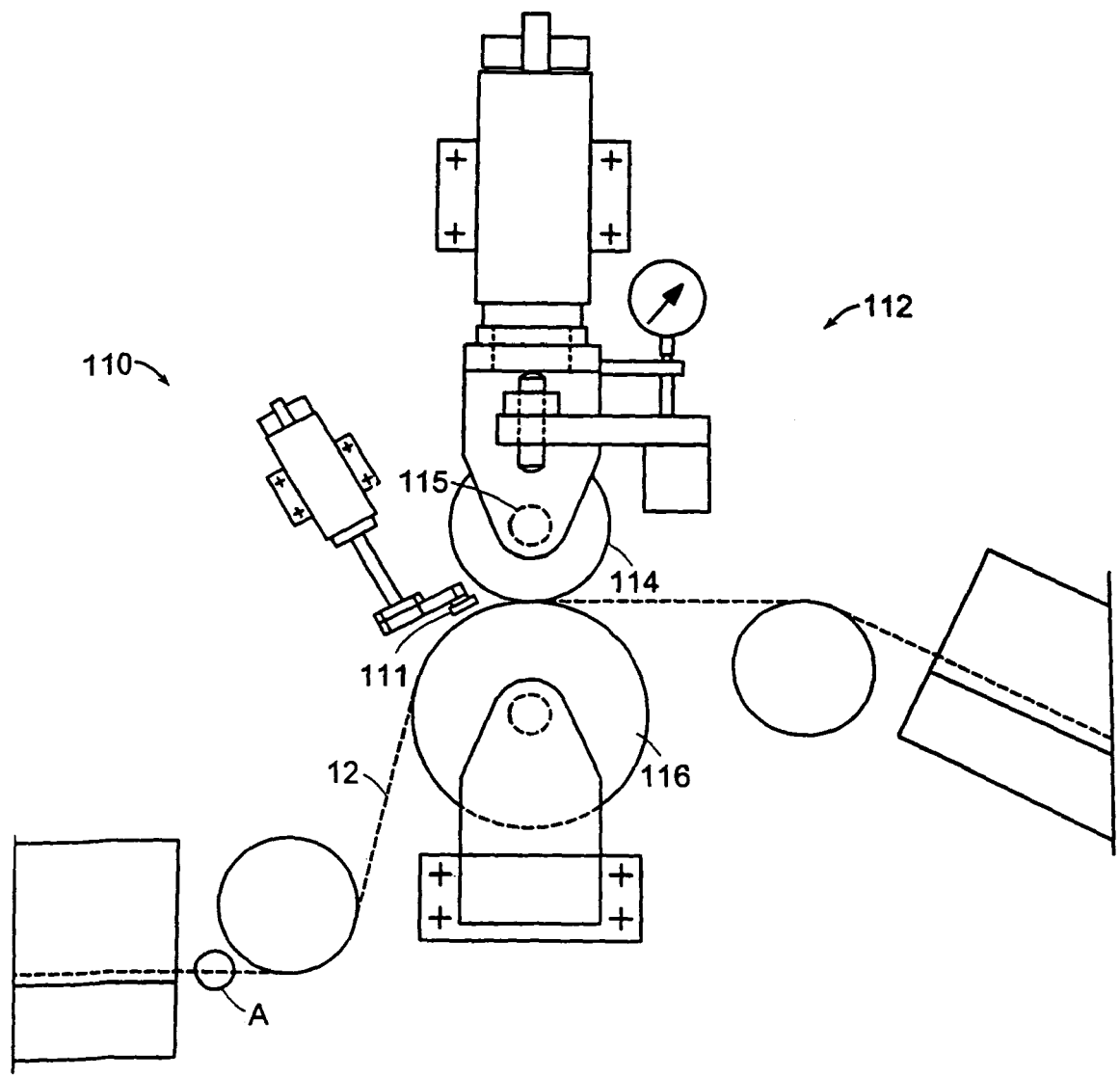
FIG. 6 is an enlarged view of a portion of the machine shown in FIG. 5.

In yet another example, which is also slow relative to the non-contact heating system of FIGS. 5, 6 and 12, an ultrasound roll is employed for heating and applying a desired head configuration. Speed of operation is enhanced by preheating with a non-contact heater, i.e. a radiant block, or exposure to convective heat transfer with gas at lower temperature.

Figure 13:
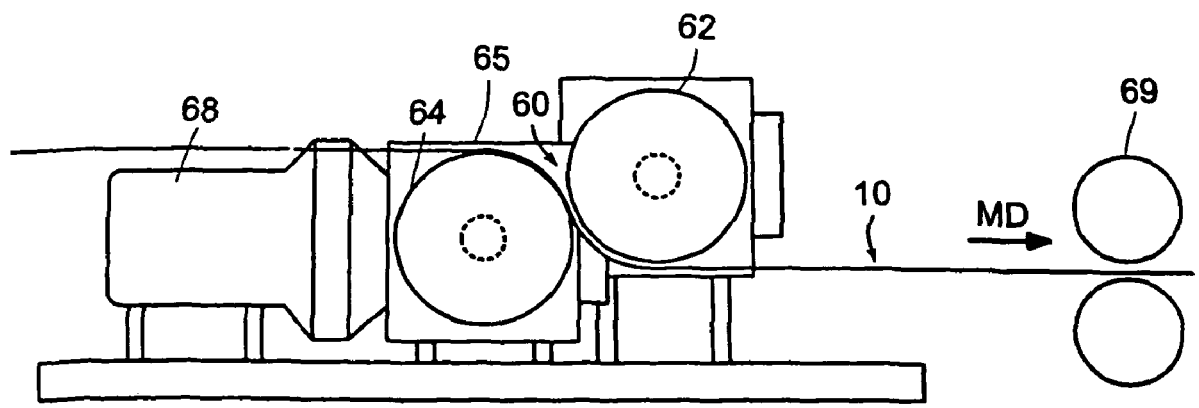
FIG. 13 is a schematic illustration of an alternative method for forming the loop engaging fastener product of FIG. 12.

In the preferred case, roll 62 is a rotary ultrasonic horn and support roll 64 is a rotating anvil. In this example, more clearly illustrated in FIG. 13, anvil roll 64 is mounted on a reducer 65 that allows the vertical position of anvil roll 64 to be adjusted, thereby allowing adjustment of gap 60. A motor 68 drives anvil roll 64 to pull preform stem material 10 into gap 60. Meanwhile, a vibration is imparted to rotary horn 62 causing its outer surface to oscillate at a frequency typically between 18 and 60 kHz. Horn 62 is arranged to vibrate and cyclically compress the contacted portions of the stems as they pass through gap 60, the vibration occurring at a frequency that causes the tips of thermoplastic stem formations 14 to flow and be formed by the contacting surfaces. The result is a flattening deformation of the tip portions of the stems to form the disc-shape, loop engageable heads 18 of FIGS. 11A-C. Subsequently, fastener product 10 is accumulated on take-up rolls 69. More detailed descriptions of ultrasonic horn and anvil arrangements suitable for use in the above-described process are disclosed in U.S. Pat. No. 5,087, 320, issued Feb. 11, 1992, to Neuwirth et al., and U.S. Pat. No. 5,096,532, issued Mar. 17, 1992, to Neuwirth. The entire contents of both of these patents are hereby fully incorporated by reference.

Figure 13A:
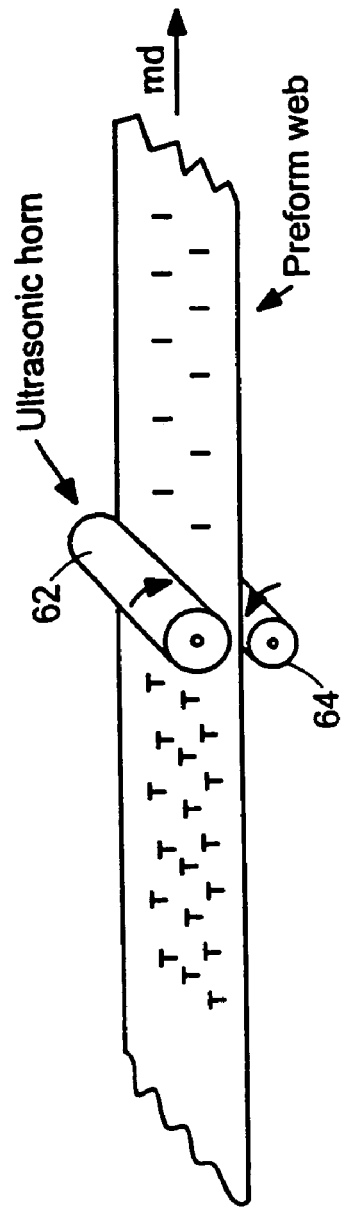
FIG. 13A is a perspective diagram showing the path of travel of a rotary ultrasound horn parallel to the machine direction.

In the diagram of FIG. 13A, it is seen that the path of travel of the surface of rotary horn 62 is in the machine direction, m.d., of the stem-forming machine. In this case, the horn surface may function as a pressing or flat-topping surface to reform the top portion of the traveling preform elements.

Figure 13B:
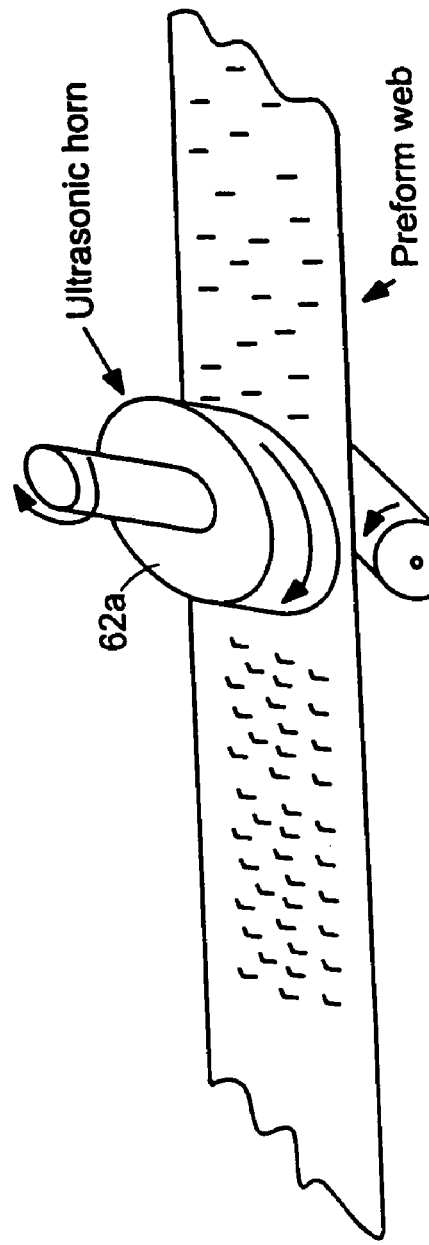
FIG. 13B is a perspective diagram showing a rotary ultrasonic horn, the axis of which extends perpendicular to the machine direction and the plane of the web of the preform elements.

In the diagram of FIG. 13B, the rotary ultrasound horn 62a has a planar contact surface arranged to brush over the tops of preform elements, with components of the brushing motion extending in all quadrants, creating multidirectional hooks, including, importantly, hooks overhanging their base in the cross-machine directions. An optional water spray may be introduced in advance of the stems to serve as a coupling agent to prevent adhesion of the stems to the vibrating surface. By suitable choice of resin, melted resin at the tops of the stems, resulting from the vibration is brushed plane-wise into the form of thin disc-form heads at the ends of the stems.

Figure 14:
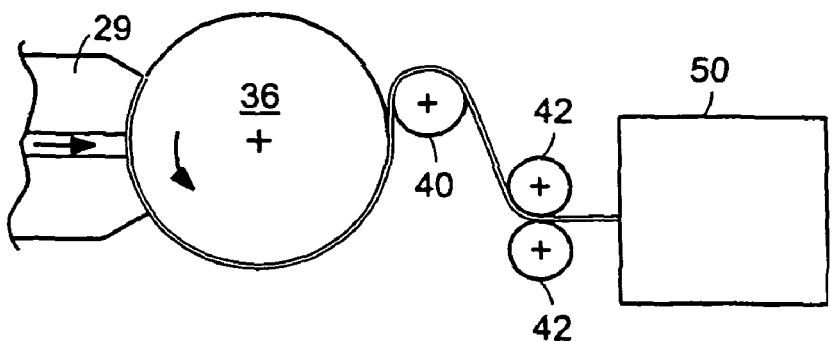
FIG. 14 is a schematic illustration of an alternative apparatus and method for forming the preform stem product of FIGS. 7-7C.

In another embodiment, illustrated in FIG. 14, an alternate technique for producing preform stem product 9 is employed. The process is similar to that described above with reference to FIG. 12 except only a mold roll is used, i.e., no pressure roll is necessary. Here, the extruder head 29 is shaped to conform to the periphery of the mold roll and the extruded resin 31 is introduced directly to a gap formed between the mold roll and the extruder head. The remainder of the process proceeds as described above with reference to FIG. 12.

Figure 11A:
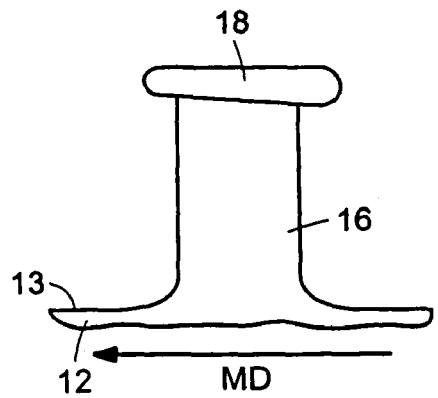
FIGS. 11A, 11B and 11C are further magnified front, side and top views of an individual loop engaging fastener element of the loop engaging fastener product of FIGS. 10A-10C.
Figure 11B:
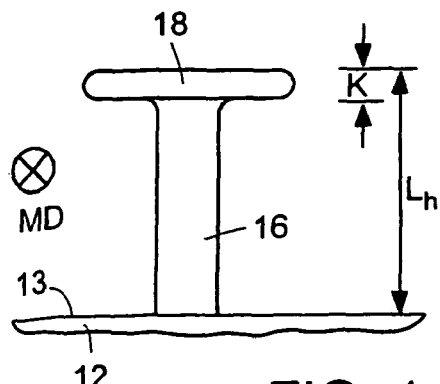
Figure 11C:
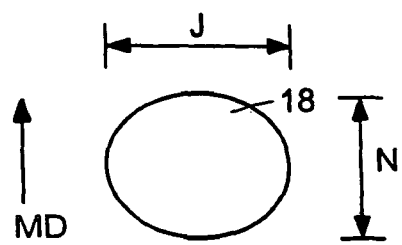

The shape of the engaging heads 18 of the fastener product is dictated by a number of parameters. For example, the wedge shape illustrated particularly in FIG. 11A is commonly the result of the dragging of the head portion of stem formations 104 as they are deformed in head forming station 50 of FIG. 12. Thus, the wedge is thicker at the rear edge of the engaging head as the material is pressed rearwardly while base 12 moves forward in the machine direction. The difference in thickness between the front and rear of the wedge can be adjusted by, e.g., process speed, heat applied (if a heat deformation process is used) and by the adjustment of deforming gap 60.

It is found that particular forms of the shape of stem formations 104 of preform product 9 significantly affect the loop-engageability properties of the male fastener needed, and important aspects of the present invention concern these preform products per se, as well as their effective use in the various forming systems described, and especially systems employing non-contact heating and/or melting. In one example, illustrated FIGS. 15A, B and 16A, B and C, a relatively short stem design is employed. The preform stem height, $L_h$, is of the order of 0.018 inches, a width, w, of the order of 0.008 inches, and a length, l of the order of 0.008 inches, again providing a stem of square cross-section. While the engaging head 18 (FIGS. 16A-16C) formed from such a preform element can have the same dimensions as the taller fastener element previously described above with reference to FIGS. 11A-11C, the shorter stem portions enable the fastener elements to be more rigid.

In the embodiment of FIGS. 17A, B and C, a particular preform stem shape is used to determine a final fastener product 10 having engagement characteristics different from the above described examples. Preform stem 120 has a first stem portion 122 attached to base 12 and a second portion 124 that extends from portion 122 to define the overall height of the formation. The stem portion 122 extends to a height, $h_1$, of the order of 0.019 inches, the second portion 124 has a height, $h_2$, of the order of 0.008 inches, the overall height, $h_3$, of the formation being of the order of 0.027 inches. Second portion 124 has outer wedges 117, 119 at its front and back surfaces 121, 123 that are of triangular form with base at the transition from stem portion 122 and peak or point at the top or adjacent the respective surface 121, 123. Thus a "V" shaped central opening occurs that is devoid of thermoformable resin.

Figure 17C:
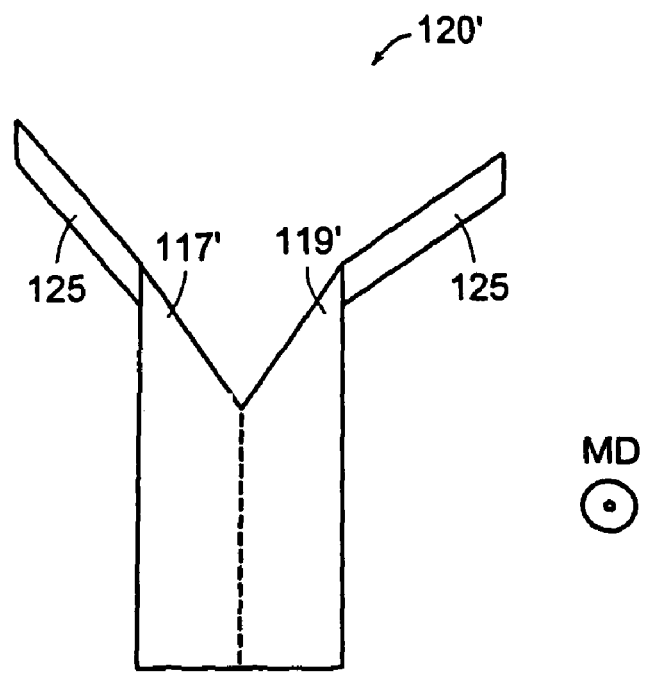
FIG. 17C is view similar to that of FIG. 17A, but illustrating a modified preform stem formation.
Figure 17D:
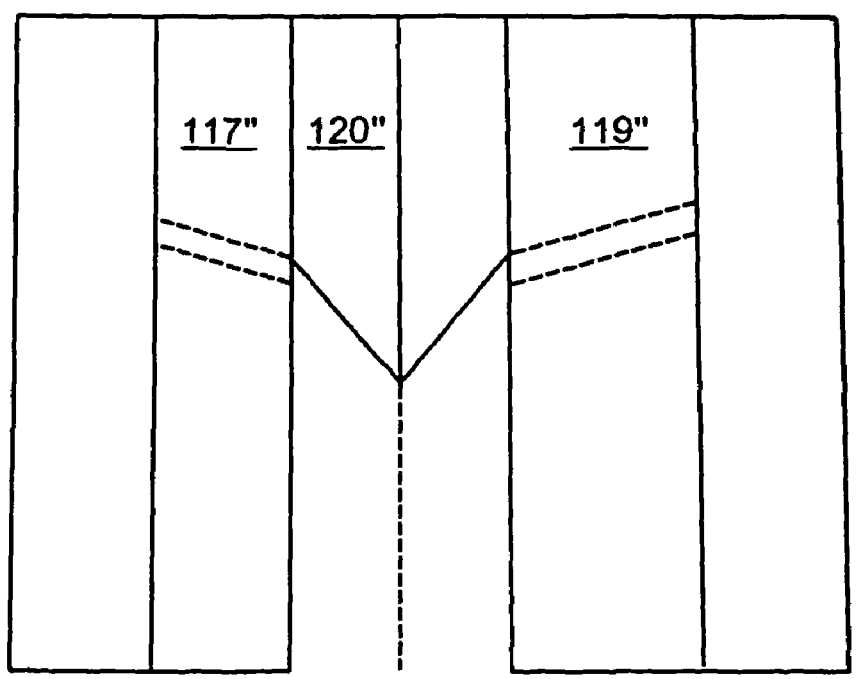
FIG. 17D is a cross-sectional view of tooling for forming the preform stem formation of FIG. 17C.

Referring now to FIGS. 17C and 17D, preform stem 120' is a modified version of the preform stem 120 described immediately above. Stem 120' has lateral extensions 125 of material that extend outward and upward from wedges 117', 119'. These lateral extensions, when reformed or deformed, e.g., by flat-topping or any of the other stem reforming operations disclosed herein, provide important features to the resulting fastener element. For example, lateral extensions 125 can be melted and/or pressed downward to create or enhance base overhanging features, and these features can be particularly directed in the cross-machine direction relative to the direction of stem manufacture. FIG. 17D illustrates a series of mold roll plates 117", 119", 120" that combine, along with outside spacer plates, to form a cavity capable of producing stem 120' of FIG. 17C.

As illustrated in FIGS. 18A-18C, subsequent processing of stem formation 120, using, e.g., one of the above described head forming techniques to deform substantially all of second portion 124 of the FIG. 17 preform element can result in a fastener element 130 having a substantially larger major diameter, J, in the machine direction (MD) than its minor diameter, N, in the cross-machine direction. This asymmetrical head shape allows for a directional increase in peel and shear forces, as the longer overhang in the machine direction retains, e.g., an engaged loop better than the shorter overhang in the cross-machine direction.

The opposite effect to that of the fastener element just described can be obtained, for example, by using a preform stem shape such as that illustrated in FIGS. 19A and 19B. Stem formation 200 has a first portion 202 of height $h_1$ connected to base 12 and a second portion 204 of height $h_2$ extending to define an overall height, $h_3$, of the stem formation. The second portion 204 of the formation, beginning at a transition at the top of first portion 202, tapers substantially on each side (e.g. at an angle greater than 20°) to provide a significantly reduced dimension w at the top. In an example, first portion 202 has a height, $h_1$, of the order of 0.021 inches while the overall height, $h_3$, of the stem formation is of the order of 0.027 inches.

Deformation of substantially all of second portion 204, employing one of the above described techniques, to form an engaging head, results in the fastener element 210 illustrated in FIGS. 20A-20C. Fastener element 210 has a major diameter, J, in the cross-machine direction substantially greater than its minor diameter, N, in the machine direction. The result is a unidirectional increase in engagement forces due to the increased overhang of the engaging head in the cross-machine direction.

Figure 21A:
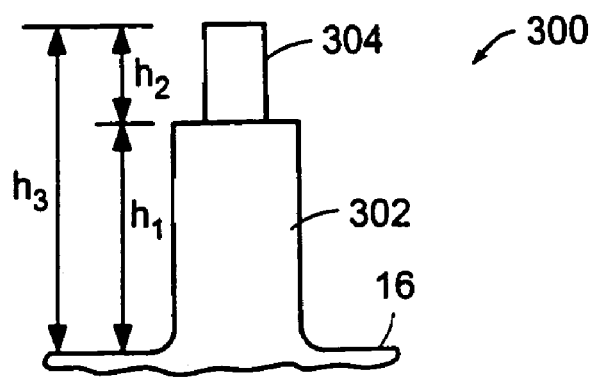
FIGS. 21A and 21B are side and top views of another preform stem formation.
Figure 21B:
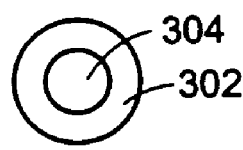
Figure 22:
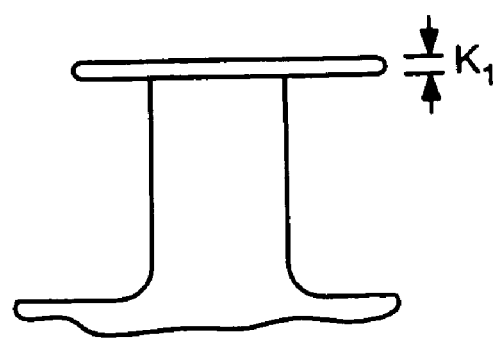
FIG. 22 is a side view of a loop engaging fastener element formed from the preform stem formation of FIGS. 21A and 21B.

In another example, illustrated in FIGS. 21A and 21B, a stem formation 300 has a first portion 302 of a first cylindrical shape and a concentric second portion 304 of a substantially smaller cylindrical shape extends to define the overall height, $h_3$, of the formation. Deformation of substantially all of second portion 304, employing, e.g., one of the above described techniques results in an advantageously thin engaging head, of thickness $K_1$, as illustrated by fastener element of FIG. 22.

This small thickness is a result of having substantially less material in the deformed head portion than in traditional preformed stems. Such thin engaging heads are advantageously capable of penetrating beneath loops with very little loft, a characteristic especially exhibited by certain nonwoven materials, for instance, ultra thin nonwoven materials used e.g., in inexpensive packaging applications in which few cycles of opening and closing are required.

Figure 23B:
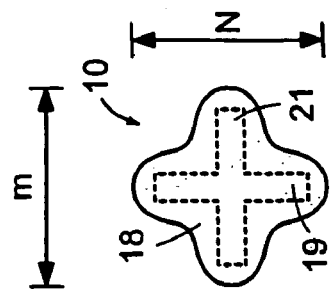
FIG. 23B is a top view taken on lines 23B-23B of FIG. 23A.
Figure 23A:
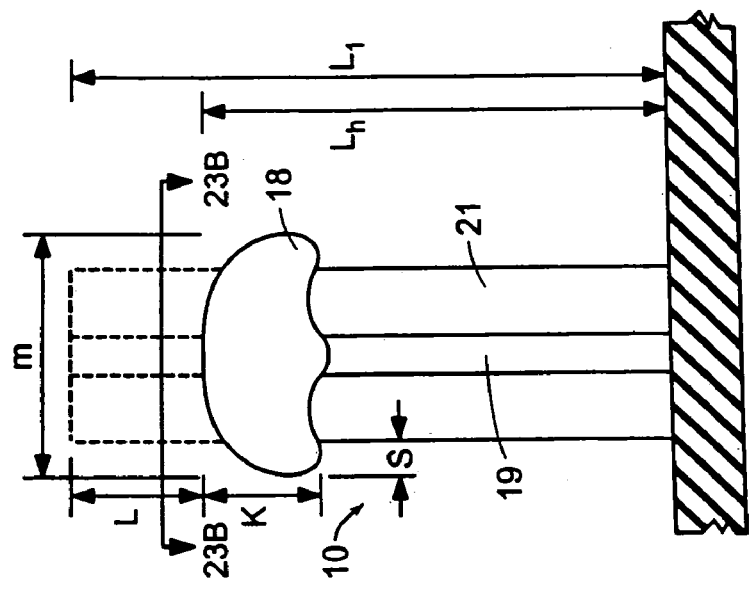
FIG. 23A is a side view taken on lines 23A-23A of FIG. 23
Figure 23:
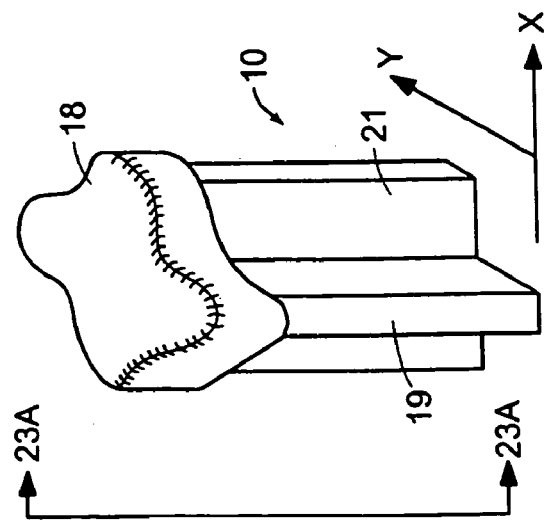
Figure 23D:
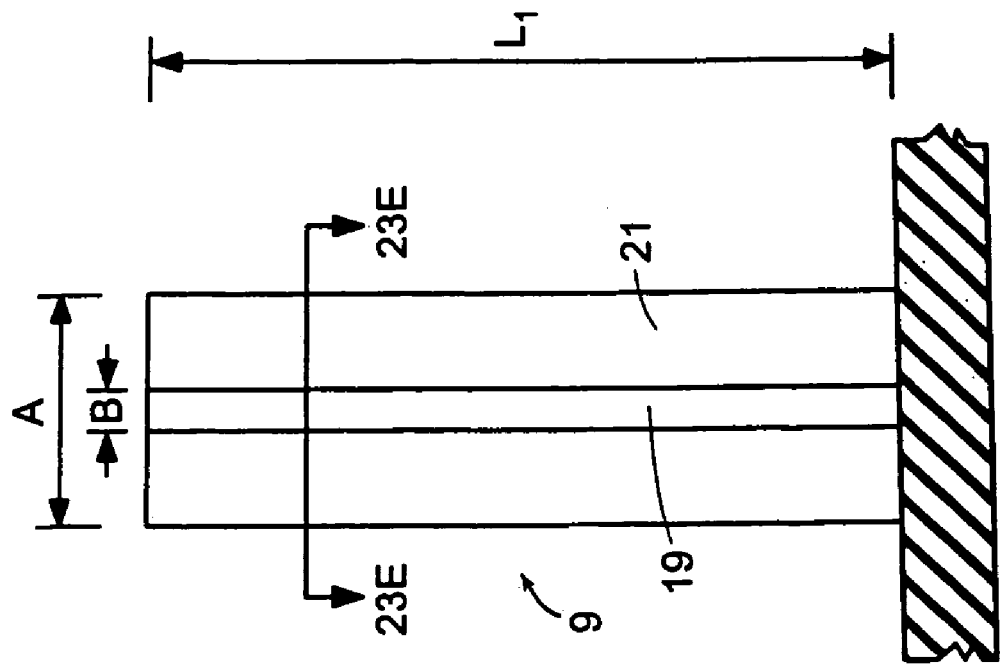
FIGS. 23C through 23E are views of a preform element employed in forming the hook element of FIG. 23, FIG. 23C being a diagrammatic perspective view of the molded preform element, FIG. 23D a vertical side view of the element and FIG. 23E a horizontal section view of the preform element taken on line 23E-23E of FIG. 23D.

FIG. 23, a highly magnified perspective view, shows a novel quadrolobal hook created by heating and pressure-heading a quadrolobal stem comprised of thin fins 21 extending along the X axis and thin fins 19 extending along the Y axis, that have been heated and reformed at their outer extremities to form hook head 18.

In the side-view of FIG. 23A, and plan view of FIG. 23B, dimension M denotes the head width in the X axis, N the width in the Y axis, K the head thickness, $L_h$ the overall hook height, $L_1$ the stem height prior to pressure-heading and S the overhang of the hook head beyond the side of the stem. For example the dimensions may generally range as follows:

|      | General Range       | Preferred Range     |
| ---- | ------------------- | ------------------- |
| M =  | 0.004 to 0.070 inch | 0.010 to 0.020 inch |
| N =  | 0.004 to 0.070 inch | 0.010 to 0.020 inch |
| K =  | 0.002 to 0.015 inch | 0.002 to 0.005 inch |
| Lh = | 0.007 to 0.120 inch | 0.025 to 0.045 inch |
| L1 = | 0.010 to 0.160 inch | 0.030 to 0.050 inch |
| S =  | 0.001 to 0.015 inch | 0.003 to 0.005 inch |

Figure 23C:
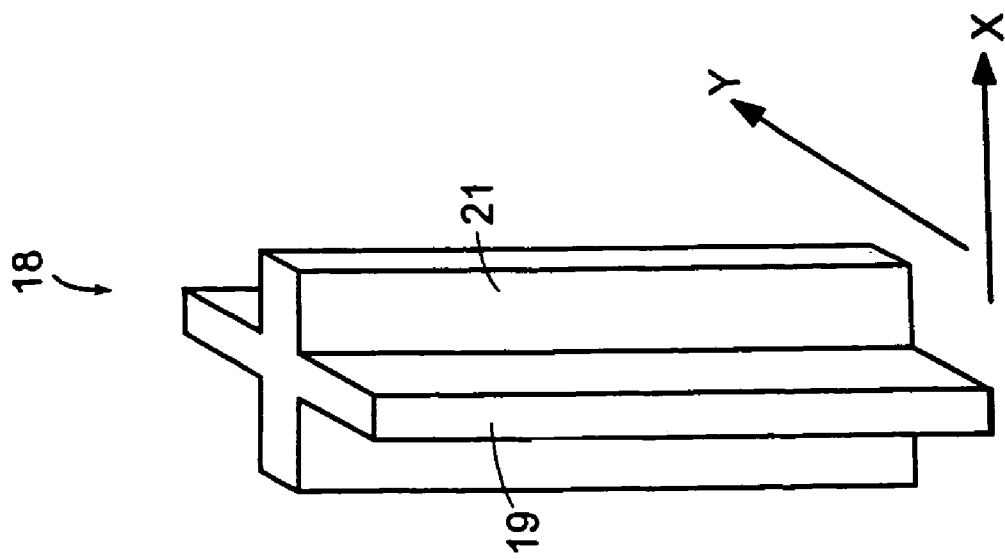
Figure 23E:
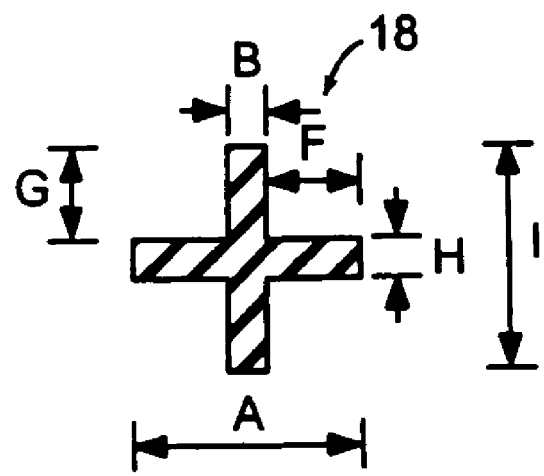

As shown in FIGS. 23C and 23E the stem is of a "plus sign" cross-section profile, fins 21,19 extending symmetrically along the X and Y axes in both directions from a common intersection. The fins have the same length F, G, the same thickness B, H and the same height $L_1$ prior to pressure-heading.

The fin profile ratio for the X axis fin is F/H and for the Y axis fin, G/B.

Figure 23F:
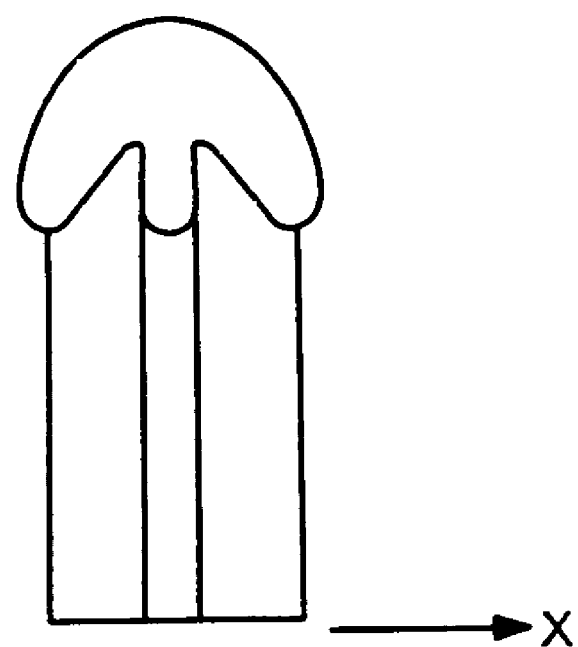
FIG. 23F is a side view similar to FIG. 23A of the stem after it has passed by non-contact heat source, before reaching the conforming roll, while FIGS. 23F-A through FIGS. 23F-E is a set of figures that illustrates the "balling" of melted resin along the exposed edge of a single thin fin element as a result of convection preheating by a gas flame.

The concept of this hook preform element is that with a fin ratio of greater than about 2, preferably around 2½, an improved head overhang is obtainable at the end regions of the fins, see the series of FIGS. 23F-A-23F-E for an illustration of the "balling effect of unoriented resin along the top edge of a thin fin, and note the bulbous overhangs at the thin ends of the fins.

With the stem preform of FIG. 23, such overhangs are provided in each sense in orthogonal directions.

According to this aspect of the invention, a ratio of less than about 2 is seen generally to result in a stem that, when heated and pressure-headed, a head of approximately the shape of a circle centered on the center of the stem results. With a fin ratio of about 2, preferably between 2 and 4, most preferably between about 2½ and 3, the geometry differs significantly from a square or circular cross-section stem such that when heated, surface tension of unoriented polymer will form lobes on the ends of the fins that remain somewhat independent, see FIGS. 23F and 23F-A-23F-E, this being especially the case when non-contact heating is employed, with immersion of the side surfaces in the hot convection gases, down to the end of the dashed lines in FIGS. 23A and 23F-E.

Whereas, in general, the extent of non-contact heating is preferably from about 15 to 25% of the total length of the protruding formation, in the special case of convective heating with gases that, from flame combustion, can be about 1000° C., the percentage length heated extends to 30% with good results obtainable.

Figure 23G:
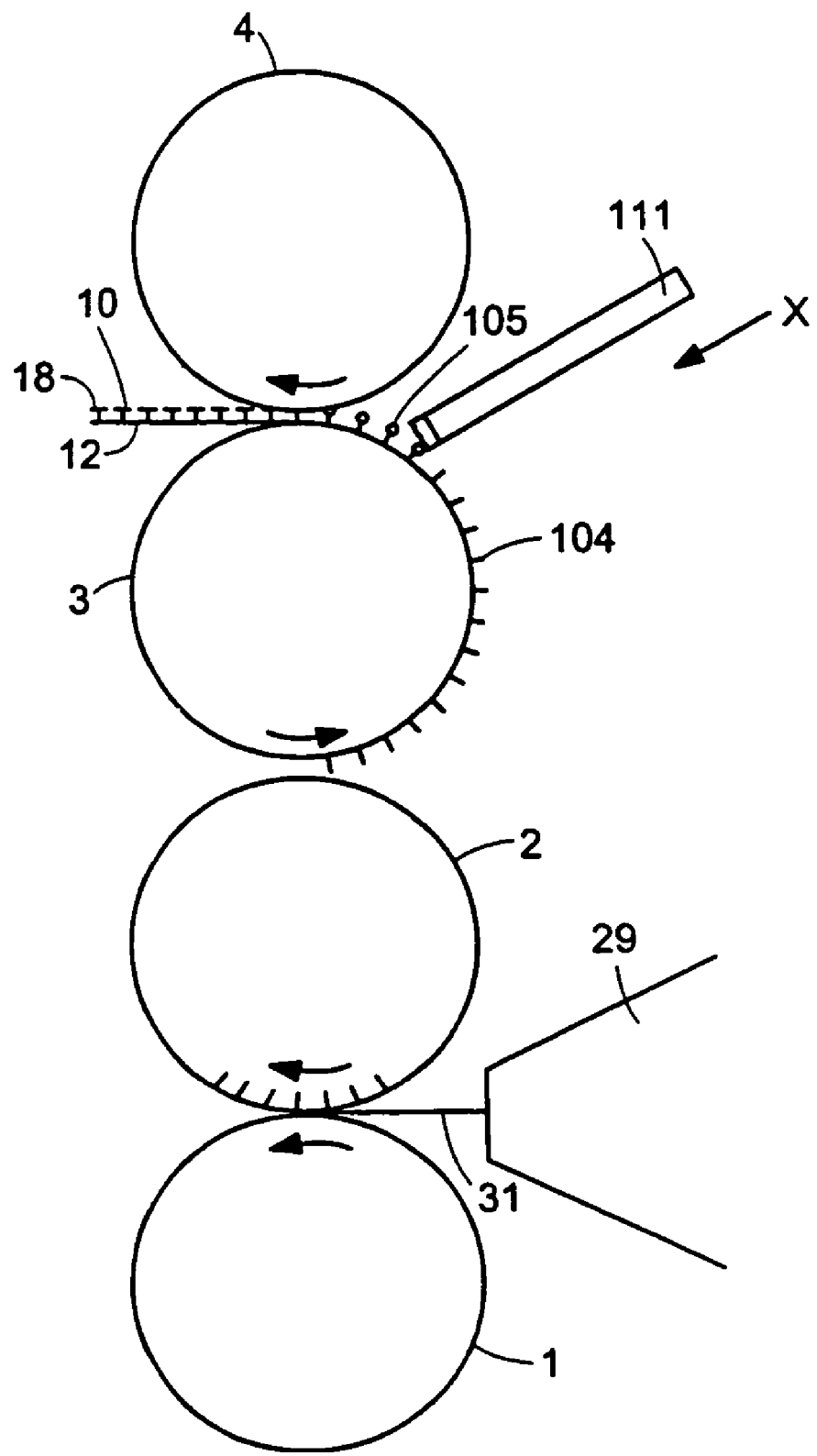
FIG. 23G is a diagrammatic side view of a forming machine, and 23H is a magnified diagrammatic view of the heading action of the machine.
Figure 23G:
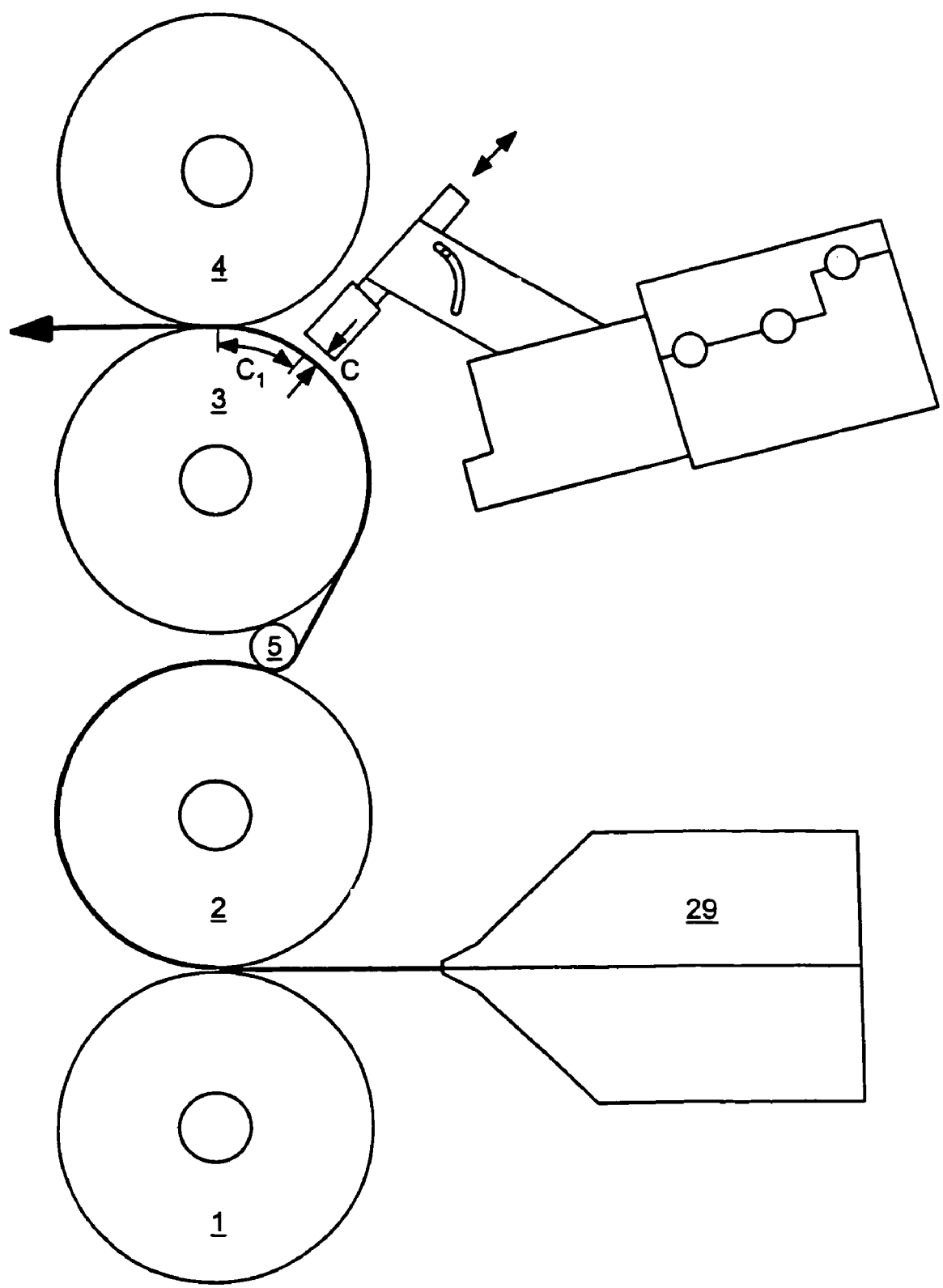
Figure 23H:
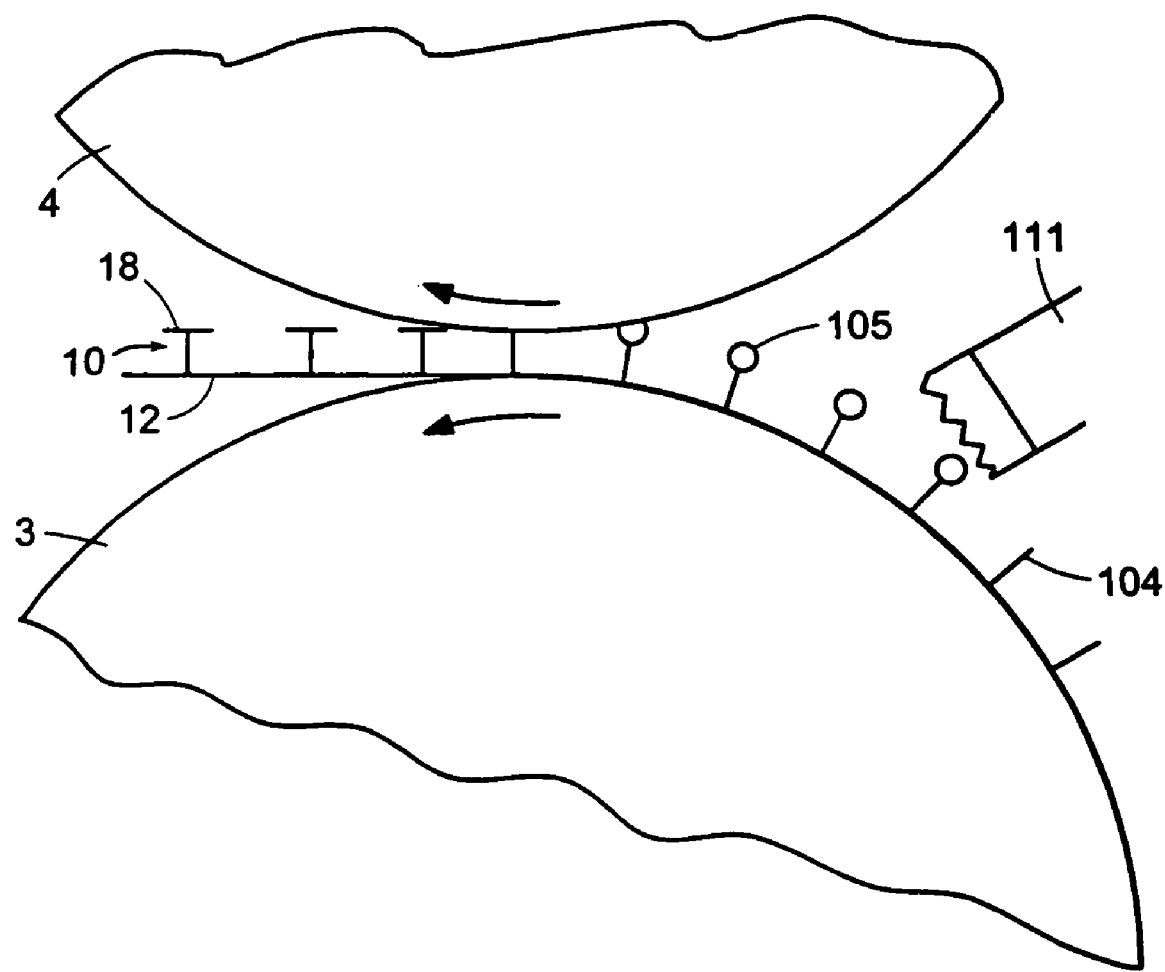
Figure 23J:
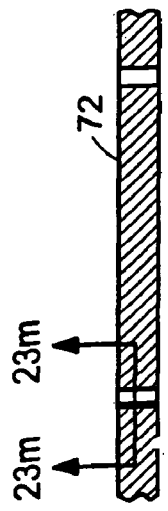
Figure 23M:
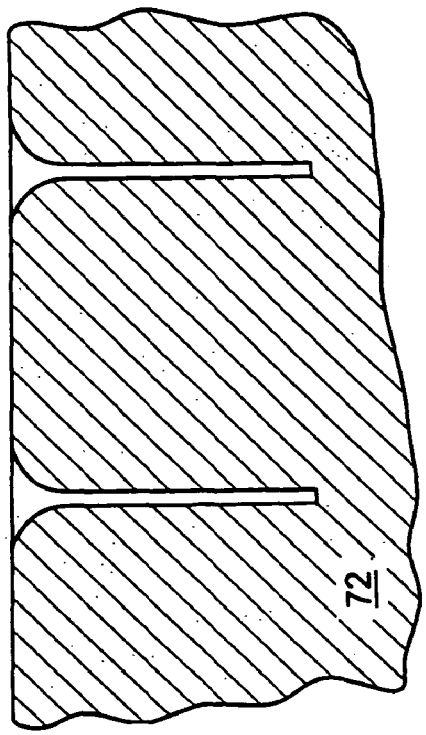
FIGS. 23L and 23M are more highly magnified cross-sections taken on lines 23L-23L and 23M-23M of FIGS. 23I and 23J, respectively.
Figure 23K:
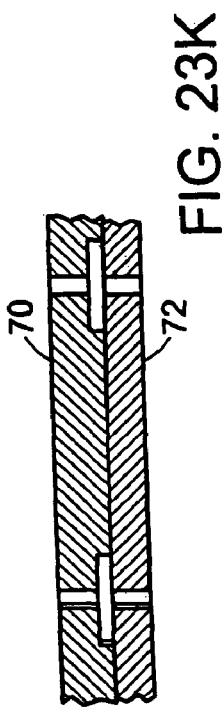
FIG. 23K is a view similar to FIGS. 23I and J, of the two mold rings held face-to-face together in registry to form a plus-form mold cavity, to mold the element of FIG. 23.
Figure 23I:
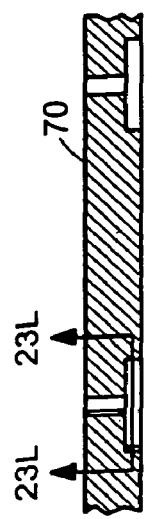
Figure 23L:
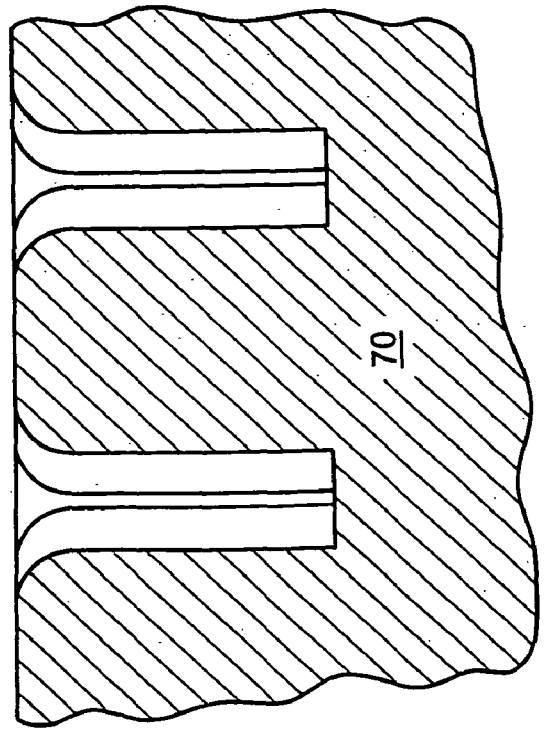

The presently preferred method for forming this product is shown in FIG. 23G, FIG. 23G', 23G" and FIG. 23H. Extruder 29 provides a traveling molten resin strip to a roll stack comprised of rolls 1, 2, 3 and 4, numbering from bottom to top. The plastic passes through the nip between rolls 1 and 2. Roll 2 is a mold roll, its exposed outer surface comprised of mold cavities such that the molten polymer flowing into the cavities takes on the form of the cavity and then is de-molded to provide preform stem 104 of substantially unoriented resin. It is one of the features of this invention that, by the use of non-contact heating, especial advantage is taken of the unoriented nature of the polymer to enable surface tension effects to act to strategically locate and size the deformable mass of polymer that highly desirable effects are obtainably by the "flat-topping" i.e. press-forming action.

Referring to reference to FIGS. 23G, G' and H, an array of stems integral with a backing sheet 18, with extent in both X and Y directions are thus molded by roll 2, and are demolded about a take-off roller 5 in making the transition to roll 3. On roll 3, close to the nip with conforming roll 4, the end portion of the stems pass under a non-contact heat source as a first step to create the hook heads 18.

In this embodiment, the non-contact heat source is a close-lying gas burner, and the sides as well as the ends of terminal tip portions of the stems are immersed in the hot gases produced by the burner. Thus the sides are rapidly heated by convective effects as are the top portions, which also receive radiative heating. Given the high surface area exposed to the intense heat, compared to the bounded volume of resin of the exposed terminal portion of the structure, this portion is rapidly melted, with highest temperature and lowest viscosity achieved at the projecting ends of the profile of the thin fins. An example is shown in FIG. 23F.

As also shown in the diagrammatical blown-up view, FIG. 23H, surface tension causes the molten plastic to form as a cylindrically rounded mass along the fin length ending in segments of spheres or balls at the ends of the fins. The circular forms 105 of FIGS. 23G and H are symbolic of the molten form, the precise form depending upon the length to thickness ratio of the fin profile, as well as the selection of the resin and degree of heating, controllable parameters of the process.

In this condition, the stems pass between another nip created between rolls 3 and 4, in which roll 4 presses down upon the molten polymer tips and forms a flattened head shape, to form heads 18 of shape depending upon the characteristics of this roll.

Preferably, the forming roll 4 is cooled, to remain at a temperature below the molten polymer temperature, preferably considerably lower.

With the surface of roll 4 cooled to temperature below the condensation temperature of steam, and in the case of use of flame from a burner to heat the stems in close proximity to a cooled conformation roll 4, water as a combustion product from the burning gas fuel condenses on the roll 4 and is found to act as a release agent for promoting clean separation of the formed heads and the surface of the roll as the headed hooks exit from under the forming roll. In this case both the cool temperature of the conforming roll 4 and the moisture promote clean release of the heads 18 from the roll surface without sticking of the heads to the roll, where that is undesirable. Best advantage is obtained by locating the point of heating close to the roll. In preferred embodiments the tip of the burner is within one centimeter of roll 3 and within 2½ centimeters of roll 4, adjustment of the separation of the burner from roll 3 serving as a control for the amount of convective heating obtained.

The air gas mixture of the gaseous fuel and air is introduced to the burner in substantially stoichiometric ratio for optimum combustion, such that substantially complete combustion occurs, producing byproducts essentially only of carbon dioxide and water.

The burner may have a ribbon opening extending across the width of the web, or may comprise jet holes, the spacing between holes being closer than the distance to the heads such that because of air entrainment a substantially uniform turbulent stream of hot gas reaches the top portion of the stems to be melted.

In one preferred embodiment a ribbon burner is used, providing a continuous line of flame. The burner temperature is between about 1000° and 1200° C., produced with a natural gas feed, the primary component of which is methane (CH4)

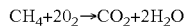

$$CH_4 + 2O_2 \rightarrow CO_2 + 2H_2O$$

Complete combustion uses 9.5 moles air for each mole of $CH_4$, thus oxygen in the air gas mix is (2 moles $O_2$/10.5 moles total) equal to 19.0% $O_2$.

The burner face is approximately 1" wide. The web carrying the stem preform travels at speeds in the range of 20 to 200 ft/min (depending upon the product desired and operating parameters), and so a stem preform element spends only a fraction of a second underneath the burner. In this amount of time a sufficient amount of heat is transferred into the preform element to enable it to be deformed into a hook. Heat is transferred to the preform element by forced convection. Heat is transferred through the stem tops as well as sides. The amount of heat transferred to the preform element, is controlled by the position of the burner relative to the elements.

Simple steps may be followed in set-up for such flat-topping.

1. Extrude and form a web of preform stems on a continuous backing, as described above.
2. Set gap position of the forming roll (Gap between rolls 3 and 4) at a position that corresponds with desired hook height while stem forming is occurring. At this point stems passing through the gap will buckle since their tips are not being heated.
3. Turn on the burner and, step-wise, bring the burner closer to the terminal ends of the stems. The burner position will typically vary from 0.2" to 1" from roll 4. The flame set-up (i.e. flow conditions) is maintained constant, so that the only variable altered is the position of the burner with respect to roll 3.

In some cases the line speed is dependent upon the amount of heat desired to be transferred to the stems. For instance, comparing 2 sets of stems, Group A: 0.008"×0.008"×0.027" vs. Group B: 0.012"×0.012"×0.075". Group B requires more heat per stem, and passing heat through a larger body requires more time for heat to be transferred such that Group B may run at a speed ⅓ that of Group A.

Figure 23N:
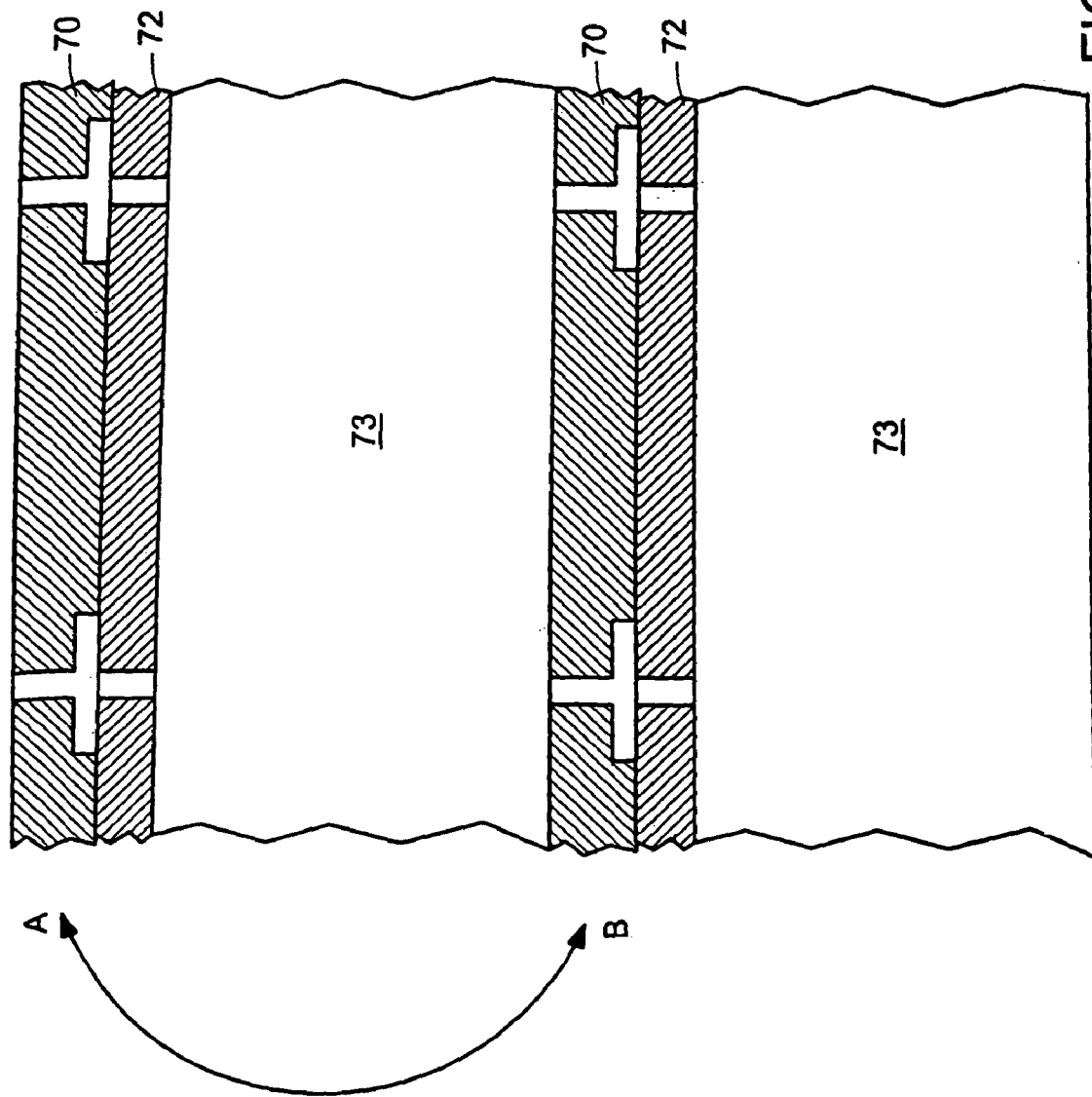
FIGS. 23N and 23O are still further magnified views of two assembly patterns achievable with the set of mold rings of FIGS. 23I and J, assembled with intervening spacer rings.

The mold cavities in roll 2, FIG. 23G, are shown in FIGS. 23I-23M. Rings 70 and 72 are placed face-to-face together in registry such that when viewed from a plan view down upon the periphery of the mold ring pair, a plus sign mold shape is provided, with fin shaped cavities of between about 2 and 3 length to thickness ratio in accordance with the provided explanation. Many sets of rings are placed side-by-side and pressed onto a shaft, providing an axial distribution of peripheral rows of cavities, FIG. 23N. The size of the cavities and their distribution is selected according to the needs of the particular fastening system being constructed. Typically a slight draft angle, e.g. of 1° is employed to enable the molded fin to readily leave its mold. As shown in FIG. 23N, solid spacer rings 73 having no mold cavities are placed between pairs of rings 70, 72. A first set of rings 70, 72 is spaced by a spacer ring from the next set, and so on. In the mold pattern of FIG. 23N the mold cavities of adjacent pairs are aligned axially of the mold roll.

Figure 23O:
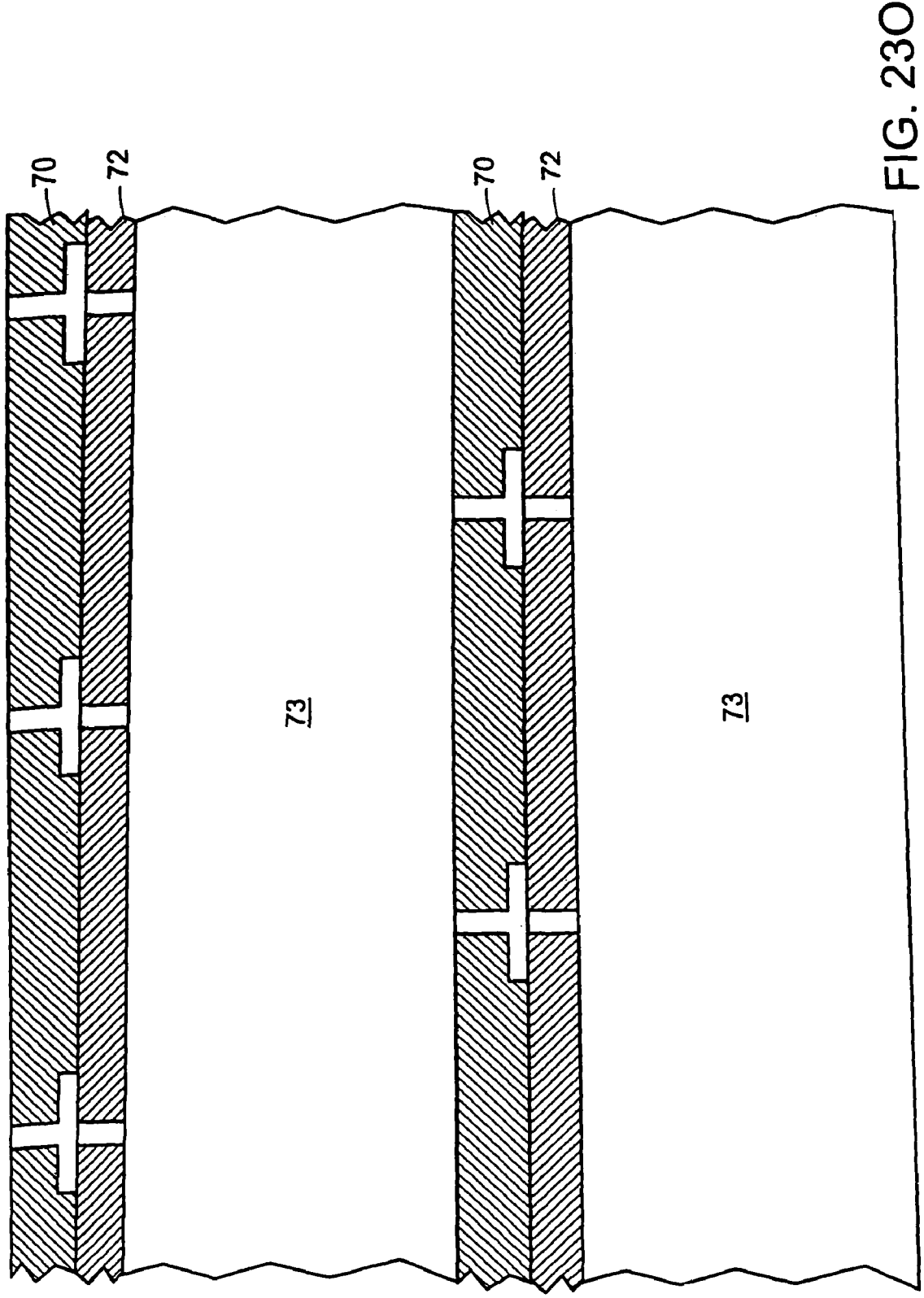

In FIG. 23O, a typical off-set pattern is shown for the tool rings. Adjacent pairs of rings are off-set by 50%, as one useful pattern for enabling engagement with loops.

According to the concept of this embodiment, the plus sign cross-section stems 104 with thin fins 19, 21 when pressure-formed by conformation roll 4 will provide polymer flow in directions of the four lobes off the ends of the fins. For diaper applications, for instance, where cross-machine directionality of the hook is often important due to the orientation of the machine direction of the fastener in the diaper forming process, this can achieve better engagement with the nonwoven loop component of a diaper than by hooks formed with a round or square profile cross-section design.

Figure 23P:
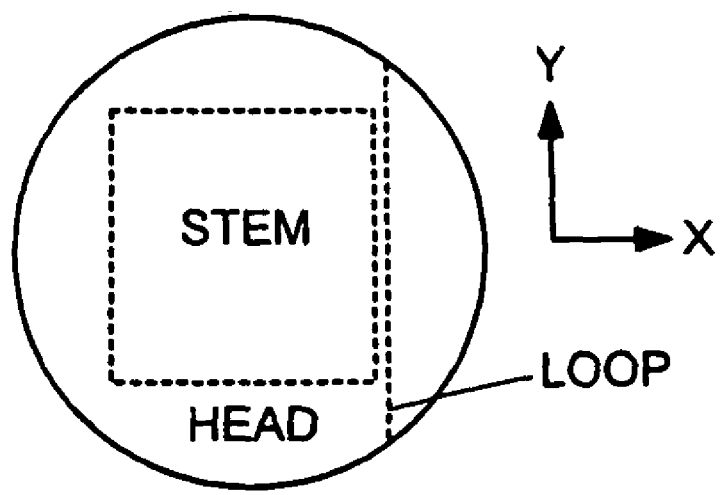
FIGS. 23P and Q are top and side diagrammatic views of a fastener formed from a square-profile cross-section stem.
Figure 23Q:
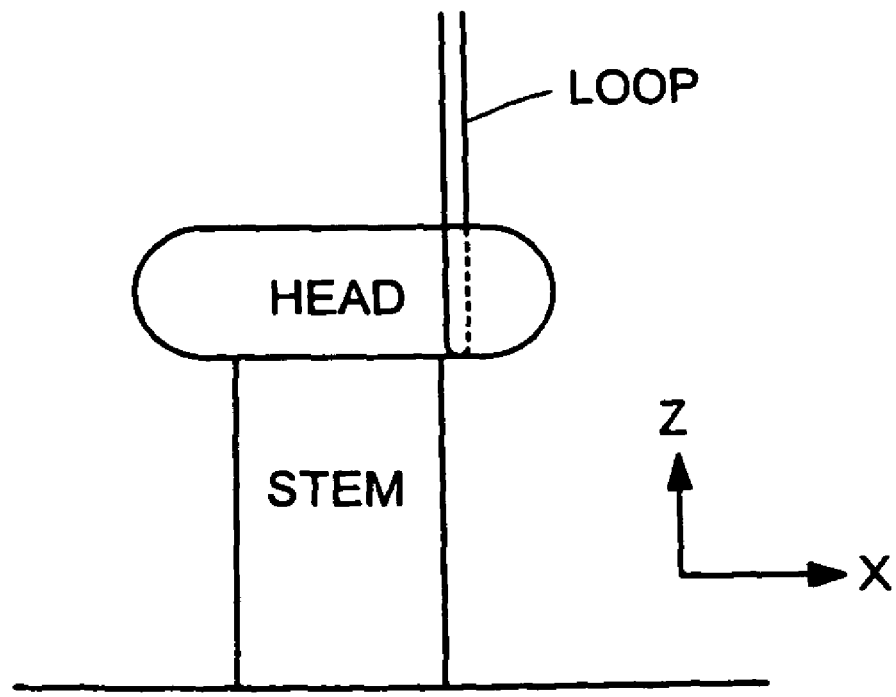
Figure 23R:
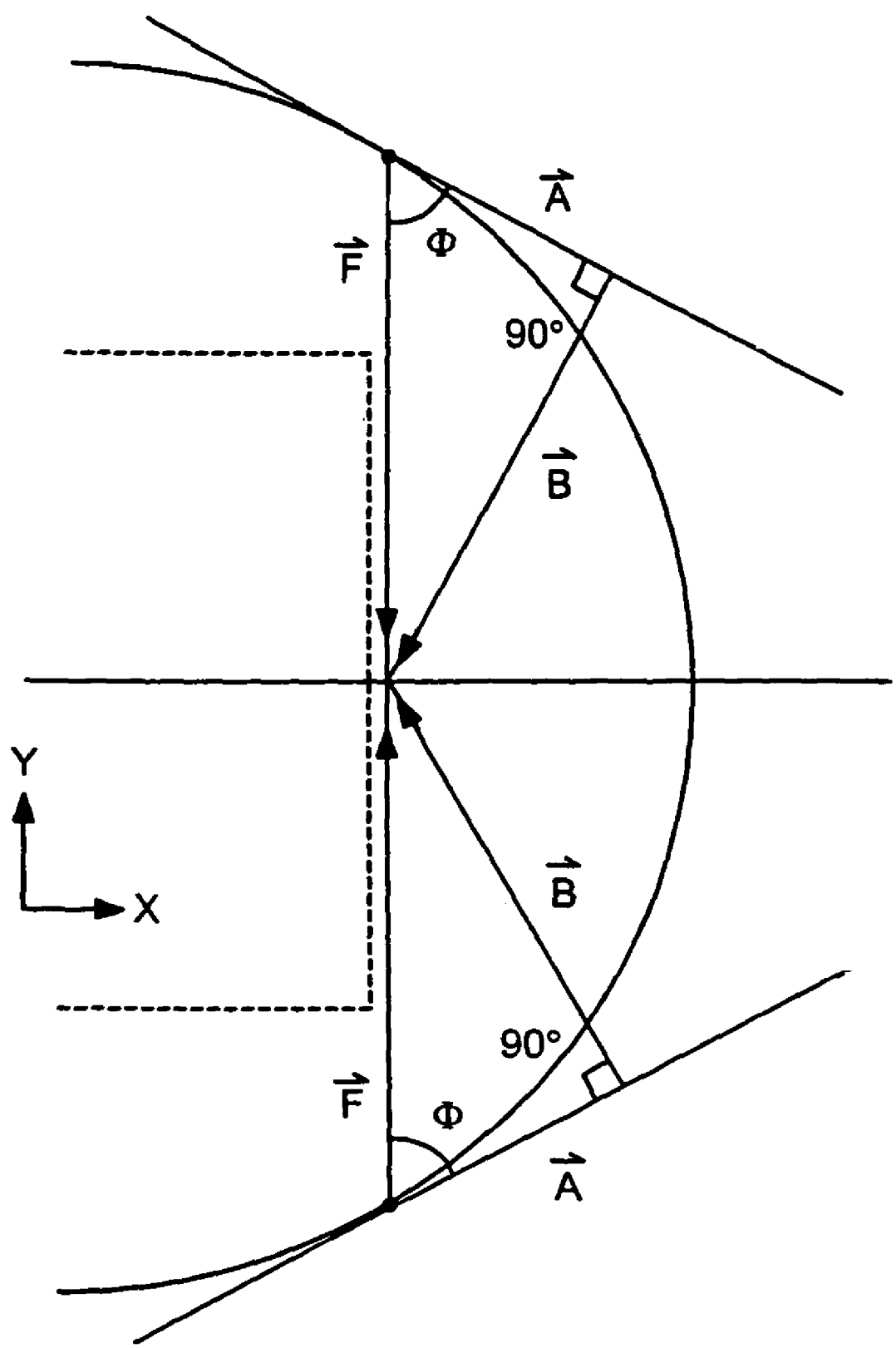
FIG. 23R is a vector diagram representing forces applied between a hook and a loop.

To explain why the thin-fin quadrolobal stem preform will provide better cross-machine directionality, referring to FIGS. 23P and 23Q, a square stem with a circular head is shown. In the side view of FIG. 23Q a loop is shown attached to the hook. The loop extends upwardly, perpendicular to the bottom surface of the hook overhang. The case where the loop is being pulled directly away from the base of the hook can be explained by vectors as in FIG. 23R. In this case the force F exerted on the loop is shown as the vector coming from the outer portion of the hook head down to underneath of the hook head to the mid point of the stem. This vector may be explained to be the sum of a vector A that extends tangent to the circle to the point where the loop exits from underneath the bottom of the hook head, heading away from the stem, and a third vector B drawn at 90 degrees, extending from the end of vector A to the end of vector F, to create a right triangle formed by side vector A, side vector B and hypotenuse vector F. The angle Φ between vectors A and F enables vector A to be written as vector F consine Φ.

For Φ between 0 to 90 degrees, as Φ increases, vector A decreases, hence the loop becomes less likely to slide off the hook when pulled.

Figure 23S:
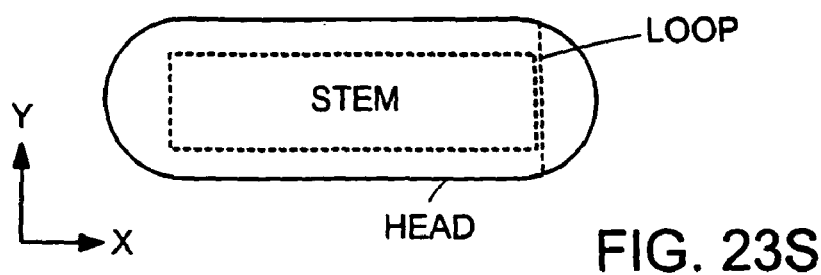
Figure 23T:
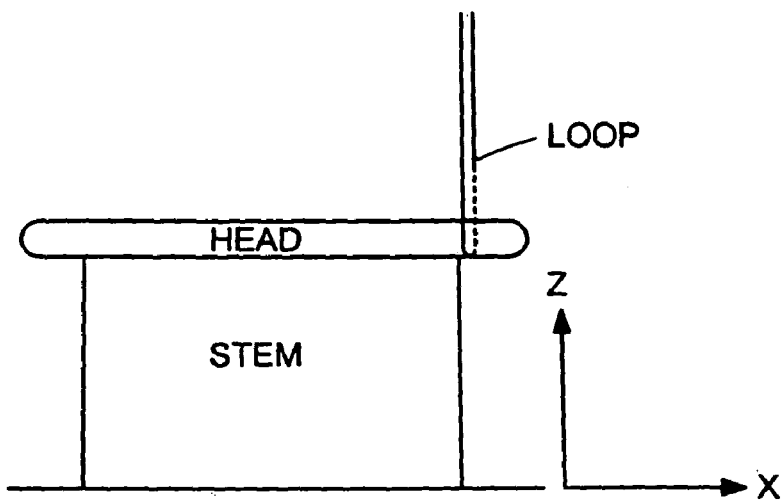

This case is compared with one lobe of head 18 of a thin-fin hook, as shown in FIG. 23S, a top view. The loop filament is at the end point of the stem and is being pulled directly up as shown in FIG. 23T.

Figure 23U:
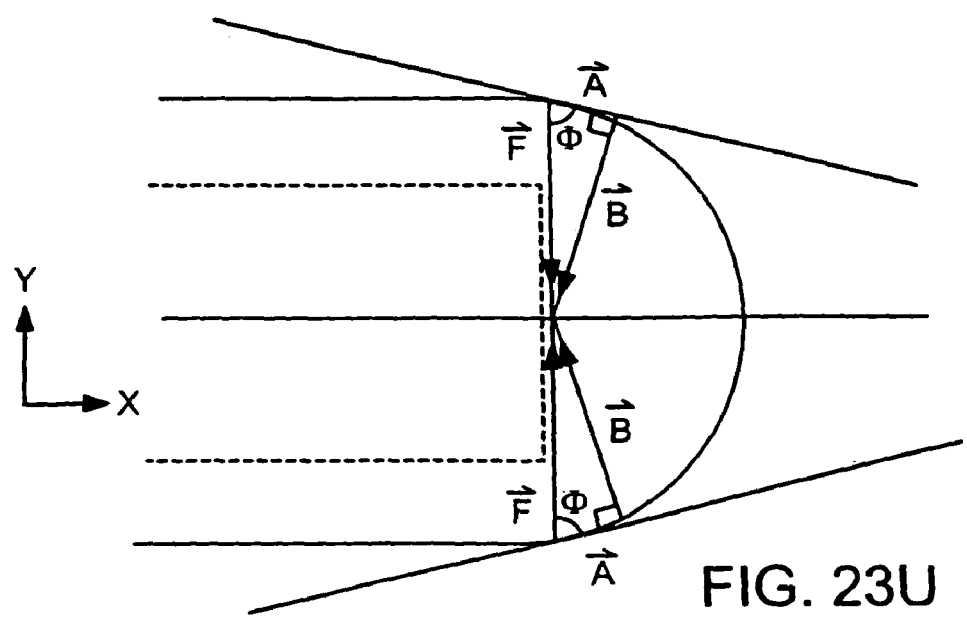
FIG. 23U is a vector diagram for the hook of FIGS. 23S and 23T, of form similar to that of FIG. 23R.

In this case, by vector analysis shown in FIG. 23U, the angle Φ is greater than the angle Φ for the circles $\Phi_{fin}$ is greater than $\Phi_{circle}$. The reason for this is, according to the present concept, the tips and short ends of a thin fin stem are deformed more compared to the long section of the fin due to greater exposed surface area to the heating conditions. The greatest overhang of the hook head then is at the end of the fin. This causes a tangent to the overhanging rim to be closer to horizontal (in plan view) than the tangent line of a similar round head, and the beginning of the widest portion of the head to be close to the end surface of the thin fin. In the case of a circular head on a stem, the widest portion of a circular head (its diameter) lies at the center axis of the stem structure rather than off-set as is the case with the thin fin.

The concept described here rests in part on the proposition that the fin tip heats locally towards its profile ends because of a higher surface to mass ratio, related to surface exposed to the localized, non-contact radiant or convection heat that reaches the side margins of the stem.

Consider the top end of the quadrolobal fins with points A on the end of one fin, B in the middle where the two fins join and C on the end of the opposite fin. When passed under a non-contact heat source points A and C are predicted to acquire more heat per unit volume of polymer and are easier to deform compared to point B. During pressure forming by roll 4, more resin is pushed off (deformed) in areas A and C compared to the middle, B, because more heat per unit volume has been transferred to the synthetic resin at those points, A and B, and therefore that resin reaches a higher temperature, and consequent lower viscosity, and more readily flows in response to forming pressure.

For a typical square stem that has a cross-section size of 0.008×0.008 inch, the head has approximately two times the width of the stem. Thus the area of the footprint of an individual hook is $0.008^2 \times \pi$, or $2 \times 10^{-4}$ inches$^2$, while the stem cross-section area is of $6.4 \times 10^{-5}$ inches$^2$. With a thin fin stem construction of the same area of ratio of 2 to 1, (length× base=$2.04 \times 10^{-5}$), the thickness is about 0.0056 inches and the length about 0.0113 inches. For the same size footprint, comparing the angle $\Phi$ between a square stem and a thin fin stem, the angle $\Phi$ is considerably greater with the fin for the same footprint than for the $\Phi$ of the circular head, or said another way, a thin fin hook of equal peel performance to that of a circular head will have a smaller footprint on the loop surface.

Footprint is important for applications such as diapers, because a small footprint allows for good penetration into a low loop mass, whereas a larger footprint tends more to push down on the loops and not allow the crook or bottom part of the head of the hook to enter under the loops that are pushed down.

This analysis indicates, further, that one can make a thin fin hook with a footprint less than that of a round head that will penetrate loop better, and get more engagement, and it can still be such that the loop tends less to slide off than with the round head.

The relationship so-far described shows the difference between a circle and a fin when the hook and loop are being separated in tension mode, i.e. at their stages of peel which are in tension mode, when the loop is pulled at an angle close to 90 degrees to the base of the hook.

Figure 23V:
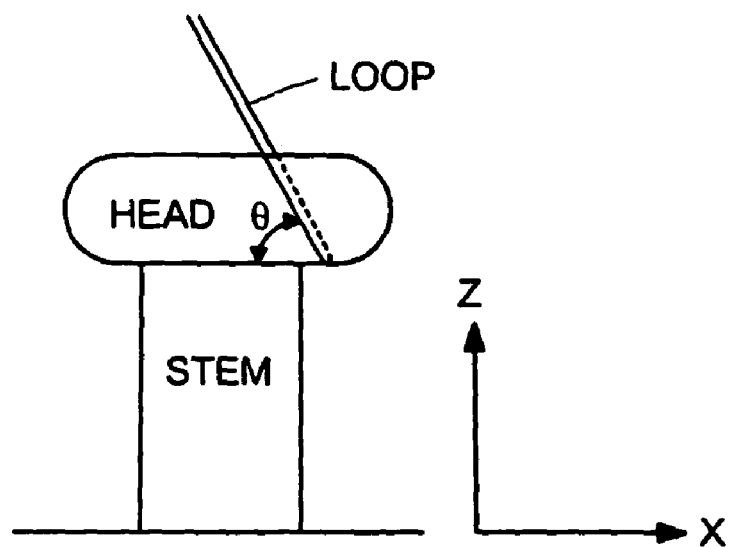
FIGS. 23V and W are similar to FIGS. 23Q and 23R, respectively, for a hook subjected to pull from a loop at an angle
Figure 23W:
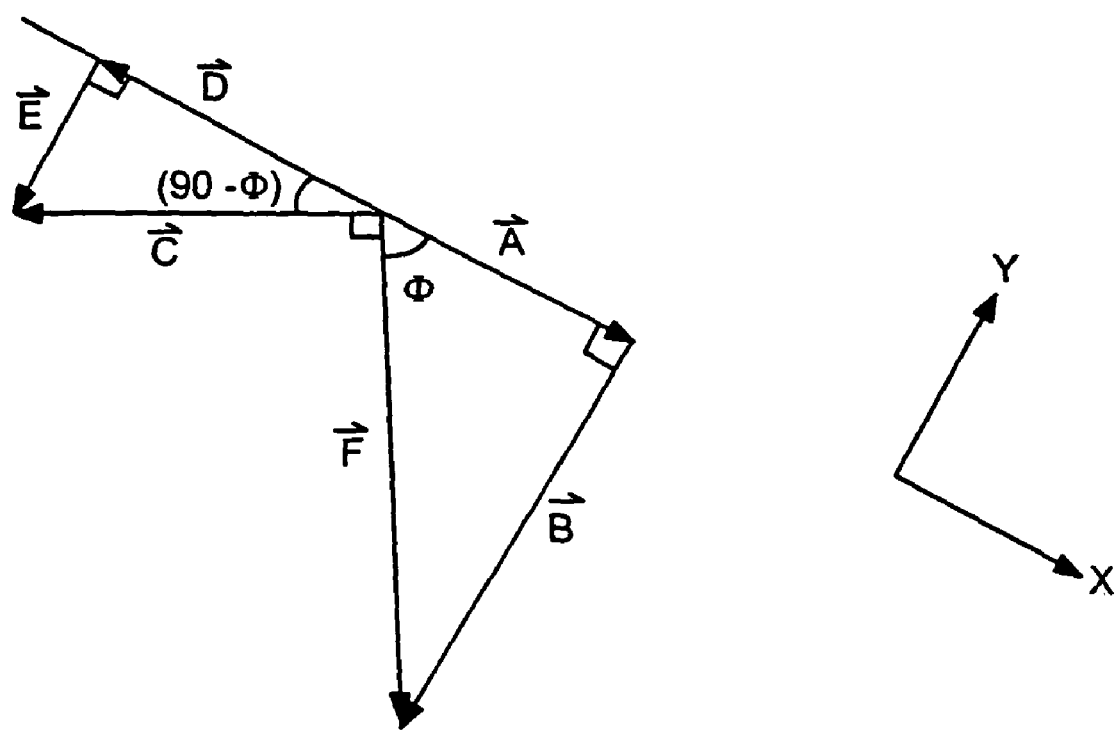
Figure 23X:
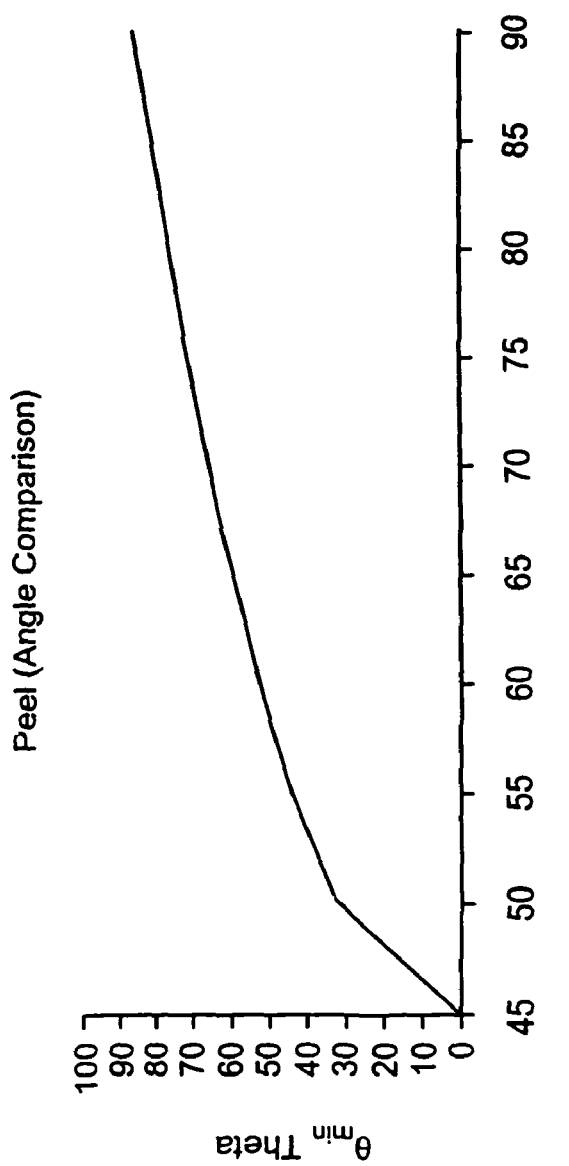
FIG. 23X is a comparison of angle $\Phi$ and $\theta_{min}$, over an angular range.

The benefits of a fin may be further explained considering the condition in which the hook is subjected simultaneously to a component of sheer loading. FIG. 23V shows a flat top hook in which the loop is being pulled back at an angle between the loop filament and an imaginary horizontal line extending across the bottom of the hook head in the X, Z plane. When angle $\theta$ is introduced, with the previous vector work, an equation may be generated to show the relationship between $\theta$ and $\Phi$, i.e. the relationship between the angle at which vector A is coming off the angle between vectors A and F. Vector A is the vector in which the loop is coming around the hook and angle $\theta$ is the angle relative to the bottom of the hook head. With angle $\theta=0$ degrees, the loop and hook are in perfect sheer mode and with angle $\theta=90$ degrees, the loop and hook are in perfect tension mode. This enables an equation to be generated, with the vectors added, to show a minimum no-slip condition effect, angle $\theta$ minimum in relation to $\Phi$ minimum is equal to the inverse cosine of the group of cosine $\Phi$ divided by sine $\Phi$. From this relationship a graph is created, FIGS. 23X, that shows the minimum no-slip condition relationship between $\Phi$ and $\theta$, angle $\Phi$ being the angle between vectors F and A and vector A being the force tending to cause the loop to slide off the hook. It shows that for an angle $\Phi$ of less than or equal to 45°, $\theta$ minimum must be 0. A loop will slide off unless it is in perfect sheer mode for $\Phi$ equal to or less than 45 degrees. This graph also shows that there is a sharp portion of the line between $\Phi=45$ and $\Phi=50$ degrees. It is realized that any small increase in $\Phi$ between angles from 45 to 50 degrees results in a much larger difference in what is required for $\theta$ minimum. Small improvements in $\Phi$ result in less of a necessity to be in perfect sheer mode.

Figure 23Y:
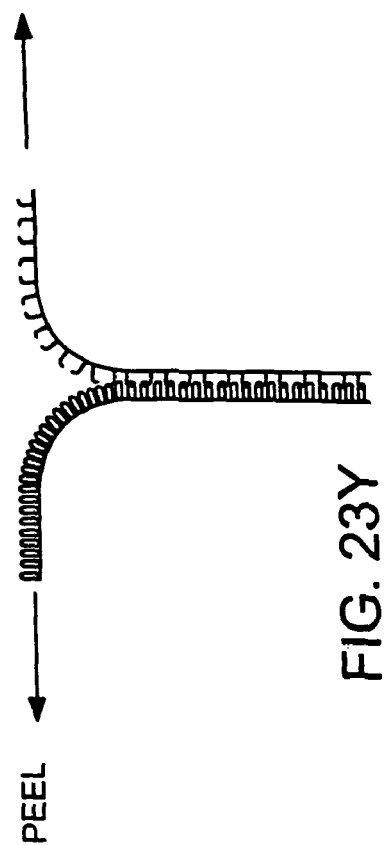
FIG. 23Y is a diagram showing hook and loop components being peeled from each other.

An important aspect of the invention concerns the realization that small changes in the head configuration can give relatively larger benefits; hence the important advantage of the thin fin construction for peel mode. Explaining further referring to FIG. 23Y a hook component is shown being peeled from a loop component. At the bottom area of the valley between the hook and the loop component the forces are substantially in tension mode, angle $\theta$ being close to 90 degrees, because no sheer force is involved. The hook is being pulled directly away from the loop at the bottom of the V during peel mode, similar to the application of forces shown in FIGS. 23P and 23T. Now, so long as the hook can hold onto the loop, as it moves up the V, angle $\theta$ starts to decrease.

If a hook at the horizontal portion of the fabric is still mated with a loop, all force is in the shear mode, i.e. resisted by the stem.

This shows the importance of having a large $\Phi$ angle to avoid dependence on the $\theta$ angle. It is believed the fin designs will have a higher $\Phi$ angle when compared with a standard round head product. Therefore, for any given $\theta$ angle, the fin design should be less likely to slip when compared to a standard round top hook. These calculations were made with the assumption of no friction; the loop conforms to head shape, thus loop stiffness is negligible, gravity is negligible and the hook is a rigid body.

The analysis applies to a plane single fin, and to the fins 19, 21 of a plus-form hook as well, and to other configurations that provide flow or forming capabilities to increase angle $\Phi$.

In condition where only cross-machine peel strength is important, a hook component formed with single fins lying cross-wise can be employed.

The plus-form or the "quad" configuration allows one to engage in differing directions.

Figure 24B:
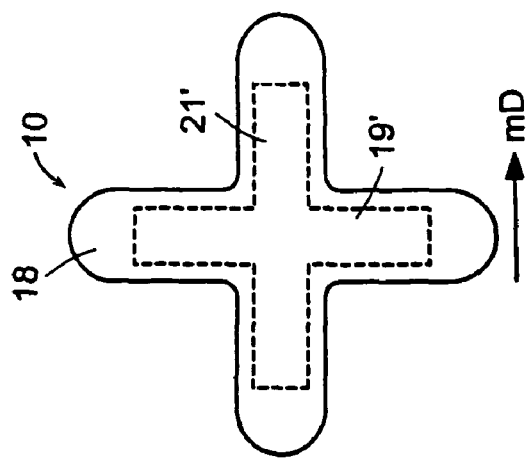
FIG. 24B is a top view taken on lines 24B-24B of FIG. 24A.
Figure 24A:
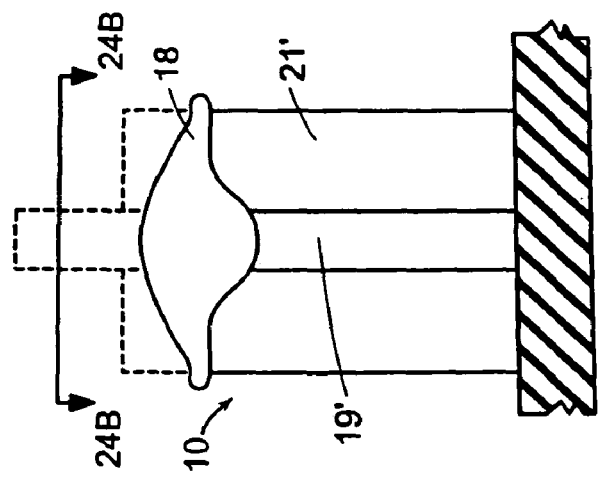
FIG. 24A is a side view of the element of FIG. 24
Figure 24:
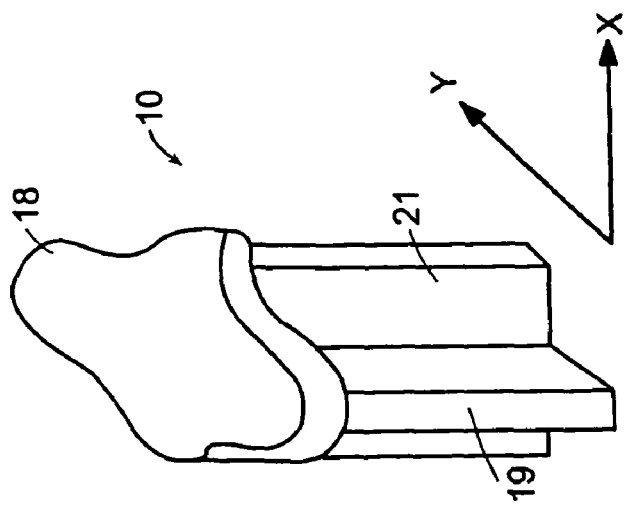
Figure 24E:
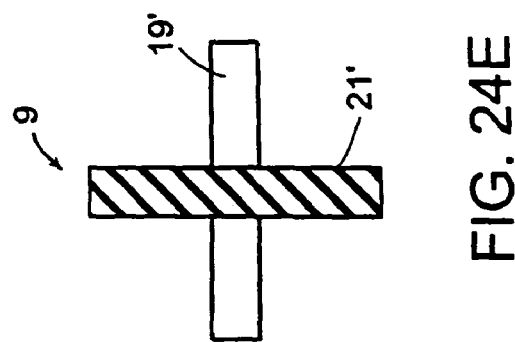
FIGS. 24C through 24E are views of a preform element employed in forming the hook element of FIG. 24, FIG. 24C being a diagrammatic perspective view of the molded preform element, FIG. 24D a vertical side view
Figure 24D:
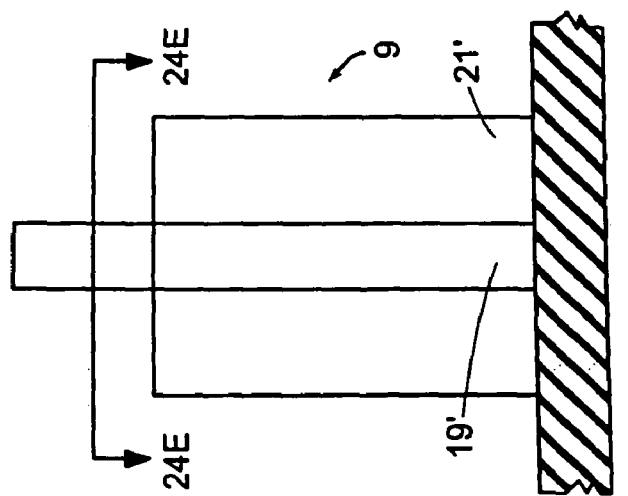
Figure 24C:
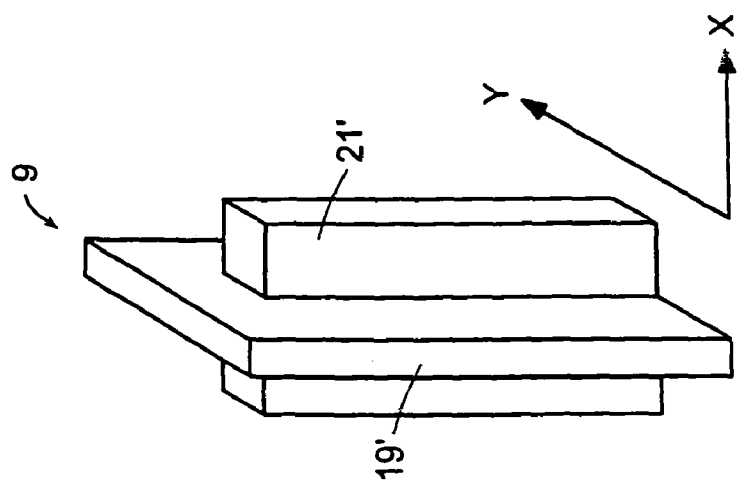

FIG. 24 is a 3-D (three dimensional) view of the quadrolobal hook created with (see FIGS. 24C and 24D) fins 21' in the X axis that are shorter than the fins 19' in the Y axis to form a hook 10 with better loop engageability in the cross-machine direction because the profile causes more polymer in the cross-machine direction to be heated and subject to forming a hook compared to the polymer of fins in the machine direction.

In certain instances the fins 21' may be so short that their outer tip portions are not reformed by roll 4. In such case, the X-direction fins act as supports for fins 19'.

Figure 25:
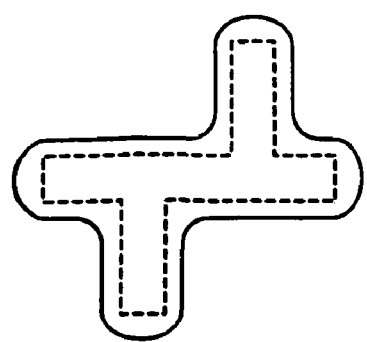
Figure 25A:
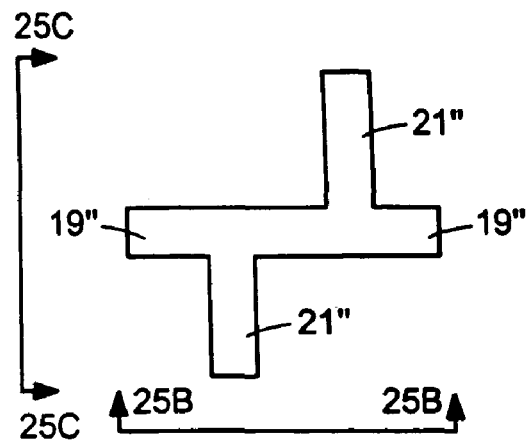
FIG. 25a is a top view of the preform employed to produce the embodiment of FIG. 25 and FIGS. 25B and 25C are side views of the preform taken respectively on lines 25B-25B and 25C-25C of FIG. 25A.
Figure 25B:
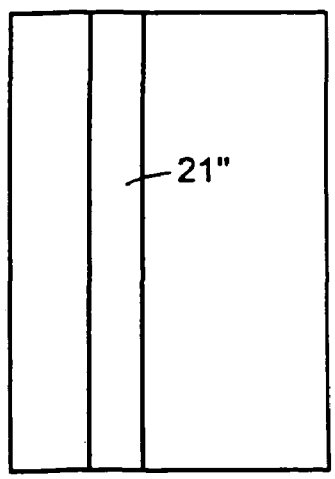
Figure 25C:
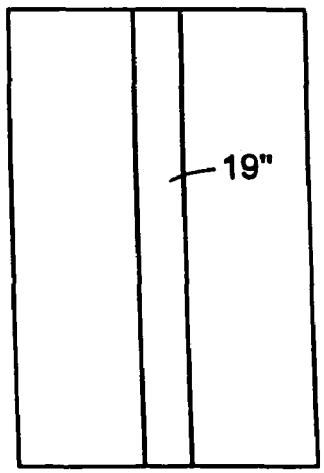

FIG. 25 is a top view of a hook created with Y axis fins 21" and 21''' offset from each other, neither being at the center of the X axis structure.

In the case of FIG. 25 fins 19" protrude at the extremities of the X axis structure beyond fins 21", at the forming station at roll 4.

Figure 25D:
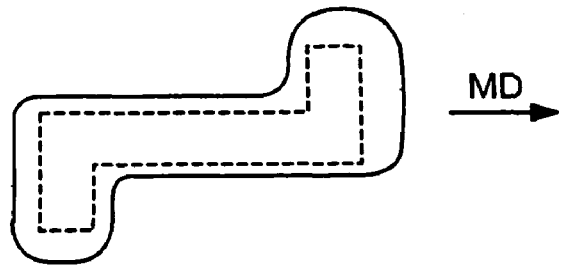
FIG. 25D is a plan view of another embodiment, similar to that of FIG. 25, but with the Y dimension fins at the extremities of the machine direction structure.

In the alternative embodiment of FIG. 25D the Y direction fins are at the extreme ends of the X direction structure.

Likewise, of course, where the effect is desired for the machine direction, the stem cross-section may be placed at 90° to that which is shown in FIG. 25D.

As shown in FIG. 25D this forms an irregular shaped hook. Under certain conditions, as shown, the head has bulbous ends and reduced width section in-between, e.g. a dog bone or bow tie configuration. Such a configuration enables a loop, that passes the widest point of the hook, to slide towards the middle of the hook, where the head is narrower, effectively trapping such loops to improve hook-to-loop engagement.

Figure 26B:
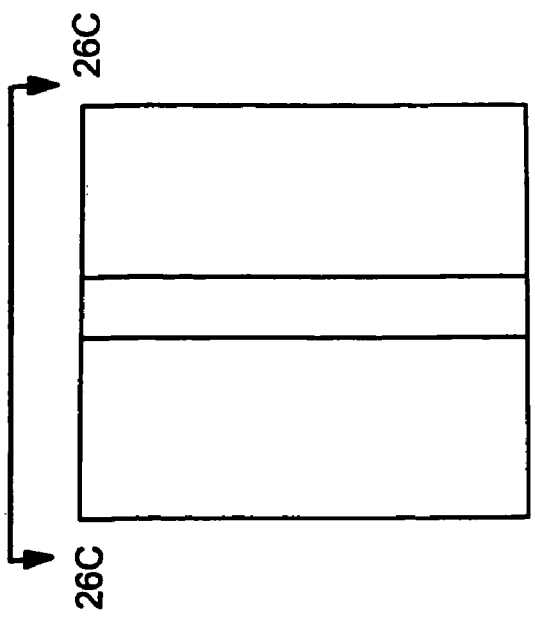
FIGS. 26B and 26C are side and top views of a preform element used in forming the embodiment of FIGS. 26 and 26A.
Figure 26C:
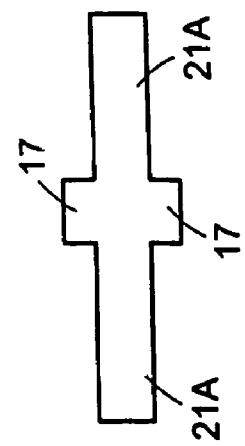
Figure 26:
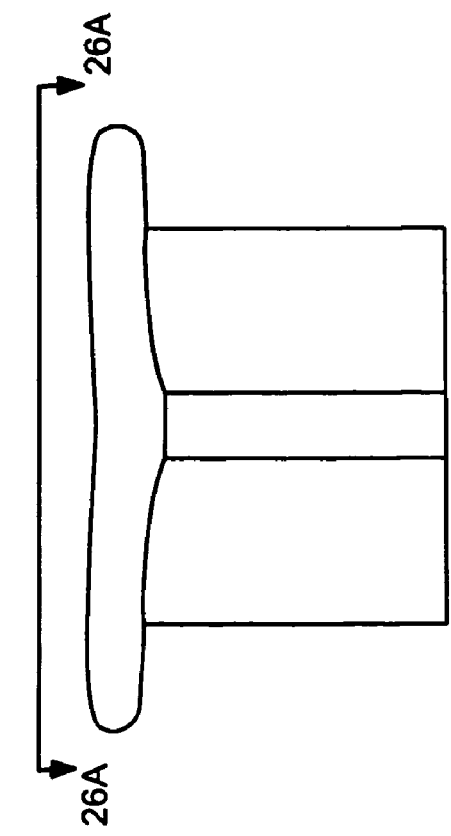
Figure 26A:
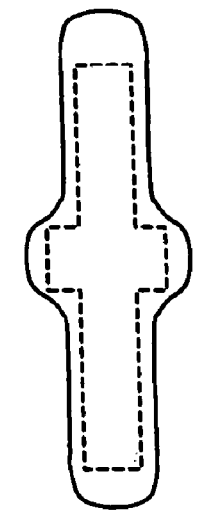

FIG. 26 is a side-view of a four feature hook created with X axis fins 21A of considerable length, and Y axis protrusions 17 that are very short in machine direction md. The Y axis protrusions 17 serve to support the hook during formation and in use as well. Importantly they reduce the foot print of the hook, allowing for easier penetration into the loop mass e.g. of thin nonwoven fabrics.

Figure 27A:
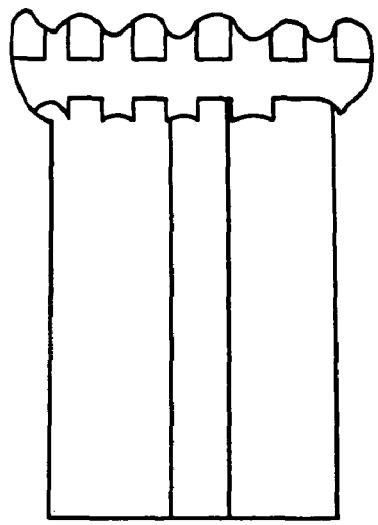
Figure 27B:
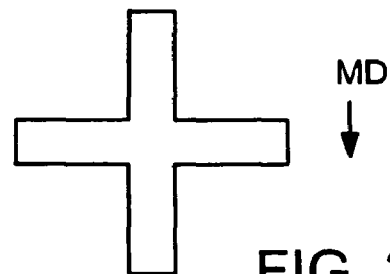
FIG. 27B is a top view of the preform element from which the embodiment of FIGS. 27 and 27A is fabricated.
Figure 27:
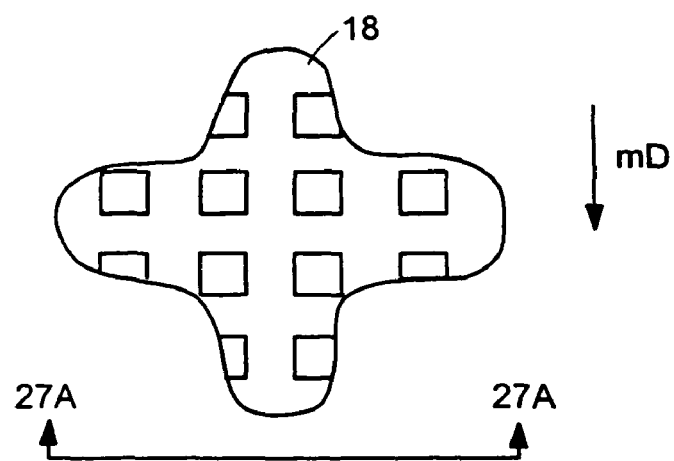

FIG. 27 is a top-view of a quadrolobal hook formed with a conformation roll having an array of embossing features much smaller than the head diameter, indicated in the form shown, as square projections. Penetration of these projections into the top surface of head 18 during its formation, serves to displace resin to a useful degree, to the undersurface though not to as great a degree as at the top surface. This provides roughness or rigidity to the undersurface and edges of the head. Such features provide mechanical obstacles or "catches" to the sliding of loops along that surface, and hence enhance loop engagement.

In other embodiments, pointed pyramidal shapes, rounded dimples and the imprint of randomly placed particles such as those of sandpaper can have like effect on the edges or undersurface of the head.

Preferably, at least three of such deformations are employed and, except in the case of relatively fine sandpaper, preferably there are less than about 15 of the deformations to avoid "wash-out" of the effect.

In certain cases the surface features of the conformation roll are selected to force resin from one X, Y location to another to enhance head overhang in some regions, decrease it in others, or provide edge friction points for improving loop engagement.

Figure 28A:
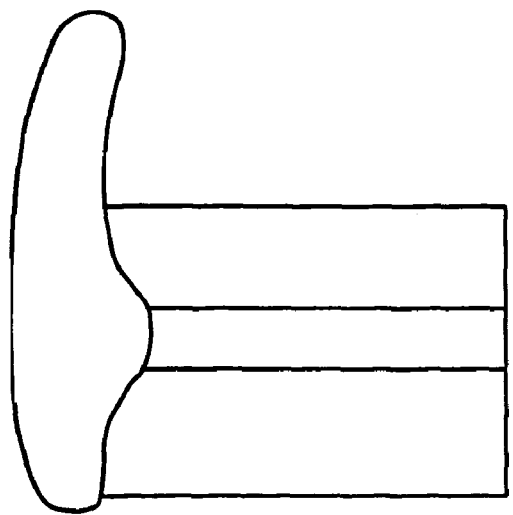
FIGS. 28, 28A and 28B illustrate another embodiment.
Figure 28B:
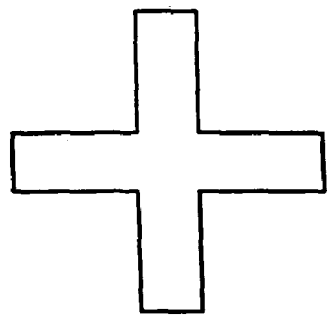
Figure 28:
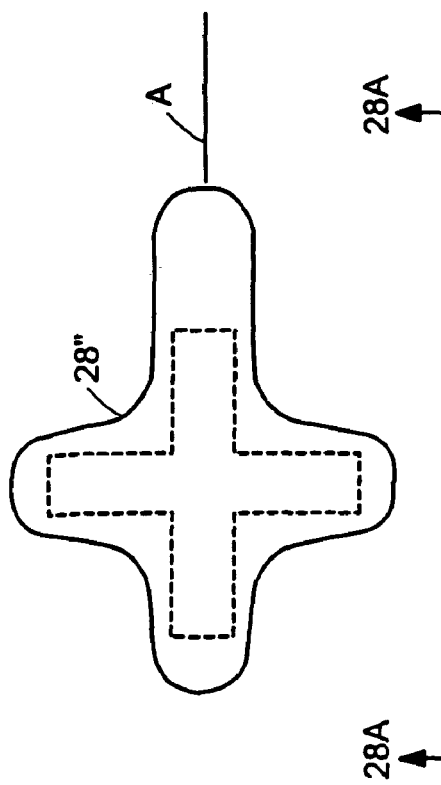

The hook form of FIGS. 28 and 28A has the head 28" shifted to one side along axis A aligned with the machine direction. This form can be created by over- or under-driving the forming roll 4 of FIG. 23G. Hooks of this type are useful in applications that require one-directional engagement.

It is useful to explain use here of the term "superheating." In general, the non-contact heating step described, when the gas flow rate and orifice sites are set has an established range of heating capability that is controlled by the distance of adjustment and is independent of the particular polymer. Using the set-up technique described above, the heating is readily adjusted to enable flat-topping and stabilization of the forms shaped by the cold forming roll 4. By adjusting the distance of the burner closer to roll 3, more heat than the minimum required for flat-topping can be applied. The system remains within the range of the flat-topping action. In that case, flat-topping is effective to distribute the resin and apply a shape, but a point is reached at which it is readily observed that the emerging forms have not yet frozen, and further, predictable deformation is observed.

It is realized that benefit can be obtained from this secondary, "self-forming" action.

In one case, by choosing a resin having a low heat deflection temperature, the method is useful to form rounded mushrooms of the self-engaging fastener type. For the example of FIGS. 29-29A, low density polyethylene (LDPE) having a heat deflection temperature of 113 degrees F. was employed (significantly lower than the heat deflection temperatures of 186 degrees F. and 204 degrees F., of high density polyethylene (HDPE) and polypropylene (PP), respectively). (For nylon and High Density PE, see FIGS. 30, 31.)

With a given coolant flow through the cold forming roll 4, after satisfactory flat-topping of the LDPE heads was established with frozen shapes emerging, the heater was brought closer to roll 3, and the line speed slowed to apply excess heat. As heating was increased, gradual change in the final conformation of the flat-topped product was observed. A point was reached in which, in a stable process, the rounded mushroom shapes shown in FIGS. 29-29C were produced. In this case flat-topping was effective to flatten and spread the bulbous molten polymer, and following roll 4, the mass sank and rounded to the form shown. Two components of this shape were effectively engaged to serve as a self-engaging fastener as depicted in FIG. 29D.

Figure 29:
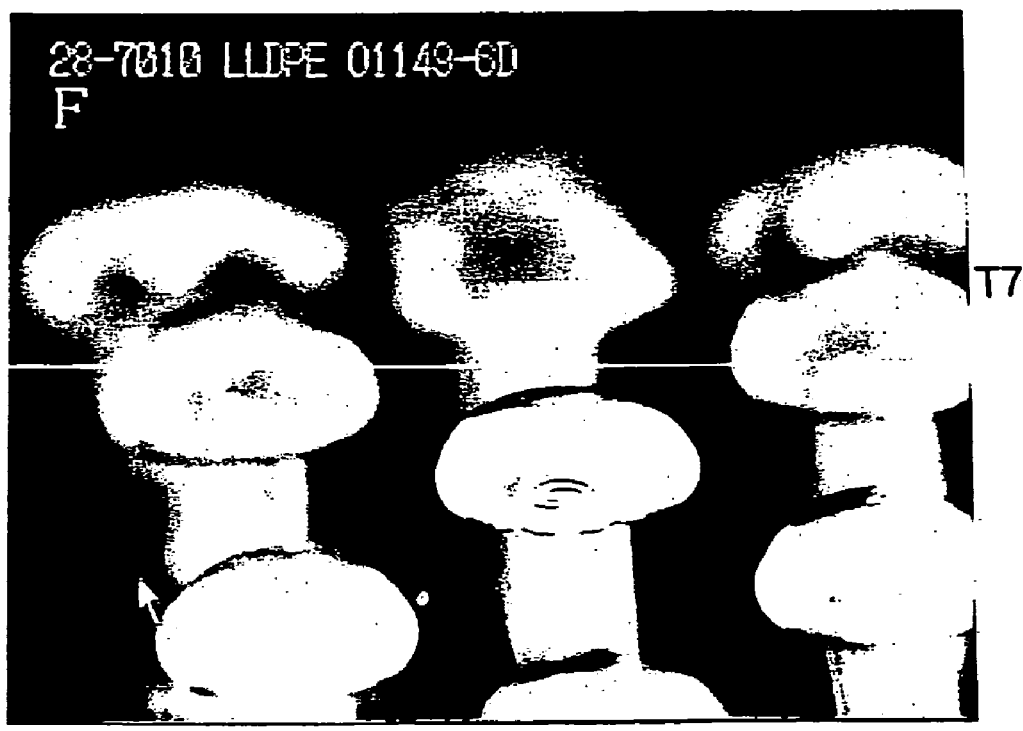

Thus, the embodiment of FIG. 29 is formed employing an initial preform stem of the form of that of FIG. 23C, however parameters are controlled to form a rounded upper profile. In addition or in combination with previous techniques mentioned for forming round tips, it is found that resin selection and an extra degree of melting, produced by "super-heating" at the non-contacting heating steps can be usefully employed.

By choice of low deflection temperature resin, e.g. certain polyethylenes, and either by making the fin construction very thin and or subjecting the tip portion to large heat transfer by the proximity or intensity of the flame, a condition can be obtained in which useful gravity flow of resin occurs after passing by roll 4. This condition can for instance also be obtained by maintaining roll 4 at such temperature that it does no entirely solidify the tip portions.

With higher deflection temperature resins, e.g., high density polyethylene, a useful self-bending action of outer edges of the flat-topped structure form the "J" profile mentioned.

The process of forming the stem preform by filling dead-end mold voids with polymer, does not orient the polymer. As previously mentioned, heating this preformed stem results in a ball of molten polymer at the top of the stem. After heating, the molten top is reformed with a flat or configured forming roll to form a head structure extending out in all directions to an extent dependent upon the height and mass of the reformed portion.

Figure 29A:
Figure 29C:
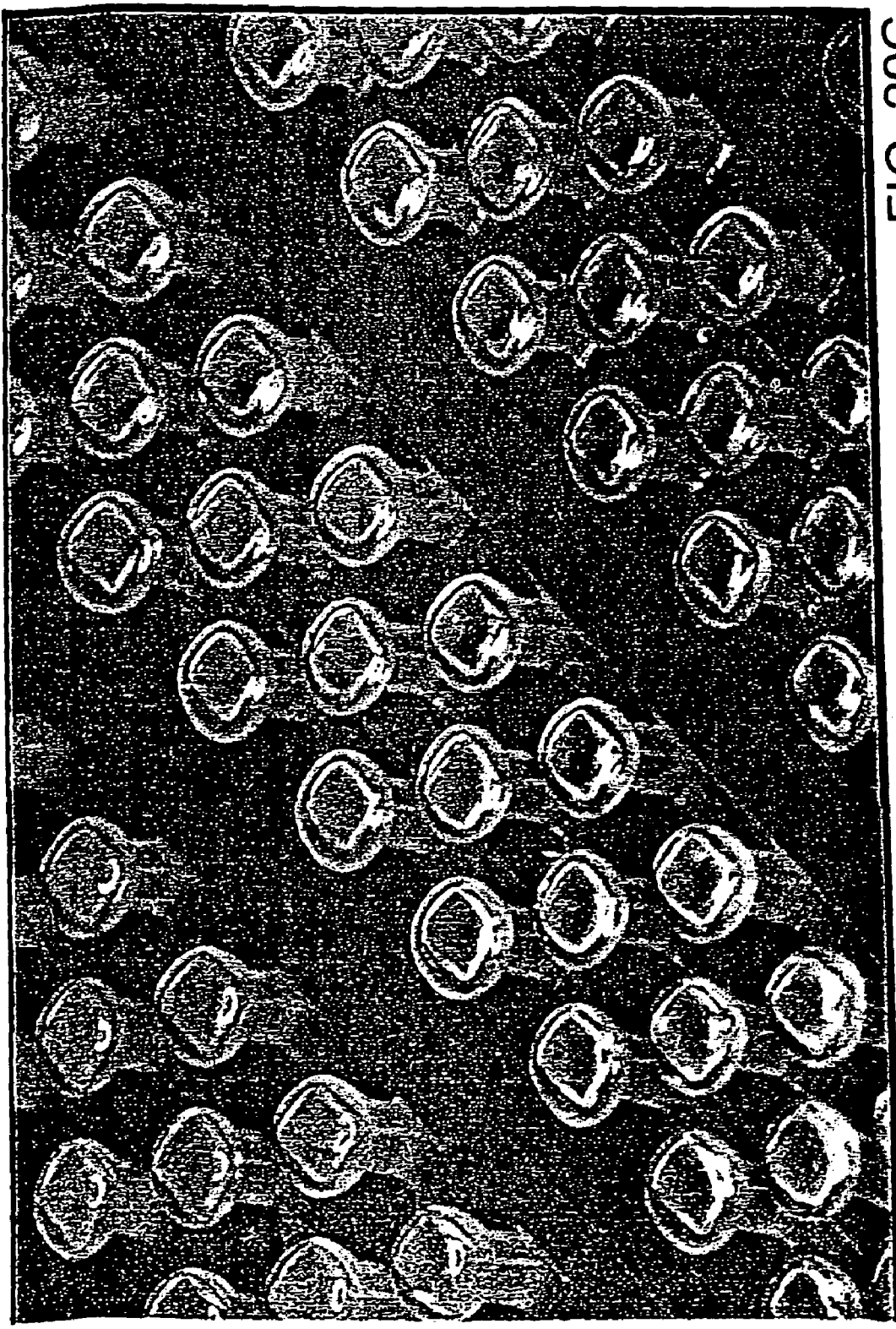

In the pictures of FIGS. 29, 29A a low-density polyethylene resin was chosen. The tip portions were super heated, i.e. heated in excess of that to be removed by cold flat-topping to retain residual gravity flow capability.

Following flat-topping, the flattened resin head gathers under surface tension to form a well shaped mushroom head.

Figure 30:
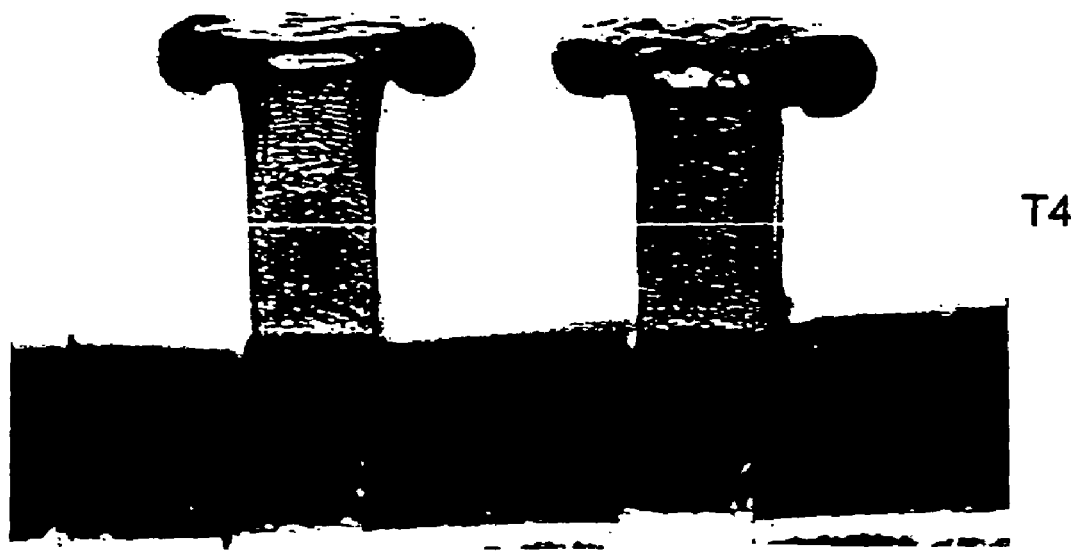
FIGS. 30 and 31 depict the forming of J configurations by post-forming flow, resulting from use of resins of different flow properties, nylon and high density polyethylene, respectively.
Figure 31:
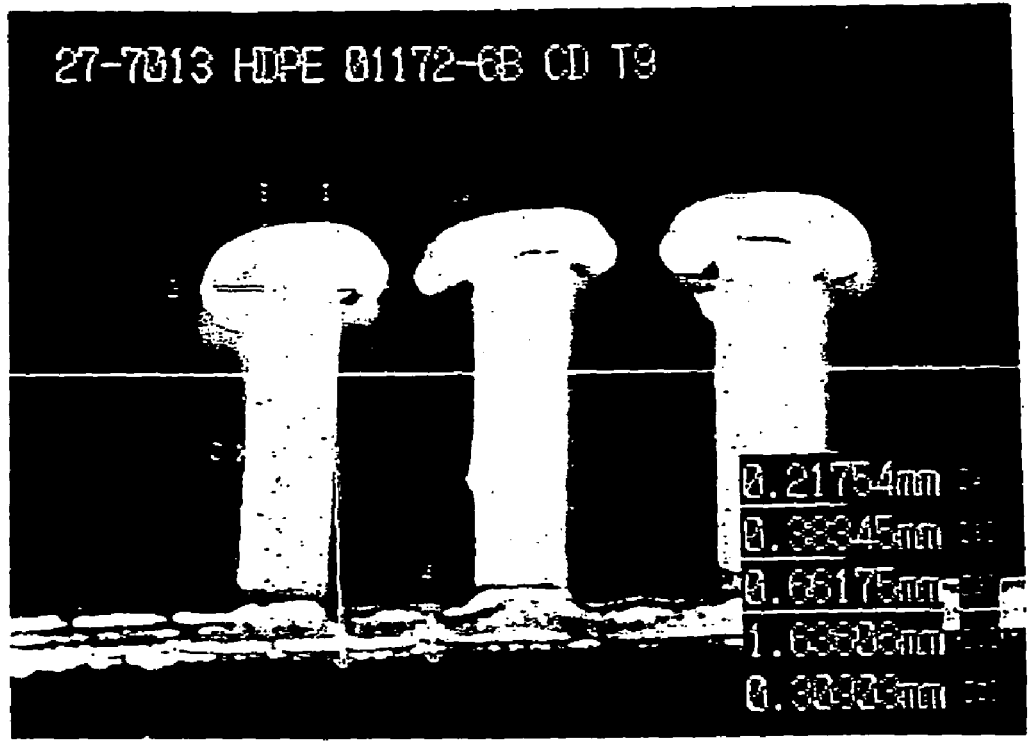

Under essentially the same thermal conditions, the flattened head of nylon and high density polyethylene bent bodily to turn down the peripheral tips of the heads to provide a J profile, see FIGS. 30 and 31.

Figure 32:
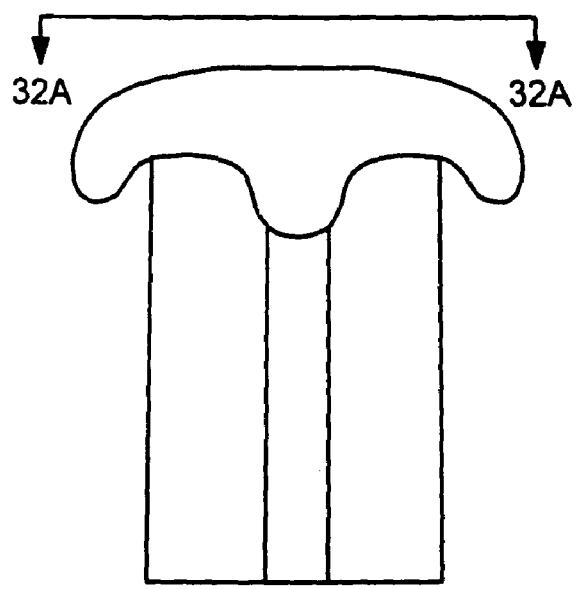
FIGS. 32, 32A and 32B, illustrate another embodiment of a quadrolobal hook, featuring J profile formation.
Figure 32A:
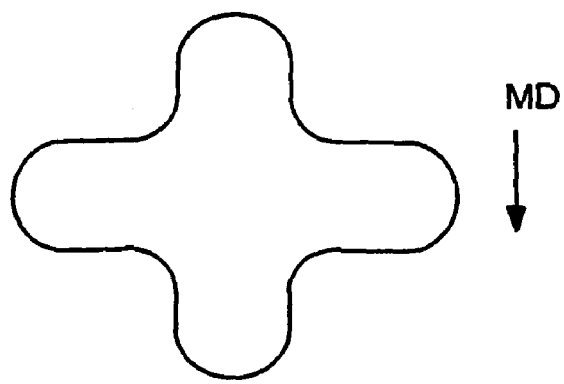
Figure 32B:
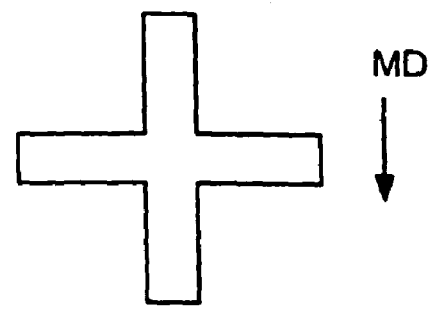

FIG. 32 is a side view of a quadrolobal hook with a curved head that has portions at the fin ends shaped as a J style hook. This is accomplished by choice of the resin of which the preform stem element is molded and appropriate control of the non-contact heating and of the end of the stem and softness of the head following reformation by the conformation roll; e.g. roll 4, to enable a degree of slump of peripheral portions of the resin following flat-topping.

The amount of heat provided prior to the forming determines whether the polymer will flow while, as shown by comparison of FIGS. 29, 29A with FIGS. 30 and 31, the type of resin determines the shape of the formed head and down the stem giving a curved head or whether the ends of the head bend down to provide the J style referred to. The resultant J form is beneficial to retain loops trapped underneath the head.

Figure 33B:
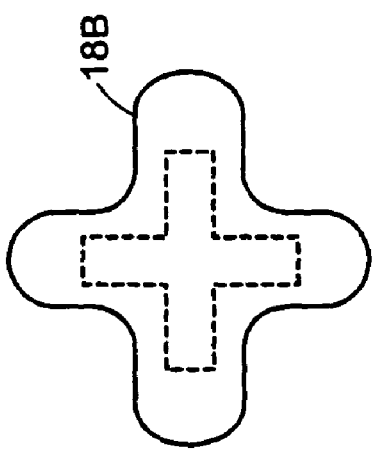
FIGS. 33, 33A and 33B illustrate a quadrolobal M hook while FIGS. 33C, D and E illustrate the molded preform product from which it is fabricated
Figure 33A:
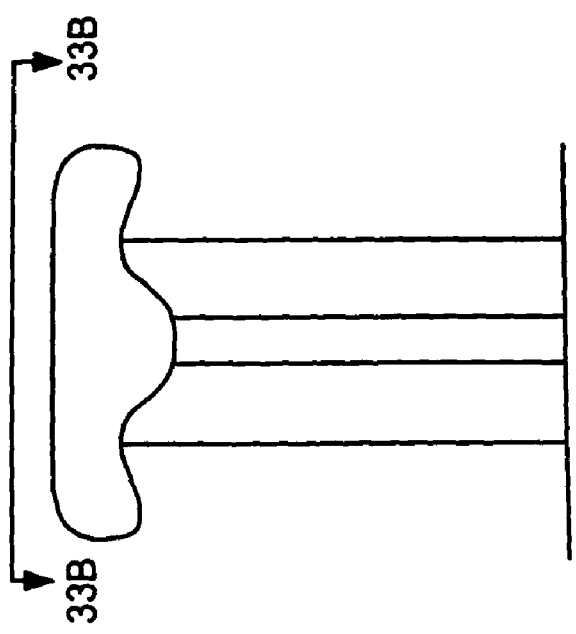
Figure 33:
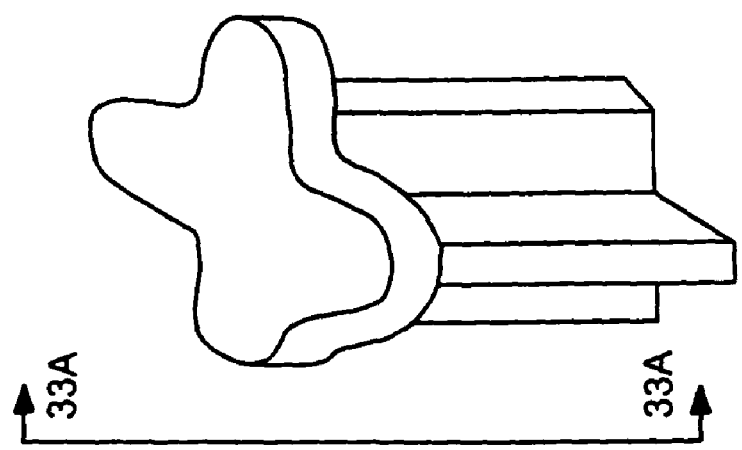
Figure 33F:
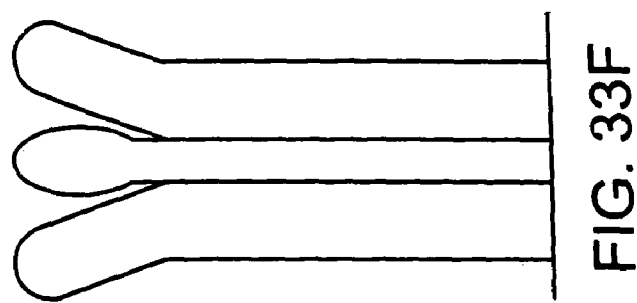
FIG. 33F illustrates the condition of the terminal end of the preform of FIG. 33D after non-contact heating and before flat topping.
Figure 33D:
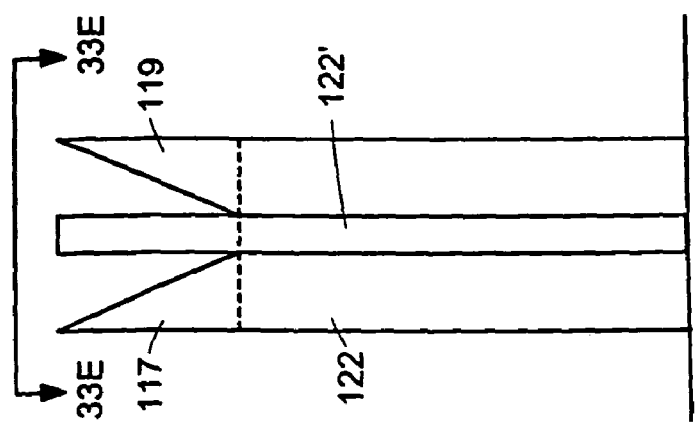
FIGS. 33G, H and I are cross-sectional views as noted that illustrate mold tooling for molding the preform element of FIG. 33.
Figure 33E:
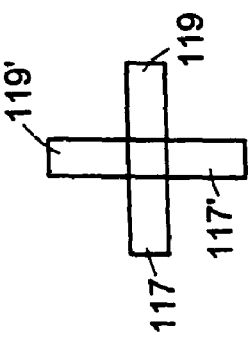
Figure 33C:
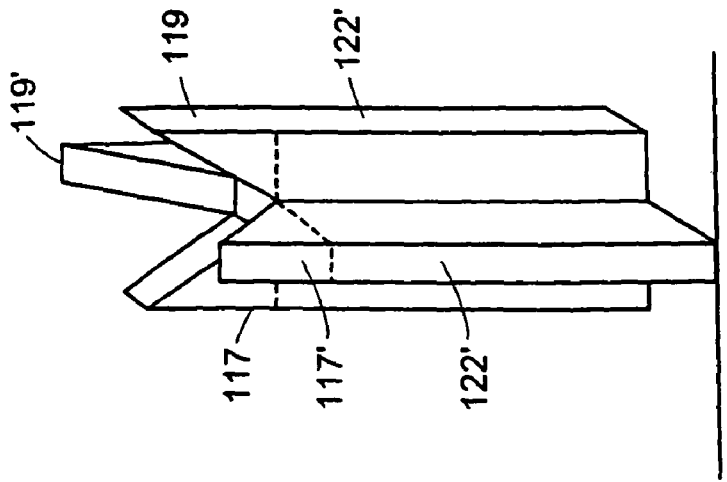
Figure 33G:
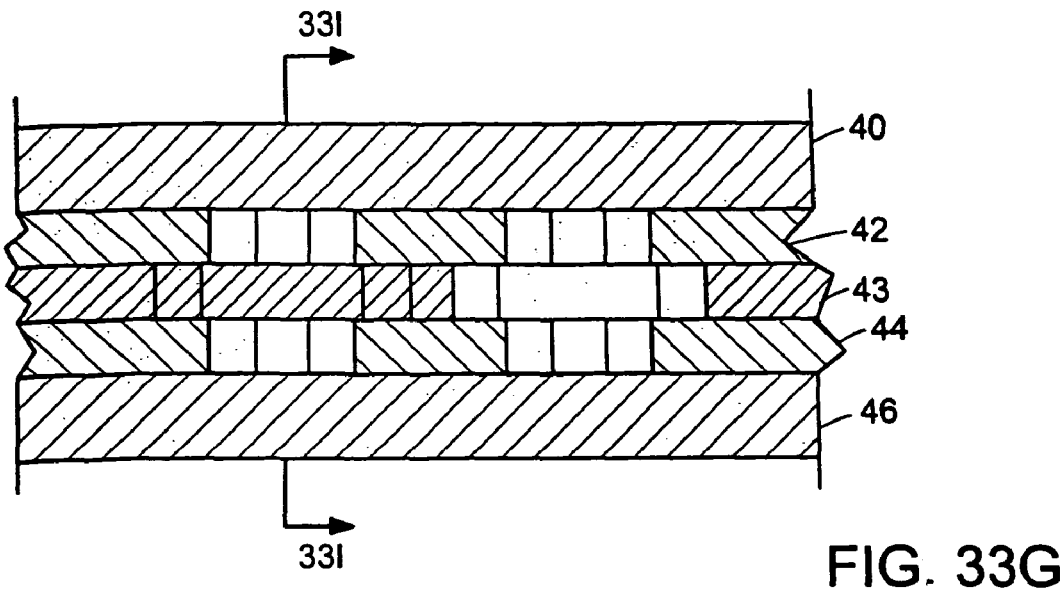
Figure 33H:
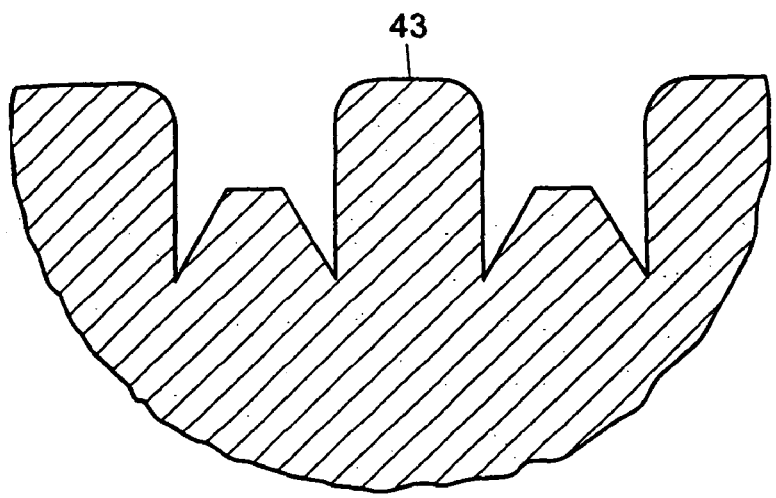
Figure 33I:
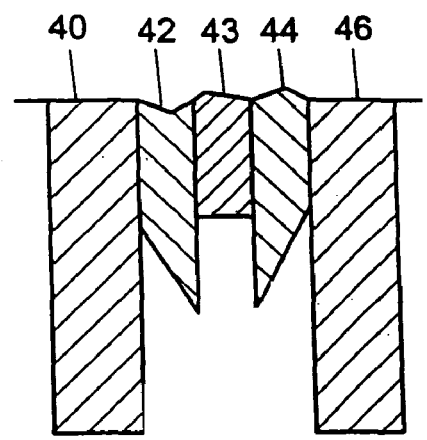

FIGS. 33, 33A and 33B, perspective, side and top views, respectively, show a quadrolobal "M" hook, so-named because of the configuration of the preformed stem from which it is formed, shown in correspondingly FIGS. 33C, D and E and FIGS. 33G, H and I illustrate mold tooling for the element of FIG. 33.

Referring first to FIGS. 17A and 17B, that preformed stem has more polymer at the outer-most portions of the stem in the machine direction, the amount of polymer decreasing linearly moving toward the center of the stem V.

Figure 34E:
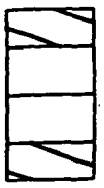
FIGS. 34C, 34D and 34E illustrate the molded preform product from which it is formed, while FIG. 34A' illustrates a hook profile similar to FIGS. 34A, but formed in a different manner.
Figure 34B:
FIGS. 34, 34A and 34B illustrate in the usual manner another embodiment, based on a single M-shaped preform
Figure 34D:
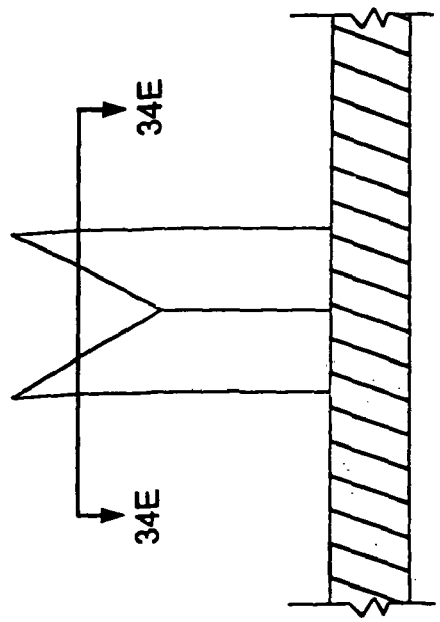
Figure 34A:
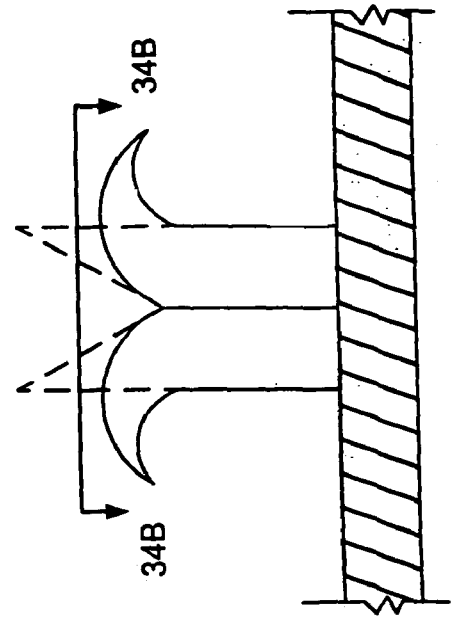
Figure 34:
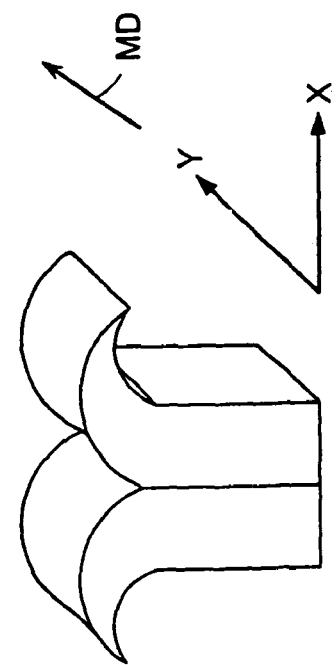
Figure 34C:
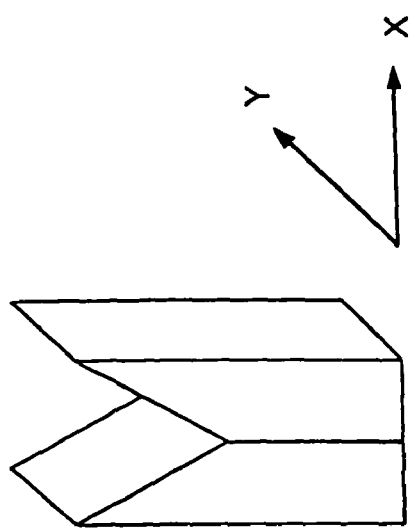
Figure 34A:
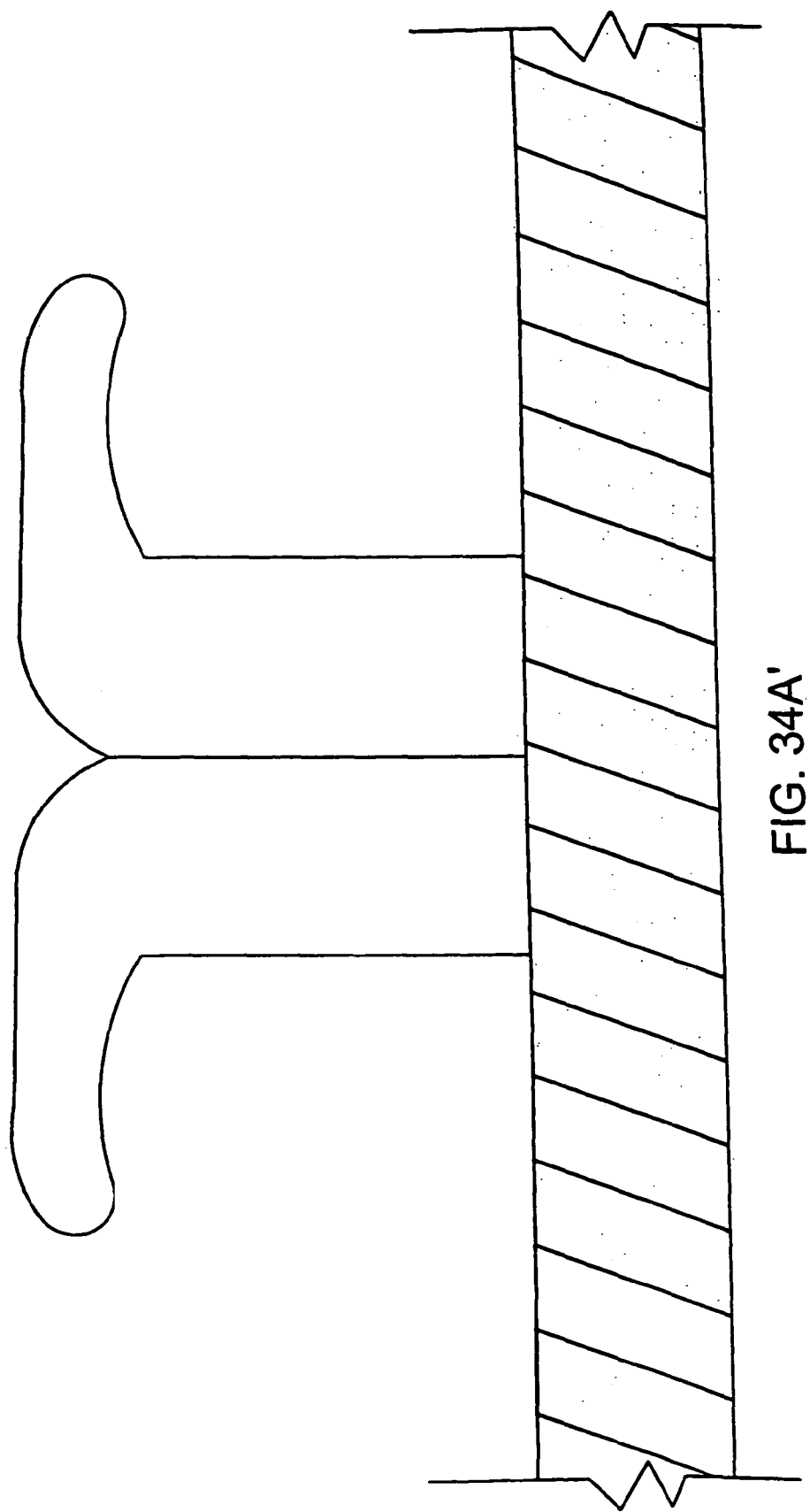

FIGS. 34C, D and E show a similar M stem preform element, oriented in this case in the cross-machine direction, and conceptually formed of two "half M" configuration stem segments, see the corresponding mold tooling shown in FIGS. 34F through 34J.

In the cases of FIGS. 17A and 34, the principle of the thin fin is employed, having more of the resin concentrated at the X direction ends of the fins, adjacent vertical surfaces of the formation. Depending upon the method of deformation, an oval such as the machine direction oval of FIG. 18 or the cross-machine "FIG. 8" head of FIG. 34B can be obtained. With the quadrolobal M stem of FIG. 33 similar deformations can be obtained. In the case of the hook depicted in FIG. 33, non-contact heating provides four lobes of molten resin, concentrated at the periphery, see FIG. 33F. Flat-topping of this resin can then produce the head 18B shown in FIG. 33B. The resin, as it melts, finds the path of least resistance to be predominately at the "precipice" provided at the steep sides of the M, with the desirable result of forming a large Φ angle in the flat-topped product, according to the analysis presented earlier. If a "super heating "condition" is employed, with resins such as Nylon and high density polyethylene, J-shaped profiles are obtainable at the corners.

The M-configuration can usefully be reformed to provide a loop-engageable head by contact heating techniques as well, though potentially at slower speeds. Thus the hot roll and ultrasound techniques described above with respect to FIGS. 12 and 13 may be employed to obtain head shapes that may, in the case of ultrasound or low level heat forming by a heated roll, be more sharply defined as suggested by FIGS. 34 and 34A.

In the case of the non-contact melting followed by flat-topping, steps can be taken also to limit resin flow back toward the center of the "V" shaped void, as suggested by FIGS. 34 and 34A, for instance by limiting the non-contact heating so that only the sharp tips of the M are rendered molten, while the larger cross-sections further down the wedge-form section are rendered mechanically deformable but not molten. Following this, flat topping with a chilled roll below the softening temperature or in some cases with a heated roll at or even above the softening temperature, provides useful hooks for some applications.

FIG. 34A' depicts the profile of a hook provided by the flame heat-cold roll technique, the thicker hook tips being attributable to the non-contacted heated resin that melted and rounded under surface tension prior to the flat topping action.

FIG. 33, the 3-D view of a quadrolobal M hook has larger outer margin portions of the hook head overhanging compared with the hook of FIG. 23. More polymer on the outer portion of the fin is created from a stem that has more polymer on the outer portion of the fins and the distribution of polymer and its proximity to the heat source decreases towards the center of the stem as shown in FIG. 33C.

According to this aspect of the invention, the more the hook heads extend past the stem is beneficial for forming a crook for better engagement, to obtain better holding of loops underneath the hook. A greater distance is then required for the loop to slide off when it is at the top of the stem. When it is at the end of the stem underneath of the head, a greater distance is required for the loop to travel around the head of the stem before disengagement hence the loop will be held better.

FIG. 34B is a top view of FIG. 34A that shows the head of the hook is formed in the cross-machine direction, showing that the bulk of the polymer has indeed been pushed out to the side.

In FIGS. 34A and 34B the Φ angle is approaching 90 degrees, in this case, being high because of the large amount of polymer pressed out to the side. At the loop along the base underneath the hook, by the stem, is at approximately the widest portion of the hook. Therefore, the Φ angle will be very close to 90 degrees and the tendency of the loop to slide off will be very low.

FIG. 34A' illustrates a hook profile similar to that of FIG. 34A.

Figure 34G:
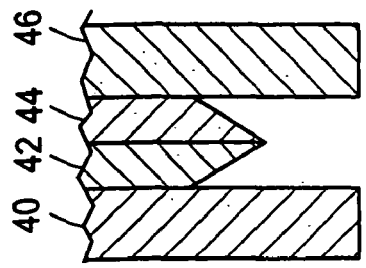
FIG. 34F through FIG. 34J are various cross-sections taken through mold rings of the set as indicated, that define molds for molding the preform stem component of FIGS. 34C, D and E.
Figure 34J:
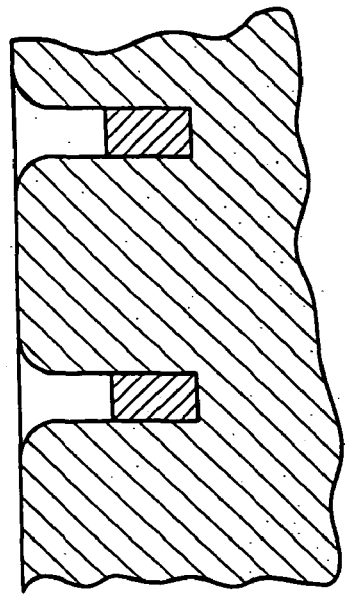
Figure 34F:
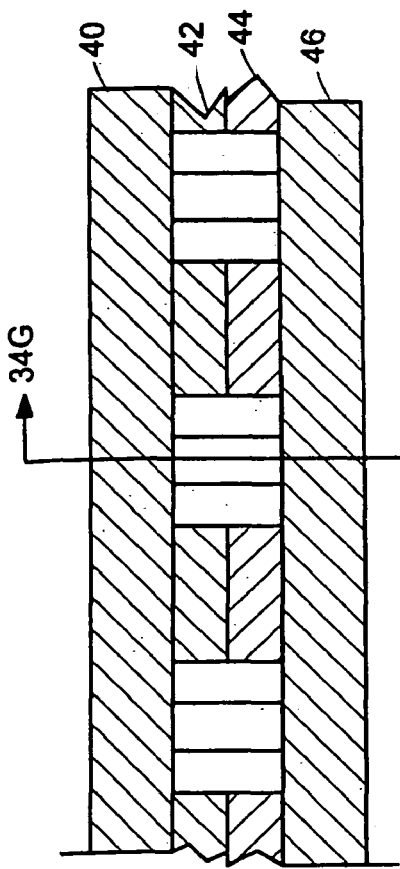
Figure 34I:
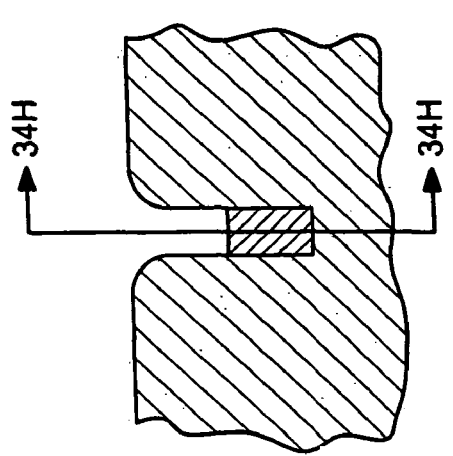
Figure 34H:
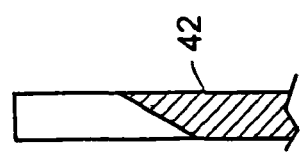

In FIG. 34G the tool ring shown is cut at a 30 degree angle, so that when one of the rings of these figures is flipped over and two are placed together, they provide the center two rings of the mold of FIG. 34F. The rings form a peak together, FIG. 34G. In FIG. 34F two outer spacer rings make-up the beginning and end portion of the M profile.

In FIG. 34F, the four different rings are 40, 42, 44 and 46, ring 42 being the one turned over 180 degrees and otherwise is the same as ring 44.

Figure 35A:
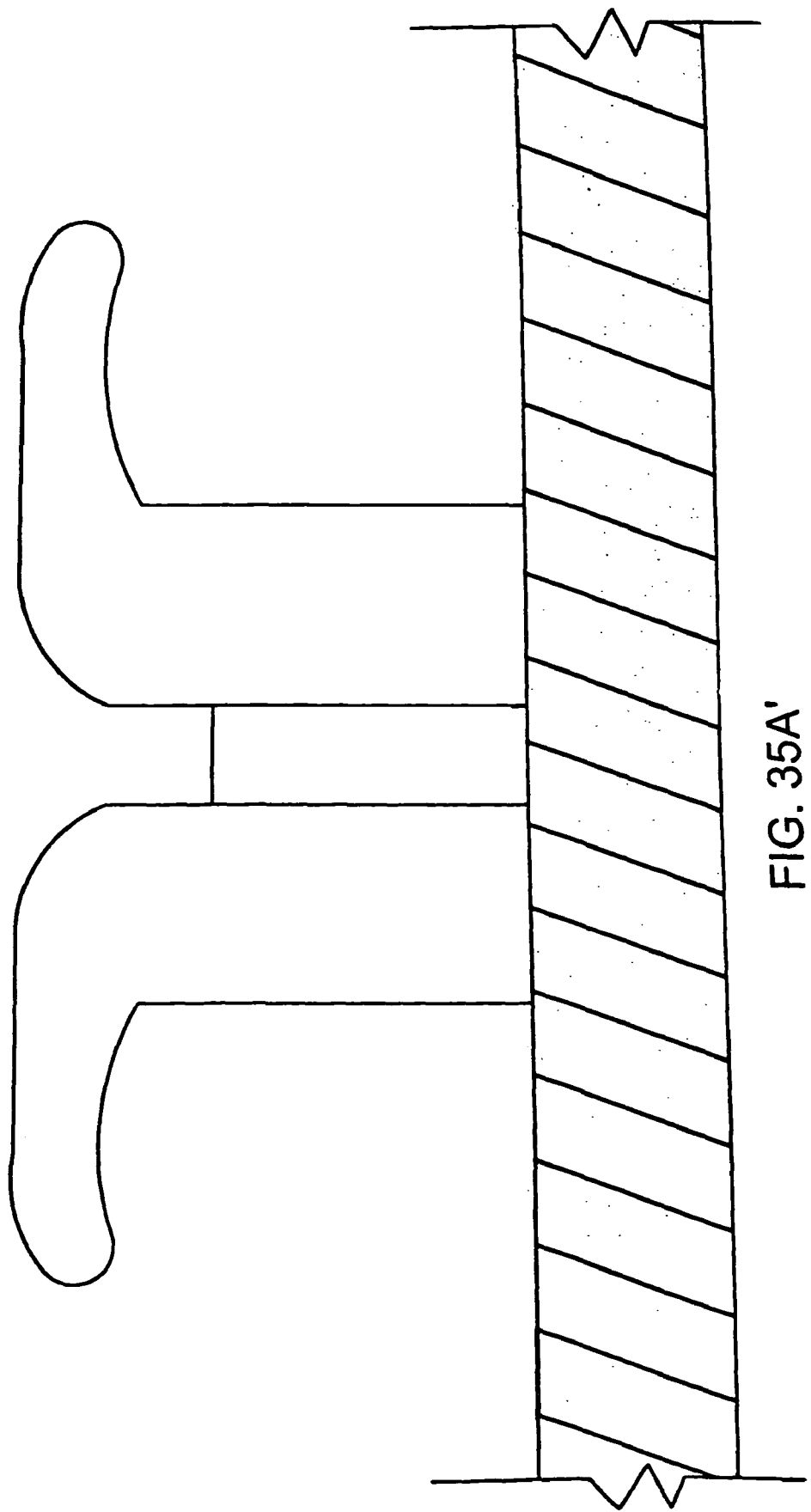
FIGS. 35-35E are views corresponding to FIGS. 34-34E of another embodiment, a modified M, and its preform element, while 35A' illustrates a hook profile similar to FIG. 35A but formed in a different manner.

FIG. 35 shows another alternative of the M style hook in which a small rectangular block is placed between the two halves of the M. This design provides a bigger cross-directional hook. Referring to FIG. 35A it allows more volume of polymer to be excluded between the two hooks. When this preform formation is flat topped, even more resin is pushed out to the sides. FIG. 35A' illustrates a hook profile similar to FIG. 35A but formed in a different manner.

Figure 36A:
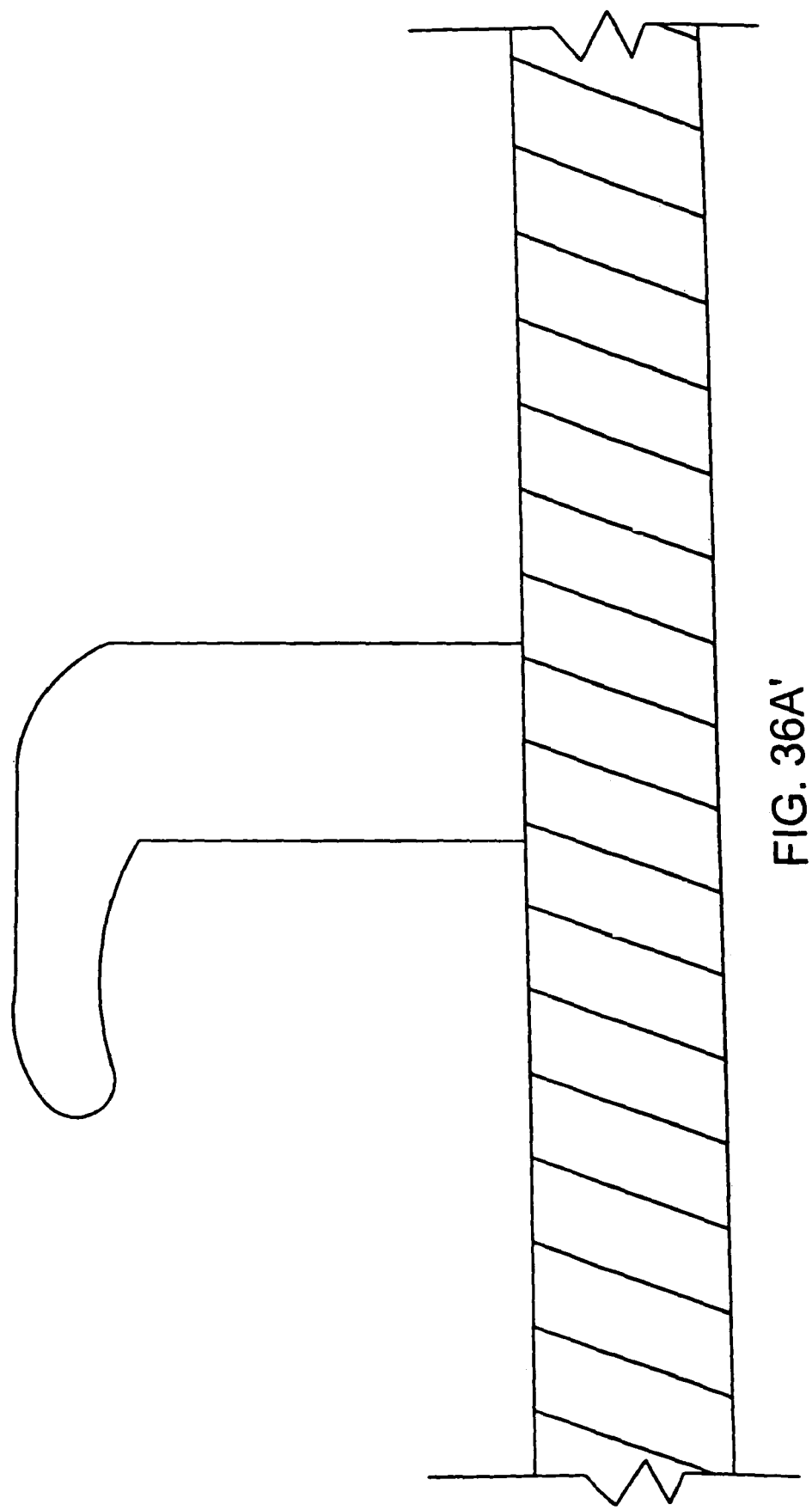
FIGS. 36-36E are similar views of an N hook and its preform element, while FIG. 36A' is a hook profile similar to FIG. 36A but formed in a different manner.

FIG. 36 comprises one side of the M hook design sometimes referred to as an "N" design. It can be used by having half the rings face to the left cross-machine direction and half the rings face to the right cross-machine direction. It enables heating and flat topping a stem to make a hook that bends in one direction in the cross-direction. The benefits of this hook compared to the M hook are a smaller footprint and allowing better penetration into the loop mass, yet still having cross-machine direction features. FIG. 36A' is a hook profile similar to FIG. 36A but formed in a different manner.

Figures 37, 37A, 37B, 37C, 37D, 37E:
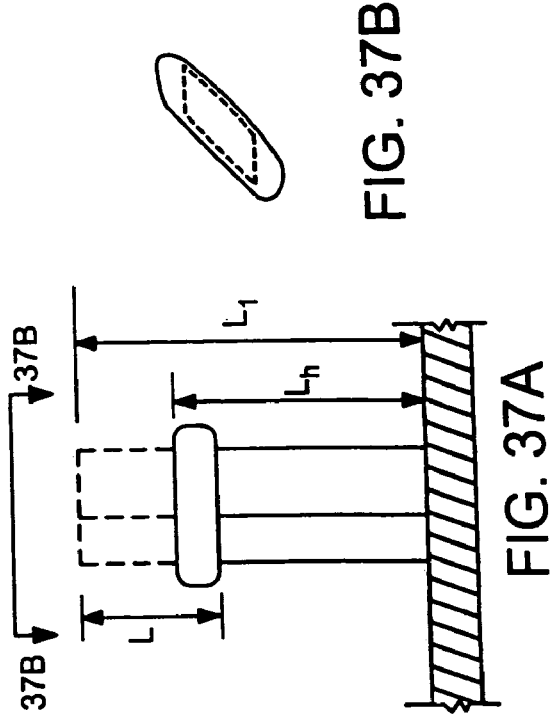

FIGS. 37-37B show a hook element again formed entirely by actions in the machine direction to have significant peel properties in the cross-machine direction.

In this embodiment a monolithic fin has a parallelogram profile in cross-section as shown in FIG. 37E, with its long sides set at an angle of 45° to the machine direction and its short end surfaces aligned with the machine direction.

As a consequence the pair of smaller opposed included angles at the corners of the stem are only 45°, creating a localized region of the tip of the stem having a very high ratio of exposed surface to mass. When exposed to non-contact heating, and in particular to the hot gases of a closely held flame heater, those corners preferentially melt, to be readily deformed by the flat topping action, and indeed, when desired, can be super-heated such that desirable "J" formations can be formed as a consequence of the flow mentioned in respect of FIGS. 30 and 31. Such hook formations have a significant component of orientation in the cross-machine direction.

On the other hand, the other set of corners with large included angle locate a large mass of resin at the cross-machine extremity available to be flattened into a strong loop-engaging disc structure having substantial over-hang beyond the upright stem surface, leading to a large angle Φ. Thus both corners of the parallelogram can contribute significantly but differently to the loop-engaging function.

Figure 37F:
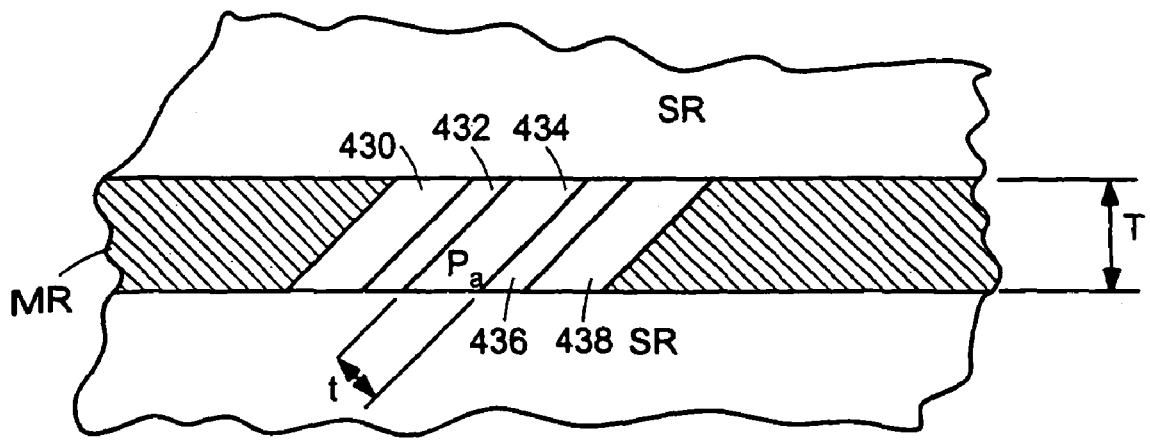
FIGS. 37F and G are cross-sections of mold tooling for molding a variation of the element of FIG. 37C, that includes a supporting pedestal.

Referring to FIGS. 37F and G, the mold ring MR for forming the stem preform of FIG. 37C is formed simply by forming an angular passage fully through the thickness of the metal plate that forms the mold ring, the passage having the required transverse profile end, the thickness of the mold plate thus determining the thickness for the narrow dimension of the thin fin.

Figure 37G:
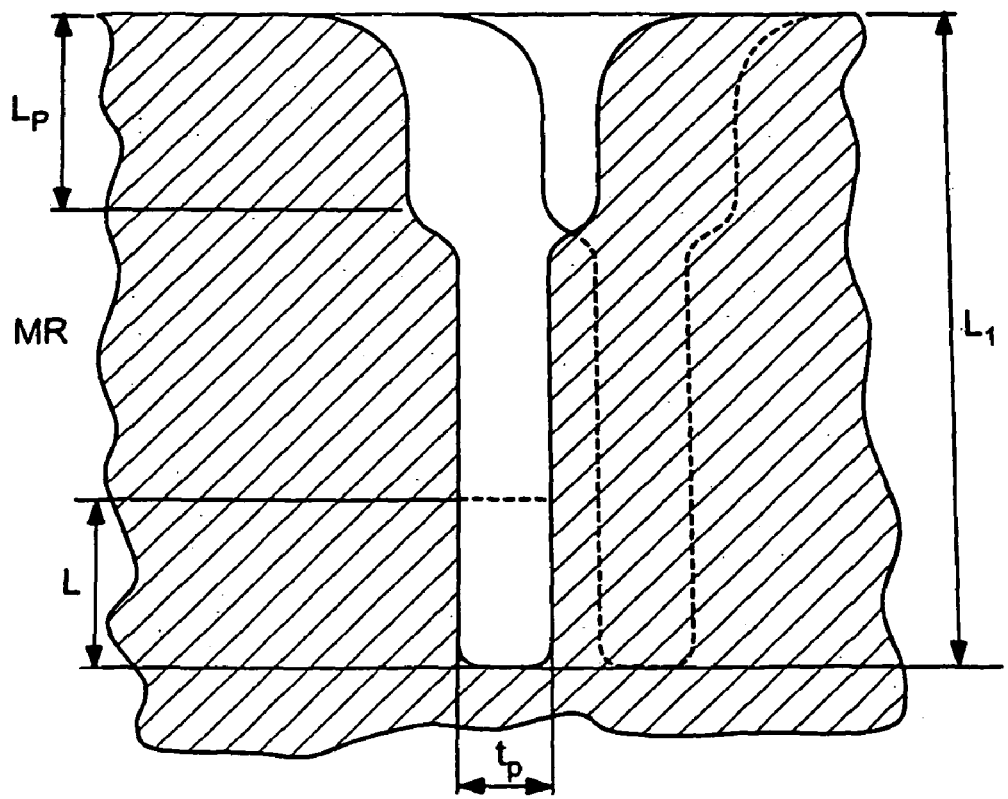
Figure 37H:
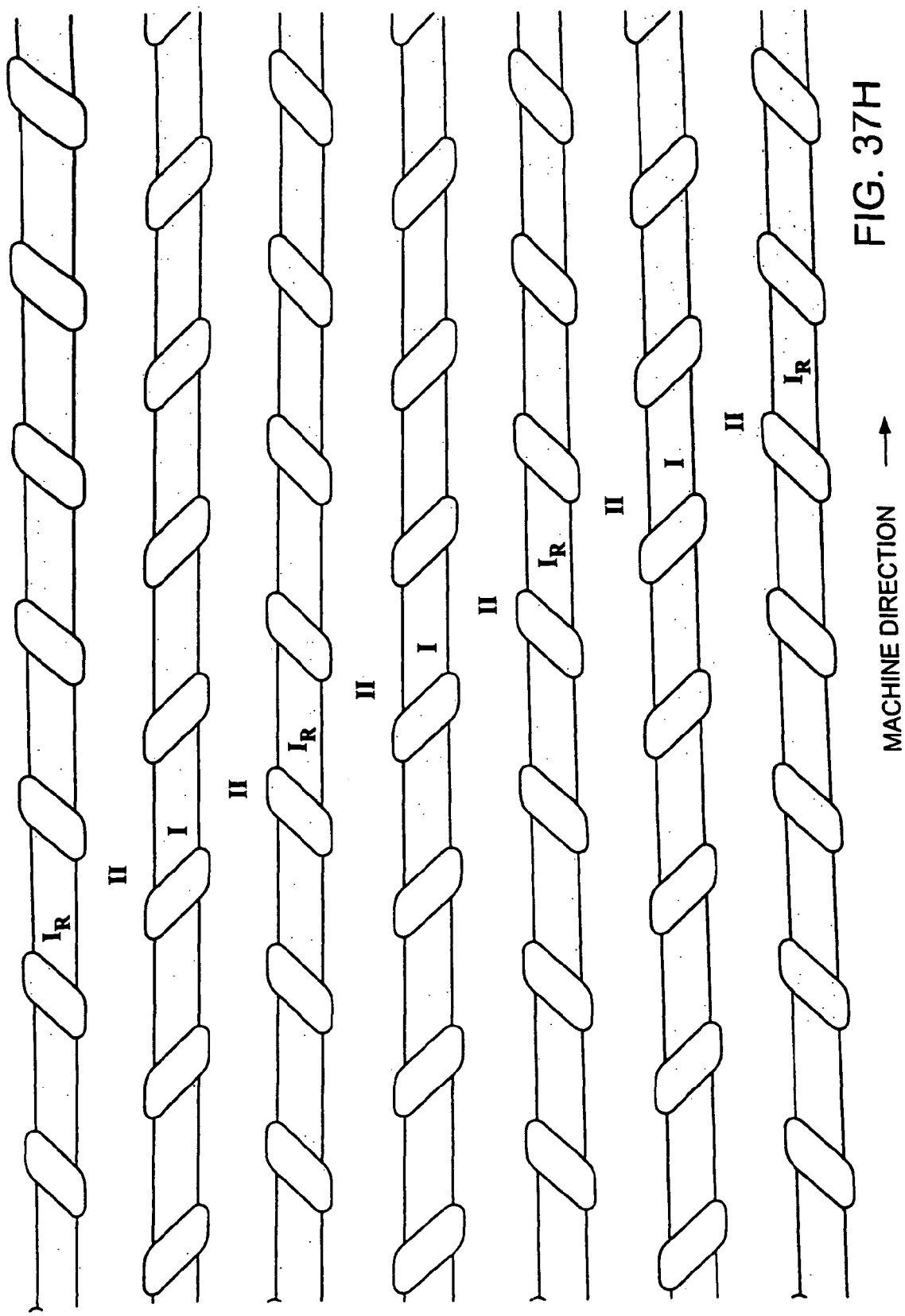
FIG. 37H is a plan view of a male fastener component comprising an X, Y array of the male fastener elements of FIG. 37, while FIGS. 37I and J are diagrammatic perspective views of the array of FIG. 37H.

The alternating male fastener pattern of FIG. 37H is achieved by orienting the parallelograms of adjacent rows of molds in opposite orientations. This is done simply by reversing adjacent mold tool rings, with a solid spacer ring SR face-to-face between each adjacent mold tool ring pair. The bands of the fastener component in FIG. 37H that correspond with the mold rings are indicated by I and $I_R$ and the bands that correspond to the mold spacer ring are indicated by II. ("I" denoting one direction orientation of a mold ring and "$I_R$" the reverse orientation.)

Whereas one embodiment of the parallelogram construction may have straight-sided stems as suggested in FIGS. 37-37E, another advantageous construction, especially for relatively tall fins, for providing columnar strength, has a thickened pedestal portion of the profile. This is readily understood from the mold cavity shown in FIG. 37G, of length $L_1$, with shoulder, of length $L_P$, shown on both of the long sides.

This form is simple to manufacture. The parallelogram seen in the plan view of FIG. 37F relates to the fin structure and its mold cavity as follows. Parallelograms 430 and 438 correspond to the filet-defining stress-relieving transition at the base. The next inward parallelograms 432, 436 represent the strengthening shoulders of the base pedestal of the thin fin, and the central parallelogram 434 represents the main height of the thin fin, extending to its tip.

All of these cavity portions appearing as parallelograms in FIG. 37F extend at 45 degrees to the machine direction of the mold ring.

In a preferred embodiment, with total height $L_1$ of 0.05 inch, the pedestal height B may be 0.020 inch, to provide added columnar strength for the flat-topping operation, and, as well, to enable the mold to provide clearance for removal of the entire fin structure from the rotating mold by the usual expedient of turning about the stripping roll 5. The mold ring plate thickness T, may for instance be 0.010 inch resulting in a diagonal tip to tip length for the fin of 0.020 inch, a length along each side of 0.014 inch a thickness t measured normal to the long sides of 0.005 inch and an end profile thickness $t_p$ of 0.007 inch.

Taking the length of the fin as the full length of one side of 0.014 inch and thickness t measured normal to that side of 0.005, the length to thickness ratio of this fin is 2.8.

With respect to the pointed ends of the fin, flat-topping of those regions can lead to a relatively small radius arc of considerable arc extent, with a resultant Φ angle approaching 90°.

It is anticipated when a loop is engaged on that point, the loop will be prone to pass down the sides away from the tip since it will not be riding along a directly opposed stem, but rather a stem that slants at an angle away from the end of the hook.

Figure 37I:
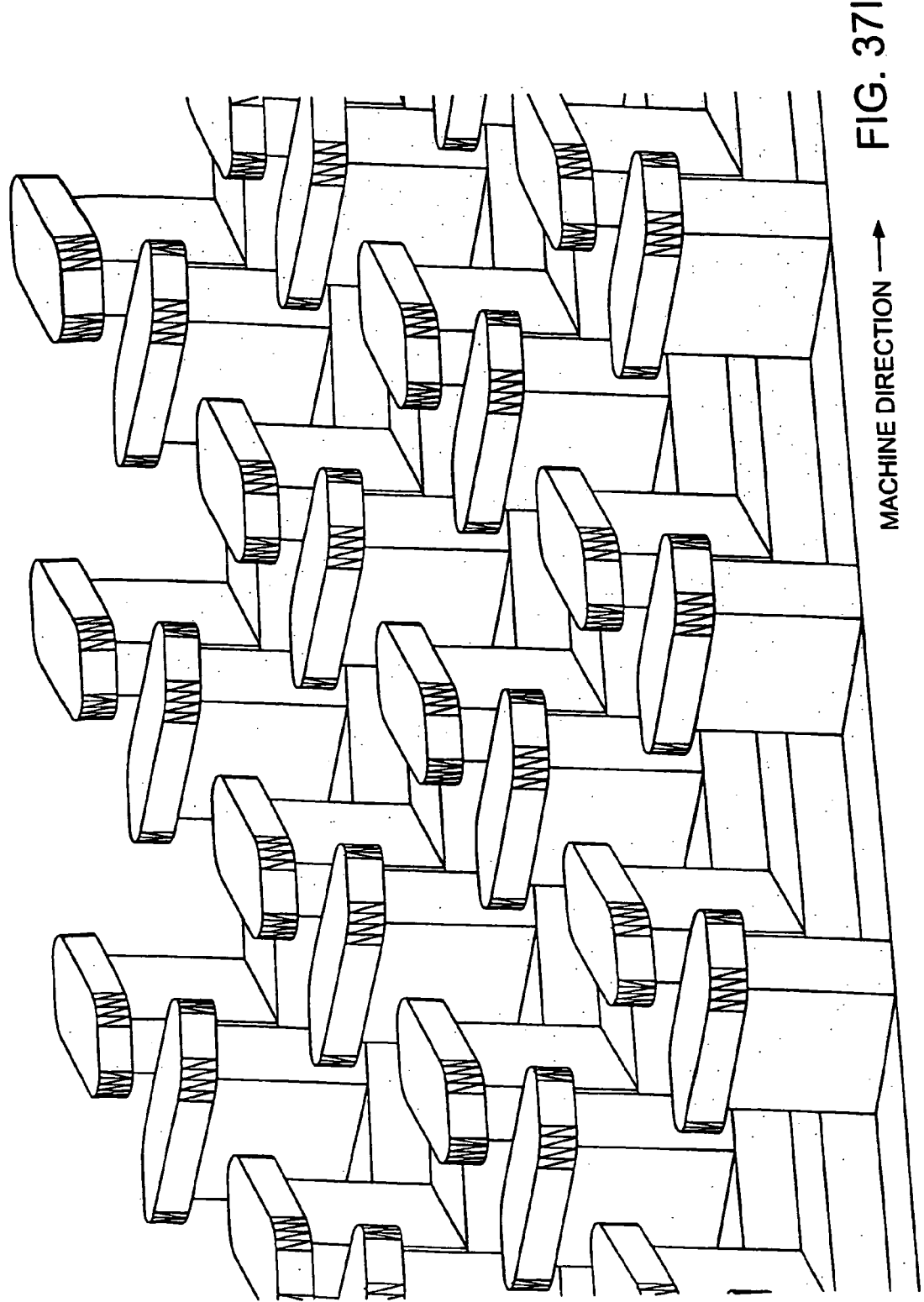
Figure 37J:
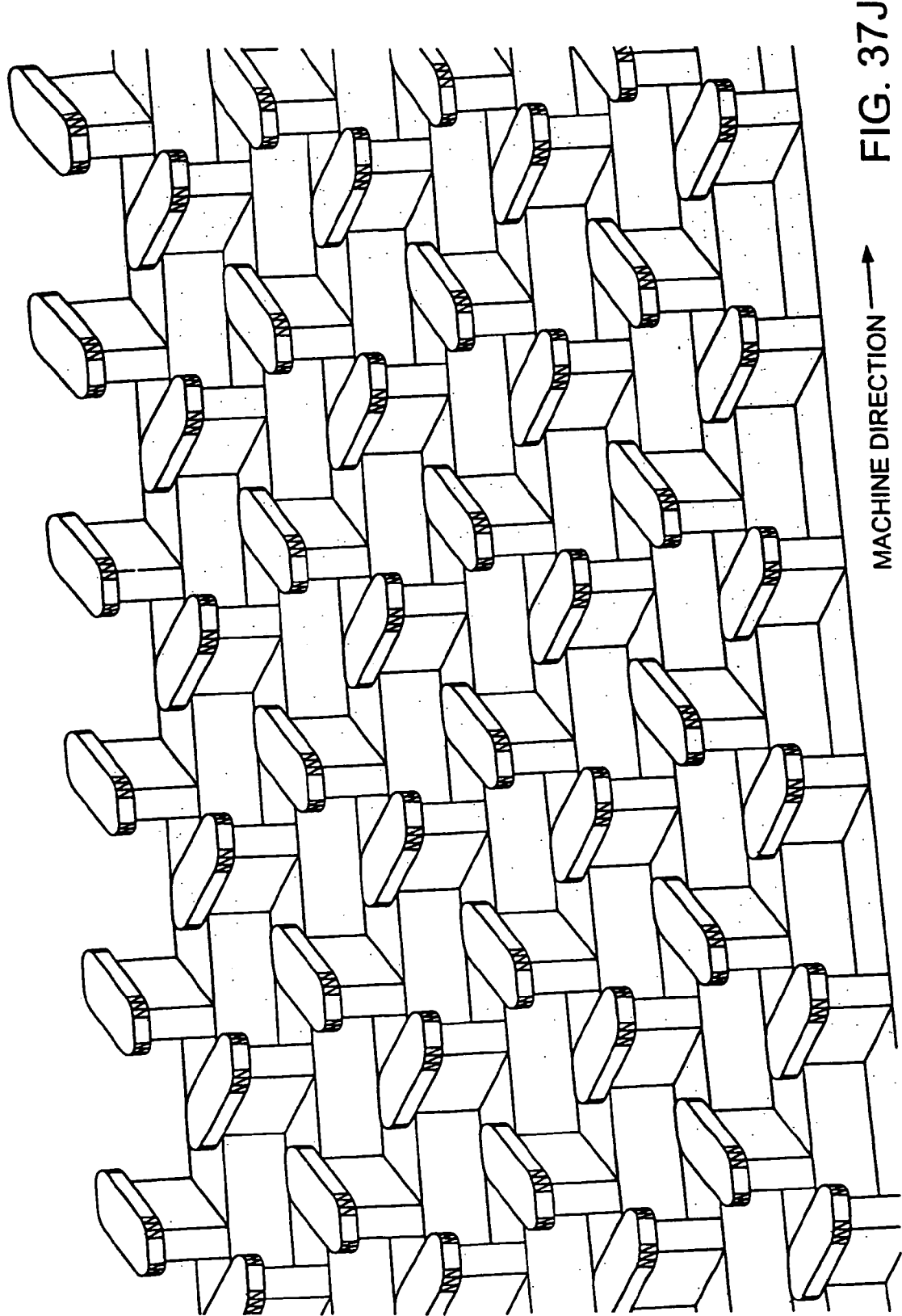
Figure 38:
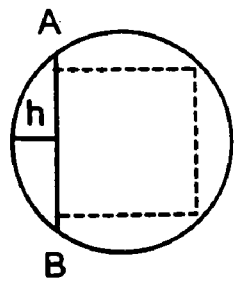
Figure 38A:
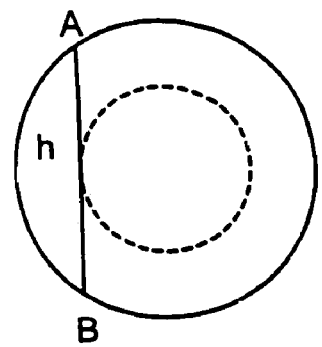
Figure 38B:
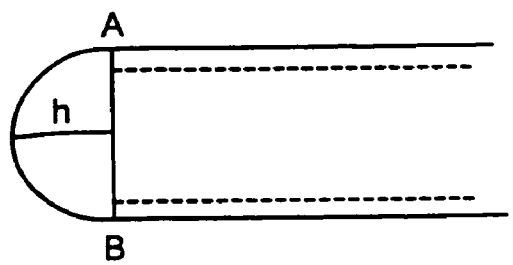
FIG. 38B illustrates the different ratio obtainable with a thin fin stem and FIGS. 38C and 38D illustrate, by two examples, the different relationship obtainable employing the principles of construction described in relation to FIGS. 37-37A.
Figure 38C:
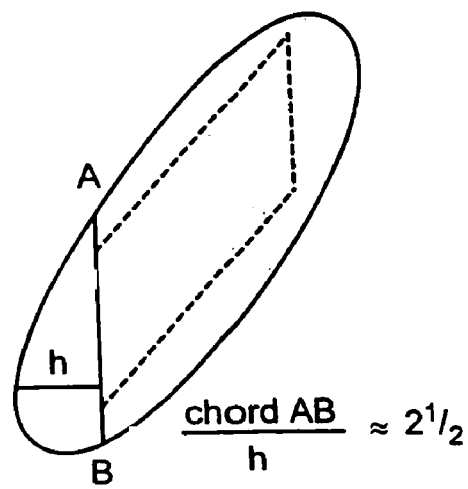
Figure 38D:
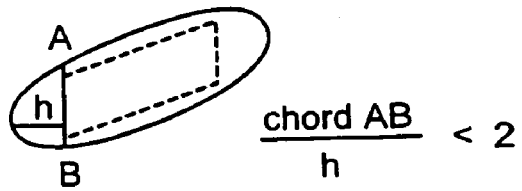

A sense of the loop engagement capability of the embodiments of FIGS. 37-37G is obtained from the diagrammatic perspective views of FIGS. 37I and J, taken from different points of view.

Another benefit of that hook is similar to that of the quadrolobal thin fin hook of FIG. 23, in that a footprint of size equal to that of current hooks manufactured, results in a larger Φ angle about the entire narrow end of the fin. If a loop is engaged on that end it is believed that the Φ angle will be larger compared to standard flat top products that have a square stem.

As has been indicated, the benefits of using convection heating from a gas flame and forming with a cold roll are considerable.

The process allows the polymer to become molten and permits geometric configurations of the remaining formation and the flat topping step to determine the direction of the polymer flow.

The cold roll is beneficial in that it freezes the polymer quickly. This enables high line speeds and relatively inexpensive production of hooks for high volume applications.

Another non-contact heating approach is the use of a radiant heating block the heat from the metal, through radiation, with convection, heats the tips of the stems.

As has been mentioned, another way for forming similar hooks is the ultrasonic method whereby vibration is used for localized heating and deformation as determined by surfaces of the ultrasonic horn or the anvil.

A possible benefit is to obtain desired head shapes, as a consequence of a more localized heating, avoiding effects of surface tension and hence not requiring as large a fin ratio. It may also be beneficial in providing more curvature of the heads and in making a head with a smaller thickness for improved loop penetration, but with the drawback of lower line speed.

Another method used is a hot-wire method which would be a contact method. It would be with a heated wire. When the stems pass and touch the wire they could then be formed by a forming roll or nip. Those would be the main flat-topping methods.

Other features and advantages will become apparent from the following Description of the Preferred Embodiments, the drawings and the claims.

Another aspect of the invention is a composite fabric, and the making of such fabric, on which stems have been directly molded in accordance, for instance, with the teachings of U.S. patent application Ser. No. 09/808,395 filed Mar. 14, 2001, which has been incorporated herein by reference above, followed by use of a flame of burning gas jets or the combustion products flowing from the flame, to rapidly soften the extreme ends of the stems, followed by engagement by a cooled press surface such as a cooled forming bar or a forming roll, as described therein. The numerous features of stem design and conditions of forming the male fastener member as presented here are applicable to the manufacture of such composite materials.

A number of embodiments of the invention have been described. Nevertheless, it will be understood that various modifications may be made without departing from the spirit and scope of the invention. Accordingly, other embodiments are within the scope of the following claims.

What is claimed is:

1. A method of forming a loop-engaging touch fastener product, the method comprising:

providing a preform product formed of thermoformable material and having a sheet-form base and an array of preform stems integrally molded with and extending from the sheet-form base, each of the stems including a first portion joined to the base and a second portion extending from the first portion to a terminal end, an intersection of the first and second portions defining a discrete reduction in transverse cross-sectional area of the stem, measured parallel to the sheet-form base, from the first portion to the second portion, an exposed top surface of the first portion defining a shoulder; and deforming at least some of the second portions toward the shoulder to form engaging heads configured to releasably engage a mating loop product.

2. The method of claim 1, wherein the discrete reduction in transverse cross-sectional area occurs at a distance from a top surface of the sheet-form base of at least halfway to the terminal end of the stem.

3. The method of claim 1, wherein a cross-sectional area taken parallel to the sheet-form base near the terminal end of the second portion is less than 50% of any cross-sectional area of the first portion, also taken parallel to the sheet-form base.

4. The method of claim 3, wherein the cross-sectional area taken near the terminal end of the second portion is less than 25% of any cross-sectional area of the first portion.

5. The method of claim 1, wherein each second portion projects above each first portion without overhanging the sheet-form base.

6. The method of claim 1, wherein each first portion is substantially rectangular in shape in transverse cross-section.

7. The method of claim 1, wherein each second portion is substantially rectangular in shape in transverse cross-section.

8. The method of claim 1, wherein each second portion is substantially circular in shape in transverse cross-section.

9. The method of claim 1, wherein each first portion is substantially cruciform in shape in transverse cross-section.

10. The method of claim 1, wherein each second portion defines a pyramid shape, the intersection of the first and second portions defining a base of the pyramid.

11. The method of claim 1, wherein each of the first and second portions have differently shaped transverse cross-sections.

12. The method of claim 1, wherein each first portion is cruciform in shape in transverse cross-section and each second portion is rectangular in shape in transverse cross-section.

13. The method of claim 1, wherein the deforming step includes heating the terminal ends of the second portions with a non-contact heat source.

14. The method of claim 1, wherein the deforming step includes heating the terminal ends of the second portions with a non-contact heat source, and then contacting the terminal ends with a contact surface.

15. The method of claim 14, wherein the contact surface is maintained at a temperature less than room temperature.

16. The method of claim 13, wherein the non-contact heat source is positioned about 0.1 mm to about 30 mm from the terminal ends of the second portions.

17. The method of claim 13, wherein the non-contact heat source is a flame heater.

18. The method of claim 13, wherein the non-contact heat source is a radiant heat source.

19. The method of claim 1, wherein the deforming step includes heating the terminal end of the second portions by contacting the terminal ends with an ultrasonic horn.

20. The method of claim 1, wherein each head has an overhang aspect ratio, defined as an overall length of a chord extending fully across the head, in top view in a machine direction, directly above a nominal lateral-most extent of the stem, divided by a maximum lateral extent of the head in a cross-machine direction beyond the stem, of less than 4.0.

21. The method of claim 20, wherein the overhang aspect ratio is less than 2.5.

22. The method of claim 21, wherein the overhang aspect ratio is less than 2.0.

23. The method of claim 20, wherein each head has a vertical head thickness, measured perpendicular to the sheet-form base from the top surface of the head to a lower surface of the head, of not more than about 0.015 inch.

* * * * *